United States Patent
Cramp et al.

(10) Patent No.: US 9,242,997 B2
(45) Date of Patent: Jan. 26, 2016

(54) TRICYCLIC PYRAZOLE SULPHONAMIDE COMPUNDS AND METHODS OF MAKING AND USING SAME

(75) Inventors: Susan Mary Cramp, Harlow (GB); Hazel Joan Dyke, Harlow (GB); Thomas David Pallin, Harlow (GB); Robert Zahler, Pennington, NJ (US)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 14/116,029

(22) PCT Filed: May 7, 2012

(86) PCT No.: PCT/US2012/036793
§ 371 (c)(1),
(2), (4) Date: Nov. 6, 2013

(87) PCT Pub. No.: WO2012/154679
PCT Pub. Date: Nov. 15, 2012

(65) Prior Publication Data
US 2014/0080822 A1    Mar. 20, 2014

Related U.S. Application Data

(60) Provisional application No. 61/483,275, filed on May 6, 2011.

(51) Int. Cl.
*C07D 498/14*    (2006.01)
*C07D 471/04*    (2006.01)
*C07D 498/04*    (2006.01)

(52) U.S. Cl.
CPC ............ *C07D 498/14* (2013.01); *C07D 471/04* (2013.01); *C07D 498/04* (2013.01)

(58) Field of Classification Search
CPC ... C07D 498/14; C07D 471/04; C07D 498/04
USPC .................. 514/230.2, 292; 544/101; 546/84
See application file for complete search history.

(56) References Cited

U.S. PATENT DOCUMENTS

| | | | |
|---|---|---|---|
| 5,164,410 A | 11/1992 | Kishimoto et al. | |
| 5,166,172 A | 11/1992 | Kishimoto et al. | |
| 5,180,735 A | 1/1993 | Kishimoto et al. | |
| 5,180,738 A | 1/1993 | Kishimoto et al. | |
| 5,196,406 A | 3/1993 | Kamei et al. | |
| 5,204,345 A | 4/1993 | Kishimoto et al. | |
| 5,238,950 A | 8/1993 | Clader et al. | |
| 5,288,722 A | 2/1994 | Kishimoto et al. | |
| 5,290,807 A | 3/1994 | Folkman et al. | |
| 5,422,363 A | 6/1995 | Yanai et al. | |
| 5,536,623 A | 7/1996 | Ohmachi et al. | |
| 5,698,586 A | 12/1997 | Kishimoto et al. | |
| 5,767,293 A | 6/1998 | Oku et al. | |
| 5,846,562 A | 12/1998 | Yanai et al. | |
| 5,900,431 A | 5/1999 | Molina et al. | |
| 6,017,949 A | 1/2000 | D'Amato et al. | |
| 6,017,954 A | 1/2000 | Folkman et al. | |
| 6,040,337 A | 3/2000 | Hong, II et al. | |
| 6,063,812 A | 5/2000 | Hong et al. | |
| 6,180,626 B1 | 1/2001 | Shimomura et al. | |
| 6,207,704 B1 | 3/2001 | Liu et al. | |
| 6,242,494 B1 | 6/2001 | Craig et al. | |
| 6,268,387 B1 | 7/2001 | Connor et al. | |
| 6,306,819 B1 | 10/2001 | Rupnick et al. | |
| 6,323,228 B1 | 11/2001 | BaMaung et al. | |
| 6,383,471 B1 | 5/2002 | Chen et al. | |
| 6,548,477 B1 | 4/2003 | Olson et al. | |
| 6,566,541 B2 | 5/2003 | Liu et al. | |
| 6,664,244 B1 | 12/2003 | Furuse et al. | |
| 6,803,382 B2 | 10/2004 | Eustache et al. | |
| 6,887,863 B2 | 5/2005 | Craig et al. | |
| 6,989,392 B2 | 1/2006 | Collins et al. | |
| 7,005,440 B1 | 2/2006 | Jayyosi et al. | |
| 7,030,262 B2 | 4/2006 | BaMaung et al. | |
| 7,084,108 B2 | 8/2006 | Olson et al. | |
| 7,115,632 B1 | 10/2006 | Bedell et al. | |
| 7,268,111 B2 | 9/2007 | Olson et al. | |
| 7,282,588 B2 | 10/2007 | Dhanak et al. | |
| 7,288,651 B2 | 10/2007 | Deng et al. | |
| 7,297,816 B2 | 11/2007 | Allison et al. | |
| 7,396,833 B2 | 7/2008 | Xie et al. | |
| 7,491,718 B2 | 2/2009 | Comess et al. | |
| 7,718,695 B2 | 5/2010 | Kim et al. | |
| 8,119,663 B2 | 2/2012 | Heimbach et al. | |
| 8,367,721 B2 | 2/2013 | Hughes et al. | |

(Continued)

FOREIGN PATENT DOCUMENTS

| | | |
|---|---|---|
| EP | 0682020 A1 | 11/1995 |
| WO | WO-98/38859 | 9/1998 |
| WO | WO-99/57097 | 11/1999 |
| WO | WO-99/59986 A1 | 11/1999 |
| WO | WO-99/59987 A1 | 11/1999 |
| WO | WO-00/64876 A1 | 11/2000 |
| WO | WO-01/24796 A1 | 4/2001 |
| WO | WO-02/26782 A2 | 4/2002 |
| WO | WO-02/059124 A2 | 8/2002 |
| WO | WO-02/083065 A2 | 10/2002 |
| WO | WO-03/027104 A1 | 4/2003 |

(Continued)

OTHER PUBLICATIONS

Anderson, "The Use of Fumagillin in Amoebiasis" Ann NY Acad Sci. Dec. 30, 1952;55(6):1118-24.

(Continued)

*Primary Examiner* — Kahsay Habte
(74) *Attorney, Agent, or Firm* — Goodwin Procter LLP

(57) ABSTRACT

The invention provides tricyclic sulfonamide compounds and their use in treating medical disorders, such as obesity. Pharmaceutical compositions and methods of making various tricyclic compounds are provided. The compounds are contemplated to have activity against methionyl aminopeptidase 2.

21 Claims, No Drawings

(56) References Cited

U.S. PATENT DOCUMENTS

| | | |
|---|---|---|
| 2002/0002152 A1 | 1/2002 | Craig et al. |
| 2004/0019113 A1 | 1/2004 | Jozefiak et al. |
| 2004/0067266 A1 | 4/2004 | Toppo |
| 2004/0068012 A1 | 4/2004 | Comess et al. |
| 2004/0116495 A1 | 6/2004 | Marino Jr. et al. |
| 2004/0157836 A1 | 8/2004 | Comess et al. |
| 2004/0167128 A1 | 8/2004 | Comess et al. |
| 2004/0204472 A1 | 10/2004 | Briggs et al. |
| 2005/0037994 A1 | 2/2005 | Kim et al. |
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2008/0312231 A1 | 12/2008 | Merla et al. |
| 2009/0088437 A1 | 4/2009 | Xie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2010/0158855 A1 | 6/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2013/0053364 A1 | 2/2013 | Dyke et al. |
| 2013/0123235 A1 | 5/2013 | Clark et al. |
| 2013/0217759 A1 | 8/2013 | Zahler et al. |
| 2013/0331420 A1 | 12/2013 | Dyke et al. |
| 2014/0073623 A1 | 3/2014 | Cramp et al. |
| 2014/0080822 A1 | 3/2014 | Cramp et al. |
| 2014/0088078 A1 | 3/2014 | Cramp et al. |
| 2014/0378462 A1 | 12/2014 | Pallin et al. |
| 2015/0119456 A1 | 4/2015 | Pallin et al. |

FOREIGN PATENT DOCUMENTS

| | | |
|---|---|---|
| WO | WO-2004/033419 A1 | 4/2004 |
| WO | WO-2005/025554 A2 | 3/2005 |
| WO | WO-2005/082349 A1 | 9/2005 |
| WO | WO-2005/113513 A2 | 12/2005 |
| WO | WO-2006/080591 A1 | 8/2006 |
| WO | WO-2008/008374 A2 | 1/2008 |
| WO | WO-2008/131947 A1 | 11/2008 |
| WO | WO-2009/009501 A2 | 1/2009 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/085198 A1 | 7/2011 |
| WO | WO-2011/088055 A2 | 7/2011 |
| WO | WO-2011/127304 A2 | 10/2011 |
| WO | WO-2011/150338 A1 | 12/2011 |
| WO | WO-2012/012642 A1 | 1/2012 |
| WO | WO-2012/051318 A1 | 4/2012 |
| WO | WO-2012/064838 A1 | 5/2012 |
| WO | WO-2012/064928 A1 | 5/2012 |
| WO | WO-2012/074968 A1 | 6/2012 |
| WO | WO-2012/075020 A1 | 6/2012 |
| WO | WO-2012/075026 A1 | 6/2012 |
| WO | WO-2012/103333 A1 | 8/2012 |
| WO | WO-2012/154676 A1 | 11/2012 |
| WO | WO-2012/154678 A1 | 11/2012 |
| WO | WO-2012/154679 A1 | 11/2012 |
| WO | WO-2013/033430 A1 | 3/2013 |

OTHER PUBLICATIONS

Benny, et al., "An Orally Delivered Small-Molecule Formulation with Antiangiogenic and Anticancer Activity" Nat Biotechnol Jul. 2008;26(7):799-807. doi: 10.1038/nbt1415. Epub Jun. 29, 2008.

Bernier, et al., "Fumagillin class inhibitors of methionine aminopeptidase-2" Drugs of the Future 2005 30(5): 497-500.

Brakenhielm, et al., "Angiogenesis Inhibitor, TNP-470, Prevents Diet-Induced and Genetic Obesity in Mice" Circ Res. Jun. 25, 2004;94(12):1579-88. Epub May 20, 2004.

Braunwald, et al., "Obesity" in Harrison's Principles of Internal Medicine, 15th Ed., 479-86 2001.

Chan, et al. "Discovery of thiophene-2-carboxylic acids as potent inhibitors of HCV NS5B polymerase and HCV subgenomic RNA replication. Part 1: Sulfonamides" Bioorg Med Chem Lett. Feb. 9, 2004;14(3):793-6.

Chun et al. "Novel inhibitors targeted to methionine aminopeptidase 2 (MetAP2) strongly inhibit the growth of cancers in xenografted nude model" Int J Cancer. Mar. 10, 2005;114(1):124-30.

Database Registry [Online] (Apr. 18, 2001), Chemical Abstracts Service, XP002664465.

Database Registry [Online] (Nov. 10, 2004), Chemical Abstracts Service, XP002664464.

Database Registry [Online] (Apr. 13, 2007), Chemical Abstracts Service, XP002664462.

Database Registry [Online] (Aug. 24, 2008), Chemical Abstracts Service, XP002664461.

Database Registry [Online] (Jan. 20, 2009), Chemical Abstracts Service, XP002664460.

Database Registry [Online] (Jan. 23 2009), Chemical Abstracts Service, XP002664459.

Database Registry [Online] (Jan. 27, 2009), Chemical Abstracts Service, XP002664458.

Database Registry [Online] (Sep. 15, 2009), Chemical Abstracts Service, XP002664454.

Database Registry [Online], (Sep. 11, 2009) Chemical Abstracts Service, XP002664455.

Database Registry [Online], (Oct. 4, 2010) Chemical Abstracts Service, XP002664453.

Database Registry [Online] (Jun. 7, 2009) Chemical Abstracts Service, XP002664456.

Database Registry [Online] (Jan. 28, 2009) Chemical Abstracts Service, XP002664457.

Database Registry [Online] (Mar. 13, 2007), Chemical Abstracts Service, XP002664463.

Didier, et al., "Antimicrosporidial Activities of Fumagillin, TNP-470, Ovalicin, and Ovalicin Derivatives in Vitro and In Vivo" Antimicrob Agents Chemother. Jun. 2006;50(6):2146-55.

DiPaolo, et al. "Studies on the Carcinolytic Activity of Fumagillin and Some of its Derivatives" Antibiot Annu. 1958-1959;6:541-6.

Drevs, et al. "Antiangiogenic Potency of FK866/K22.175, a New Inhibitor of Intracellular NAD Biosynthesis, in Murine Renal Cell Carcinoma" Anticancer Res. Nov.-Dec. 2003;23(6C):4853-8.

Dumas, et al., "Synthesis and Structure Activity Relationships of Novel Small Molecule Cathepsin D Inhibitors" Bioorg Med Chem Lett. Sep. 6, 1999;9(17):2531-6.

Eder, et al., "Phase 1 Dose Escalation Safety & Tolerance Study of PPI-2458 in Subjects with Non-Hodgkin's Lymphoma or Solid Tumors" (Presented on Nov. 7-10, 2006 at EORTC-NCI-AACR Symposium on "Molecular Targets and Cancer Therapeutics."), 2006.

European Search Report for EP 09798793 dated Oct. 11, 2011, 9 pages.

Everhart "Contributions of Obesity and Weight Loss to Gallstone Disease" Ann Intern Med. Nov. 15, 1993;119(10):1029-35.

Garrabrant, et al., "Small molecule inhibitors of methionine aminopeptidase type 2 (MetAP-2) fail to inhibit endothelial cell proliferation or formation of microvessels from rat aortic rings in vitro" Angiogenesis. 2004;7(2):91-6.

Han, et al., "Design and Synthesis of Highly Potent Fumagillin Analogues from Homology Modeling for a Human MetAP-2" Bioorg Med Chem Lett. Jan. 3, 2000;10(1):39-43.

Hughes et al. "Ascending dose-controlled trial of beloranib, a novel obesity treatment for safety, tolerability, and weight loss in obese women" Obesity (Silver Spring). Sep. 2013;21(9):1782-8. doi: 10.1002/oby.20356. Epub May 25, 2013.

(56) References Cited

OTHER PUBLICATIONS

Ingber, et al., "Synthetic analogues of fumagillin that inhibit angiogenesis and suppress tumour growth" Nature. Dec. 6, 1990;348(6301):555-7.

Jeong, et al., "Total Synthesis and Antiangiogenic Activity of Cyclopentane Analogues of Fumagillol" *Bioorg Med Chem Lett*. Aug. 1, 2005;15(15):3580-3.

Kawai, et al., "Development of sulfonamide compounds as potent methionine aminopeptidase type II inhibitors with antiproliferative properties" Bioorg Med Chem Lett. Jul. 1, 2006;16(13):3574-7. Epub May 2, 2006.

Kim et al., "Development of parenteral formulation for a novel angiogenesis inhibitor, CKD-732 through complexation with hydroxypropyl-beta-cyclodextrin" Int J Pharm. Mar. 19, 2004;272(12):79-89.

Kim et al., "General pharmacology of CKD-732, a new anticancer agent: effects on central nervous, cardiovascular, and respiratory system," Biol Pharm Bull, Feb. 2005;28(2):217-23.

Kim, et al., "Assessment of the Anti-Obesity Effects of the TNP-470 Analog, CKD-732," J Mol Endocrinol. Apr. 2007;38(4):455-65.

Kruger "TNP-470: An Angiogenesis Inhibitor in Clinical Development for Cancer," Expert Opin Investig Drugs. Jun. 2000;9(6):1383-96.

Lee et al., "Absorption, distribution, metabolism, and excretion of CKD-732, a novel antiangiogenic fumagillin derivative, in rats, mice, and dogs," Arch Pharm Res. Feb. 2004;27(2):265-72.

Lee et al., "Selective N-Demethylation of Tertiary Aminofumagillols with Selenium Dioxide via a Non-classical Polonovski Type Reaction" *Heterocycles* vol. 68, No. 5, 2006, pp. 915-932.

Lee et al., "Design, Synthesis, and Antiangiogenic Effects of a Series of Potent Novel Fumagillin Analogues" Chem Pharm Bull (Tokyo). Jul. 2007;55(7):1024-9.

Lijnen et al., "Fumagillin Reduces Adipose Tissue Formation in Murine Models of Nutritionally Induced Obesity" Obesity (Silver Spring). Dec. 2010;18(12):2241-6. doi: 10.1038/oby.2009.503. Epub Jan. 21, 2010.

Makosza et al. "Reaction of organic anions. 131. Vicarious nucleophilic substitution of hydrogen in nitrobenzoic acids" Makosza, M.; Ludwiczak, S. Dep. Chem.,Tech. Univ. Warsaw, Warsaw, Pol. Synthesis (1986), (1), 50-2. CODEN: SYNTBF ISSN: 0039-7881. Journal written in English. CAN 105:171971 AN 1986:571971 CAPLUS (Copyright (C) 2009 ACS on SciFinder (R)).

Masiero et al. "New Anti-angiogenesis Agents: Review of the Clinical Experience with Carboxyamido-Triazole (CAI), Thalidomide, TNP-470 and Interleukin-12" Angiogenesis. 1997;1(1):23-35.

McCowan, et al., "Fumagillin (H-3), a New Antibiotic with Amebicidal Properties" Science. Feb. 23, 1951;113(2930):202-3.

Milkowski, Deborah M., et al., Antiangiogenic Agents in Cancer Therapy, Chapter 22 "TNP-470," pp. 385-398, 2012.

Molina et al., "Potential Efficacy of Fumagillin in Intestinal Microsporidiosis Due to Enterocytozoon Bieneusi in Patients with HIV Infection: Results of a Drug Screening Study" AIDS. Nov. 1997;11(13):1603-10.

Molina et al., "Fumagillin Treatment of Intestinal Microsporidiosis" N Engl J Med. Jun. 20, 2002;346(25):1963-9.

Molina, et al., "Trial of Oral Fumagillin for the Treatment of Intestinal Microsporidiosis in Patients with HIV Infection" AIDS. Jul. 7, 2000;14(10):1341-8.

Myung et al., "The identification of in vitro metabolites of CKD-732 by liquid chromatography/tandem mass spectrometry" Rapid Commun Mass spectrom. 2002;16(21):2048-53.

Naganuma et al., "Metronomic Doxifluridine Chemotherapy Combined with the Anti-Angiogenic Agent TNP=470 Inhibits the Growth of Human Uterine Carcinosarcoma Xenografts" Cancer Sci. Aug. 2011;102(8):1545-52. doi: 10.1111/j.1349-7006.2011.01998.x. Epub Jul. 3, 2011.

National Task Force on the Prevention and Treatment of Obesity "Very Low-Calorie Diets," JAMA. Aug. 25, 1993;270(8):967-74.

Noel et al., "Increased Risk of Acute Pancreatitis and Biliary Disease Observed in Patients with Type 2 Diabetes" Diabetes Care. May 2009;32(5):834-8. doi: 10.2337/dc08-1755. Epub Feb. 10, 2009.

Pagliarulo et al., "Gallstone disease and related risk factors in a large cohort of diabetic patients" Dig Liver Dis. Feb. 2004;36(2):130-4.

Patra et al., "Regiospecific Synthesis of Benzo[b]fluorenones via Ring Contraction by Benzil—Benzilic Acid Rearrangement of Benz[a]anthracene-5,6-diones" Synthesis 2006, (15), 2556-2562.

International Search Report and Written Opinion for International Application No. PCT/US2011/044864, mailed on Oct. 7, 2011, 7 pages.

International Search Report and Written Opinion for International Application No. PCT/US2010/052050, mailed Mar. 25, 2011, 11 pages.

International Search Report and Written Opinion for International Application No. PCT/US2012/022721, mailed on Mar. 29, 2012, 9 pages.

International Search Report for International Application No. PCT/US2012/036789, mailed Jul. 17, 2012, 4 pages.

International Search Report for International Application No. PCT/US2012/036792, mailed on Jun. 27, 2012 (3 pages).

International Search Report for International Application No. PCT/US2012/036793, mailed on Jun. 21, 2012, 4 pages.

Written Opinion for International Application No. PCT/US2009/066811, mailed on Sep. 1, 2010, 3 pages.

International Search Report and Written Opinion for International Application No. PCT/US2011/055987, mailed Jan. 16, 2012, 24 pages.

International Search Report and Written Opinion for International Application No. PCT/US2013/021919, mailed Mar. 25, 2013, 14 pages.

International Search Report and Written Opinion for International Application No. PCT/US2013/021914, mailed Apr. 18, 2013, 12 pages.

Picoul et al., "Progress in fumagillin synthesis" Pure Appl. Chem., vol. 75, Nos. 2-3, pp. 235-249, 2003.

Rhee et al., "Angiogenesis inhibitor attenuates parathyroid hormone-induced anabolic effect" Biomed Pharmacother. Jan. 2009;63(1):63-8. doi: 10.1016/j.biopha.2007.10.013. Epub Nov. 20, 2007.

Rupnick "Adipose Tissue Mass Can be Regulated Through the Vasculature" Proc Natl Acad Sci U S A. Aug. 6, 2002;99(16):10730-5. Epub Jul. 29, 2002.

Sankar et al., "2-[1-(Phenylsulfonyl)ethyl]benzoic acid and 2-[1-(phenylsulfonyl)propyl]benzoic acid" Acta Crystallogr C. May 2002;58(Pt 5):o257-9. Epub Apr. 11, 2002.

Seneca et al., "Amebiasis: a review. II. Laboratory diagnosis, differential diagnosis and therapy" Am J Dig Dis. Jul. 1956;1(7):310-22.

Sheppard et al., "3-Amino-2-hydroxyamides and related compounds as inhibitors of methionine aminopeptidase-2" Bioorg Med Chem Lett. Feb. 23, 2004;14(4):865-8.

Sheppard et al., "Discovery and Optimization of Anthranilic Acid Sulfonamides as Inhibitors of Methionine Aminopeptidase-2: A Structural Basis for the Reduction of Albumin Binding" J Med Chem. Jun. 29, 2006;49(13):3832-49.

Shin et al., "A Phase lb pharmacokinetic study of the anti-angiogenic agent CKD-732 used in combination with capecitabine and oxaliplatin (XELOX) in metastatic colorectal cancer patients who progressed on irinotecan-based chemotherapy" Invest New Drugs. Apr. 2012;30(2):672-80. doi: 10.1007/s10637-010-9625-x. Epub Dec. 29, 2010.

Shin "A phase I pharmacokinetic and pharmacodynamic study of CKD-732, an antiangiogenic agent, in patients with refractory solid cancer" Invest New Drugs. Oct. 2010;28(5):650-8. doi: 10.1007/s10637-009-9287-8. Epub Jul. 8, 2009.

Shvedov et al., "Functional Derivatives of Thiophene" Chemistry of Heterocyclic Compounds Feb. 1977, vol. 13, Issue 2, pp. 163-165.

Siddiqui et al., "The Presence of Substituents on the Aryl Moiety of the Aryl Phosphoramidate Derivative of d4T Enhances Anti-HIV Efficacy in Cell Culture: A Structure-Activity Relationship" *J Med Chem*. Feb. 11, 1999;42(3):393-9.

(56) References Cited

OTHER PUBLICATIONS

Srikumar et al., "Structural Insights on Brugia Malayi Transglutaminase With Cinnamoyl Derivatives—A Molecular Docking Approach" Int J Pharm Bio Sci Jul. 2012; 3(3): (B) 998—1006.

Teicher, et al., "Antiangiogenic Agents in Cancer Therapy" pp. 385-398, 1999.

Thirumamagal, et al., "Formation of 2-arylindane-1,3-diones and 3-alkylphthalides from methyl o-[-phenylsulfonyl]toluate" Tetrahedron Letters (2008), 49(3), 512-515.

Wang, et al., "Lead optimization of methionine aminopeptidase-2 (MetAP2) inhibitors containing sulfonamides of 5, 6-disubstituted anthranilic acids" Bioorg Med Chem Lett. May 15, 2007;17(10):2817-22. Epub Feb. 25, 2007.

Wang, et al., "Tumor Suppression by a Rationally Designed Reversible Inhibitor of Methionine Aminopeptidase-2" Cancer Res. Nov. 15, 2003;63(22):7861-9.

Wang et al. "Correlation of tumor growth suppression and methionine aminopetidase-2 activity blockade using an orally active inhibitor" *Proc Natl Acad Sci U S A*. Feb. 12, 2008;105(6):1838-43. doi: 10.1073/pnas.0708766105. Epub Feb. 5, 2008.

Weinsier et al., "Gallstone Formation and Weight Loss" Obes Res. Jan. 1993;1(1):51-6.

Weinsier, et al., "Medically Safe Rate of Weight Loss for the Treatment of Obesity: A Guideline Based on Risk of Gallstone Formation" Am J Med. Feb. 1995;98(2):115-7.

Winter et al., "Endothelial $\alpha_v\beta_3$ Integrin-Targeted Fumagillin Nanoparticles Inhibit Angiogenesis in Atherosclerosis," Arterioscler Thromb Vasc Biol. Sep. 2006;26(9):2103-9. Epub Jul. 6, 2006.

Yanai, et al., "Antitumor Effect of Arterial Administration of a Medium-Chain Triglyceride Solution of an Angiogenesis Inhibitor, TNP-470, in Rabbits Bearing VX-2 Carcinoma" Pharm Res. May 1995;12(5):653-7.

Yanai, et al., "Antitumor activity of a medium-chain triglyceride solution of the angiogenesis inhibitor TNP-470 (AGM-1470) when administered via the hepatic artery to rats bearing Walker 256 carcinosarcoma in the liver" J Pharmacol Exp Ther. Dec. 1994;271(3):1267-73.

TRICYCLIC PYRAZOLE SULPHONAMIDE COMPUNDS AND METHODS OF MAKING AND USING SAME

CROSS REFERENCE TO RELATED APPLICATIONS

This application is a national stage filing under 35 U.S.C. §371 of PCT/US2012/036793, filed May 7, 2012, which claims priority to U.S. Ser. No. 61/483,275 filed May 6, 2011, all of which are incorporated by reference in their entirety.

BACKGROUND

Over 1.1 billion people worldwide are reported to be overweight. Obesity is estimated to affect over 90 million people in the United States alone. Twenty-five percent of the population in the United States over the age of twenty is considered clinically obese. While being overweight or obese presents problems (for example restriction of mobility, discomfort in tight spaces such as theater or airplane seats, social difficulties, etc.), these conditions, in particular clinical obesity, affect other aspects of health, i.e., diseases and other adverse health conditions associated with, exacerbated by, or precipitated by being overweight or obese. The estimated mortality from obesity-related conditions in the United States is over 300,000 annually (O'Brien et al. Amer J Surgery (2002) 184:4S-8S; and Hill et al. (1998) Science, 280:1371).

There is no curative treatment for being overweight or obese. Traditional pharmacotherapies for treating an overweight or obese subject, such as serotonin and noradrenergic re-uptake inhibitors, noradrenergic re-uptake inhibitors, selective serotonin re-uptake inhibitors, intestinal lipase inhibitors, or surgeries such as stomach stapling or gastric banding, have been shown to provide minimal short-term benefits or significant rates of relapse, and have further shown harmful side-effects to patients.

MetAP2 encodes a protein that functions at least in part by enzymatically removing the amino terminal methionine residue from certain newly translated proteins such as glyceraldehyde-3-phosphate dehydrogenase (Warder et al. (2008) J Proteome Res 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res. 63:7861) and infectious diseases such as microsporidiosis, leishmaniasis, and malaria (Zhang et al. (2002) J. Biomed. Sci. 9:34). Notably, inhibition of MetAP2 activity in obese and obese-diabetic animals leads to a reduction in body weight in part by increasing the oxidation of fat and in part by reducing the consumption of food (Rupnick et al. (2002) Proc. Natl. Acad. Sci. USA 99:10730).

Such MetAP2 inhibitors may be useful as well for patients with excess adiposity and conditions related to adiposity including type 2 diabetes, hepatic steatosis, and cardiovascular disease (via e.g. ameliorating insulin resistance, reducing hepatic lipid content, and reducing cardiac workload). Accordingly, compounds capable of modulating MetAP2 are needed to address the treatment of obesity and related diseases as well as other ailments favorably responsive to MetAP2 modulator treatment.

SUMMARY

The invention provides, for example, compounds which may be modulators of MetAP2, and their use as medicinal agents, processes for their preparation, and pharmaceutical compositions containing them as an active ingredient both alone or in combination with other agents, as well as provides for their use as medicaments and/or in the manufacture of medicaments for the inhibition of MetAP2 activity in warm-blooded animals such as humans. In particular this invention relates to compounds useful for the treatment of obesity, type 2 diabetes, and other obesity-associated conditions. Also provided are pharmaceutical compositions comprising at least one disclosed compound and a pharmaceutically acceptable carrier.

In an embodiment, provided herein are compounds represented by formula I and II:

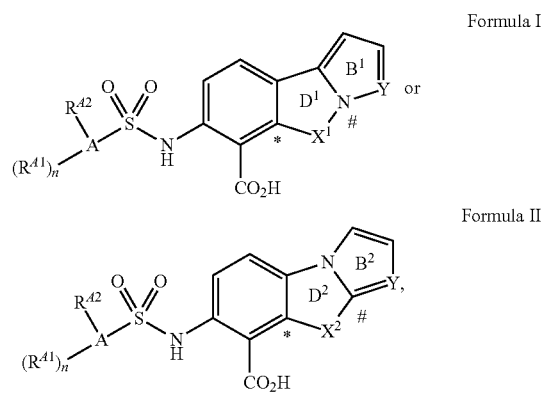

or pharmaceutically acceptable salts, stereoisomers, esters or prodrugs thereof, where A, $B^1$, $B^2$, $D^1$, $D^2$, $R^{41}$, $R^{42}$, Y, $X^1$, $X^2$ and n are as defined herein.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

DEFINITIONS

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "cyano" as used herein refers to the radical —CN.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to saturated or partially unsaturated 4-7 membered ring structures, whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of obesity or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in weight loss.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereo selective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the invention may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_{1-8}$)alkyl, ($C_{2-12}$)alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_{1-2}$)alkylamino($C_{2-3}$)alkyl (such as β-dimethylaminoethyl), carbamoyl-($C_{1-2}$)alkyl, N,N-di($C_{1-2}$)alkylcarbamoyl-($C_{1-2}$)alkyl and piperidino-, pyrrolidino- or morpholino ($C_{2-3}$)alkyl.

Similarly, if a compound of the invention contains an alcohol functional group, a prodrug can be formed by the replacement of the hydrogen atom of the alcohol group with a group such as ($C_{1-6}$)alkylcarbonyloxymethyl, 1-(($C_{1-6}$)alkylcarbonyloxy)ethyl, 1-methyl-1-(($C_{1-6}$)alkylcarbonyloxy)ethyl ($C_{1-6}$)alkoxycarbonyloxymethyl, N—($C_{1-6}$)alkoxycarbonylaminomethyl, succinoyl, ($C_{1-6}$)alkylcarbonyl, α-amino ($C_{1-4}$)alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, P(O) (OH)$_2$, —P(O)(O($C_{1-6}$)alkyl)$_2$ or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Símplicio, et al., *Molecules* 2008, 13, 519 and references therein.

I. Tricyclic Compounds

In certain embodiments, the present invention provides compounds of Formula I and Formula II:

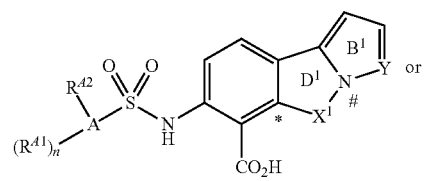

Formula I

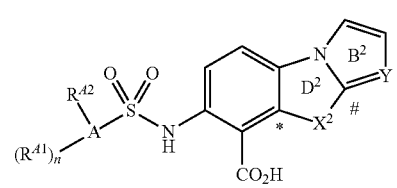

Formula II wherein:

$D^1$ and $D^2$ may each be 5-7 membered heterocyclic or heteroaromatic rings in which one of the two atoms in common between rings B and D is nitrogen and the other is carbon;

$X^1$ may be selected from the group consisting of: *—C($R^{D1}R^{D2}$)—#, *—C($R^{D1}R^{D2}$)—C($R^{D5}R^{D6}$)—#, *—C($R^{C1}$)=C($R^{C2}$)—#, *—N=C($R^{C2}$)—#, *—$W^1$—C($R^{D5}R^{D6}$)—#, *—$W^1$—C(O)—#, *—C($R^{D1}R^{D2}$)—C(O)—#, *—C($R^{D1}R^{D2}$)—C($R^{D3}R^{D4}$)—C($R^{D5}R^{D6}$)—#, *—$W^1$—C($R^{D3}R^{D4}$)—C($R^{D5}R^{D6}$)—#, *—$W^1$—C(O)—C($R^{D5}R^{D6}$)—#, *—C($R^{D1}R^{D2}$)—C($R^{D3}R^{D4}$)—C(O)—#, *—$W^1$—C($R^{D3}R^{D4}$)—C(O)—#; wherein the * and # denote the attachment points of $X^1$ in Formula I;

$X^2$ may be selected from the group consisting of: *—C($R^{D1}R^{D2}$)—#, *—C($R^{D1}R^{D2}$)—C($R^{D5}R^{D6}$)—#, *—C($R^{C1}$)=C($R^{C2}$)—#, *—N=C(RC2)—#, *—C($R^{C1}$)=N—#, *—$W^1$—C($R^{D5}R^{D6}$)—#, *—$W^1$—C(O)—#, *—C($R^{D1}R^{D2}$)—C(O)—#, *—C($R^{D1}R^{D2}$)—C($R^{D3}R^{D4}$)—C($R^{D5}R^{D6}$)—#, *—$W^1$—C($R^{D3}R^{D4}$)—C($R^{D5}R^{D6}$)—#, *—$W^1$—C(O)—C($R^{D5}R^{D6}$)—#, *—C($R^{D1}R^{D2}$)—C($R^{D3}R^{D4}$)—C(O)—#, *—$W^1$—C($R^{D3}R^{D4}$)—C(O)—#, *—C($R^{D1}R^{D2}$)—$W^2$—C($R^{D5}R^{D6}$)—#, *—C($R^{D1}R^{D2}$)—$W^2$—C(O)—#; wherein the * and # indicate the attachment points of $X^2$ in Formula II;

Y may be selected from CH or N;

$B^1$ or $B^2$ rings may each optionally be substituted by one or more fluorine atoms on any of the available carbon atoms;

$W^1$ may be selected from the group consisting of: O or N($R^{N1}$);

$W^2$ may be selected from the group consisting of: O or N($R^{N2}$);

A may be a ring selected from the group consisting of: phenyl, a 5-6 membered heteroaryl having 1, 2 or 3 heteroatoms each selected from S, N or O, and a 4-7 membered heterocycle having 1, 2 or 3 heteroatoms each selected from N or O;

$R^{A1}$ may be selected, independently for each occurrence, from the group consisting of: hydrogen, hydroxyl, cyano, halogen, $C_{1-4}$alkyl or $C_{1-3}$alkoxy; wherein $C_{1-4}$alkyl, or $C_{1-3}$alkoxy may be optionally substituted by one or more fluorines;

n may be 1 or 2;

$R^{A2}$ may be selected from the group consisting of: hydrogen, $R^iR^jN$—, heterocyclyl, heterocyclyloxy, heterocyclyl-(NR$^a$)—; wherein said heterocyclyl may optionally be substituted by one or more substituents selected from $R^g$ and wherein if said heterocyclyl contains a —NH moiety that nitrogen may optionally be substituted by one or more groups $R^h$; or $R^{A2}$ may be selected from the group consisting of: $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— (wherein w is 0, 1 or 2), $C_{1-6}$alkyl-N(R$^a$)—, $C_{1-6}$alkyl-N(R$^a$)-carbonyl-, $C_{1-6}$alkylcarbonyl-N(R$^a$)—, $C_{1-6}$alkyl-N(R$^a$)-carbonyl-N(R$^a$)—, $C_{1-6}$alkyl-N(R$^a$)—SO$_2$—, $C_{1-6}$alkyl-SO$_2$—N(R$^a$)—, $C_{1-6}$alkoxycarbonyl-N(R$^a$)—, $C_{1-6}$alkylcarbonyl-N(R$^a$)—$C_{1-6}$alkyl-, $C_{1-6}$alkyl-N(R$^a$)-carbonyl-$C_{1-6}$alkyl-, $C_{1-6}$alkoxyC$_{1-6}$alkyl-; wherein $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— (wherein w is 0, 1 or 2), $C_{1-6}$alkyl-N(R$^a$)—, $C_{1-6}$alkyl-N(R$^a$)-carbonyl-, $C_{1-6}$alkylcarbonyl-N(R$^a$)—, $C_{1-6}$alkyl-N(R$^a$)-carbonyl-N(R$^a$)—, $C_{1-6}$alkyl-N(R$^a$)—SO$_2$—, $C_{1-6}$alkyl-SO$_2$—N(R$^a$)—, $C_{1-6}$alkoxycarbonyl-N(R$^a$)—, $C_{1-6}$alkylcarbonyl-N(R$^a$)C$_{1-6}$alkyl-, $C_{1-6}$alkyl-N(R$^a$)-carbonyl-$C_{1-6}$alkyl-, $C_{1-6}$alkoxy-$C_{1-6}$alkyl may optionally be substituted by R$^P$, phenyl, phenoxy, heteroaryl, heteroaryloxy, heteroaryl-(NR$^a$)—, heterocyclyl, heterocyclyloxy or heterocyclyl-N(R$^a$)—; wherein said heteroaryl or phenyl may optionally be substituted with one or more substituents selected from R$^f$; wherein said heterocyclyl may optionally be substituted by one or more substituents selected from R$^g$; and wherein if said heterocyclyl contains a —NH moiety that nitrogen may optionally be substituted by one or more groups R$^h$;

$R^{D1}$ and $R^{D2}$ may be each independently selected from the group consisting of: hydrogen, fluorine, hydroxyl, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano or hydroxyl;

$R^{D3}$ and $R^{D4}$ may be each independently selected from the group consisting of: hydrogen, fluorine, hydroxyl, cyano, $C_{1-3}$alkyl or $C_{1-3}$alkoxy; wherein the $C_{1-3}$ alkyl and $C_{1-3}$ alkoxy may optionally be substituted by one or more fluorine atoms or a group selected from cyano, hydroxyl or N(R$^a$R$^b$);

$R^{D5}$ and $R^{D6}$ may be each independently selected from the group consisting of: hydrogen, fluorine, hydroxyl, cyano, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano, hydroxyl or N(R$^a$R$^b$), $R^{C1}$ may be selected from the group consisting of: hydrogen, halogen, $C_{1-2}$alkyl or $C_{1-2}$alkoxy; wherein the $C_{1-2}$alkyl or $C_{1-2}$alkoxy may optionally be substituted by one or more fluorine atoms;

$R^{C2}$ may be selected from the group consisting of: hydrogen, halogen, hydroxyl, cyano, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano, hydroxyl or N(R$^a$R$^b$);

$R^{N1}$ may be selected from the group consisting of: hydrogen or $C_{1-2}$alkyl;

$R^{N2}$ may be selected from the group consisting of: hydrogen, $C_{1-3}$alkyl or $C_{1-2}$alkylcarbonyl; wherein the $C_{1-3}$alkyl and $C_{1-2}$alkylcarbonyl may optionally be substituted by one or more fluorine atoms or a group selected from cyano, hydroxyl or N(R$^a$R$^b$);

$R^a$ and $R^b$ may be independently selected, for each occurrence, from the group consisting of: hydrogen and $C_{1-3}$alkyl; wherein $C_{1-3}$alkyl may optionally be substituted by one or more substituents selected from: fluorine, cyano, oxo and hydroxyl;

or $R^a$ and $R^b$, together with the nitrogen to which they are attached, may form a 4-6 membered heterocyclic ring which may have an additional heteroatom selected from O, S, or N; and wherein the 4-6 membered heterocyclic ring may optionally be substituted on carbon by one or more substituents selected from the group consisting of: fluorine, cyano, oxo or hydroxyl;

$R^f$ may be independently selected, for each occurrence, from the group consisting of: R$^P$, hydrogen, $C_{1-6}$alkyl, $C_{3-6}$cycloalkyl, $C_{2-6}$alkenyl, $C_{2-6}$alkynyl, $C_{3-6}$cycloalkyl, $C_{1-6}$alkoxy, $C_{1-6}$alkyl-S(O)$_w$— (wherein w is 0, 1 or 2), $C_{1-6}$alkylcarbonyl-N(R$^a$)—; $C_{1-6}$alkoxycarbonyl-N(R$^a$)—; and wherein $C_{1-6}$alkyl, $C_{3-6}$cycloalkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N(R$^a$)—, $C_{1-6}$alkoxycarbonyl-N(R$^a$)— may be optionally substituted by one or more substituents selected from R$^P$;

$R^g$ may be independently selected for each occurrence from the group consisting of: R$^P$, hydrogen, oxo, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$— (wherein w is 0, 1 or 2), $C_{1-6}$alkylcarbonyl-N(R$^a$)—, $C_{1-6}$alkoxycarbonyl-N(R$^a$)—; wherein $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N(R$^a$)—, $C_{1-6}$alkoxycarbonyl-N(R$^a$)— may be optionally substituted by one or more substituents selected from R$^P$;

$R^h$ may be independently selected for each occurrence from the group consisting of: hydrogen, $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkoxycarbonyl-, R$^i$R$^j$N-carbonyl-, R$^i$R$^j$N—SO$_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkylcarbonyl- may optionally be substituted by one or more substituents selected from R$^P$;

$R^i$ and $R^j$, may be selected independently for each occurrence from the group consisting of: hydrogen, $C_{1-4}$alkyl and $C_{3-6}$cycloalkyl; wherein $C_{1-4}$alkyl and $C_{3-6}$cycloalkyl may be optionally substituted by one or more substituents selected from fluorine, hydroxyl, cyano, R$^a$R$^b$N—, R$^a$R$^b$N-carbonyl-, $C_{1-3}$alkoxy;

or $R^i$ and $R^j$ taken together with the nitrogen to which they are attached may form a 4-7 membered heterocyclic ring which may have an additional heteroatom selected from O, S, or N, optionally substituted on carbon by one or more substituents selected from the group consisting of: fluorine, hydroxyl, oxo, cyano, $C_{1-6}$alkyl, $C_{1-6}$alkoxy, R$^a$R$^b$N—, R$^a$R$^b$N—SO$_2$—, R$^a$R$^b$N-carbonyl-; and wherein said $C_{1-6}$alkyl or $C_{1-6}$alkoxy may optionally be substituted by fluorine, hydroxyl or cyano; and optionally substituted on nitrogen by one or more substituents selected from the group consisting of: $C_{1-6}$alkyl, R$^a$R$^b$N-carbonyl-; and wherein said $C_{1-6}$alkyl may be optionally substituted by fluorine, hydroxyl, cyano;

$R^P$ may be independently selected, for each occurrence, from the group consisting of: halogen, hydroxyl, cyano, $C_{1-6}$alkoxy, R$^i$R$^j$N—, R$^i$R$^j$N-carbonyl-, R$^i$R$^j$N—SO$_2$—, R$^i$R$^j$N-carbonyl-N(R$^a$)—;

and pharmaceutically acceptable salts, stereoisomers, esters and prodrugs thereof.

In some embodiments, $X^1$ may be selected from the group consisting of: *—C(R$^{D1}$R$^{D2}$)—C(R$^{D5}$R$^{D6}$)—#, *—C(R$^{C1}$)=C(R$^{C2}$)—#, *—O—C(R$^{D5}$R$^{D6}$)—#, *—N(R$^{N1}$)—C(R$^{D5}$R$^{D6}$)—#, *—C(R$^{D1}$R$^{D2}$)—C(O)—#, *—O—C(R$^{D3}$R$^{D4}$)—C(R$^{D5}$R$^{D6}$)—# and *—N(R$^{N1}$)—C(R$^{D3}$R$^{D4}$)—C(R$^{D5}$R$^{D6}$)—#; wherein the * and # indicate the attachment points of $X^1$ as indicated in Formula I. Exemplary $X^1$ moieties may be selected from the group consisting of: *—CH$_2$CH$_2$—# and *—CH=CH—#; wherein the * and # indicate the attachment points of $X^1$ as indicated in Formula I.

In some embodiments, $X^2$ may be selected from the group consisting of: *—C(R$^{D1}$R$^{D2}$)—C(R$^{D5}$R$^{D6}$)—#, *—C $(R^{C1})=C(R^{C2})-^{\#}$, $*-N=C(R^{C2})-^{\#}$, $*-O-C(R^{D5}R^{D6})-^{\#}$, $*-N(R^{N1})-C(R^{D5}R^{D6})-^{\#}$, $*-O-C(R^{D3}R^{D4})-C(R^{D5}R^{D6})-^{\#}$ and $*-N(R^{N1})-C(R^{D3}R^{D4})-C(R^{D5}R^{D6})-^{\#}$; wherein the * and # indicate the attachment points of $X^2$ as indicated in Formula II. Exemplary $X^2$ moieties may be selected from the group consisting of: $*-CH_2CH_2-^{\#}$, $*-CH=CH-^{\#}$, $*-O-CH_2-^{\#}$, $*-NH-CH_2-^{\#}$ and $*-O-CH_2-CH_2-^{\#}$; wherein the * and # indicate the attachment points of $X^2$ as indicated in Formula II.

In one embodiment, $R^{D1}$, $R^{D2}$, $R^{C1}$ and $R^{N1}$ be independently selected for each occurrence from the group consisting of hydrogen and methyl. For example, $R^{D1}$, $R^{D2}$, $R^{C1}$ and $R^{N1}$ may be hydrogen.

In certain embodiments, $R^{D3}$, $R^{D4}$, $R^{D5}$ and $R^{D6}$ may be independently selected for each occurrence from the group consisting hydrogen, fluorine, cyano, or $C_{1-2}$alkyl. For example, $R^{D3}$, $R^{D4}$, $R^{D5}$ and $R^{D6}$ may be hydrogen.

In an embodiment, $R^{C2}$ may be selected from the group consisting of hydrogen, halogen, cyano or $C_{1-2}$alkyl. For example, $R^{C2}$ may be hydrogen.

In an embodiment, $R^{N2}$ may be selected from the group consisting of hydrogen and $C_{1-2}$alkyl. For example, $R^{N2}$ may be hydrogen.

In some embodiments, Y may be N.

Provided herein, for example, are tricyclic compounds represented by formulas Ia, Ib, Ic, IIa, IIb, IIc, IId and IIe:

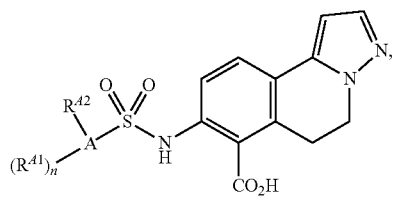
Ia

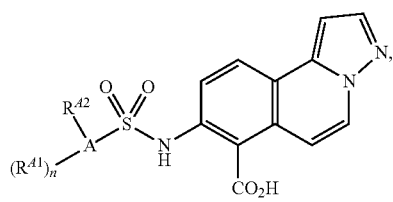
Ib

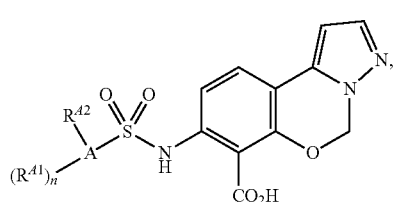
Ic

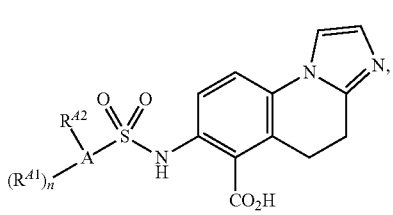
IIa

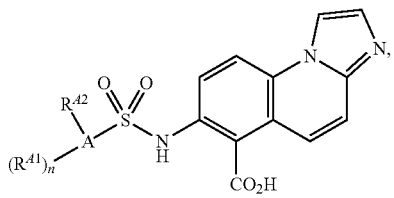
IIb

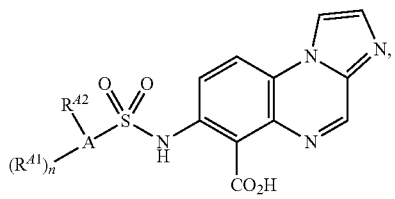
IIc

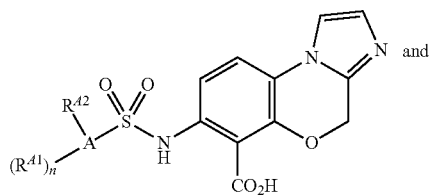
IId and

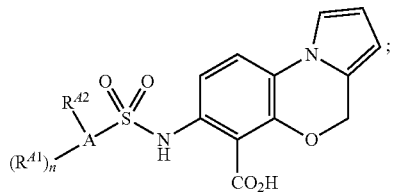
IIe;

wherein A, $R^{A1}$, n and $R^{A2}$ are defined above. For example, A may be phenyl.

Also provided herein is a compound represented by Formula III, Formula IV and Formula V:

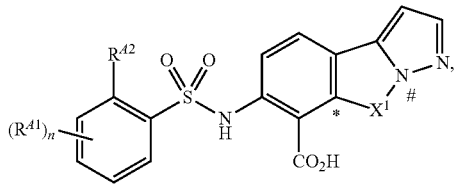
Formula III

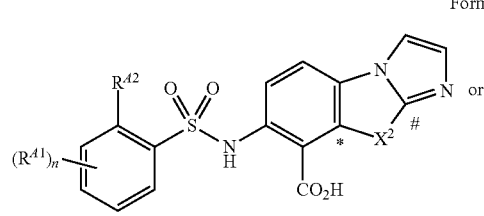
Formula IV or

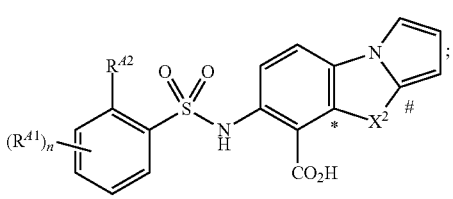
Formula V;

wherein $X^1$ may be selected from the group consisting of: *—C($R^{D1}R^{D2}$)—#, *—C($R^{D1}R^{D2}$)—C($R^{D5}R^{D6}$)—#, *—C($R^{C1}$)=C($R^{C2}$)—#, *—N=C($R^{C2}$)—#, *—$W^1$—C($R^{D5}R^{D6}$)—#, *—$W^1$—C(O)—#, *—C($R^{D1}R^{D2}$)—C(O)—#, *—C($R^{D1}R^{D2}$)—C($R^{D3}R^{D4}$)—C($R^{D5}R^{D6}$)—#, *—$W^1$—C($R^{D3}R^{D4}$)—C($R^{D5}R^{D6}$)—#, *—$W^1$—C(O)—C($R^{D5}R^{D6}$)—#, *—C($R^{D1}R^{D2}$)—C($R^{D3}R^{D4}$)—C(O)—#, *—$W^1$—C($R^{D3}R^{D4}$)—C(O)—#; wherein the * and # denote the attachment points of $X^1$ in Formula I;

$X^2$ may be selected from the group consisting of: *—C($R^{D1}R^{D2}$)—#, *—C($R^{D1}R^{D2}$)—C($R^{D5}R^{D6}$)—#, *—C($R^{C1}$)=C($R^{C2}$)—#, *—N=C(R$C^2$)—#, *—C($R^{C1}$)=N—#, *—$W^1$—C($R^{D5}R^{D6}$)—#, *—$W^1$—C(O)—#, *—C($R^{D1}R^{D2}$)—C(O)—#, *—C($R^{D1}R^{D2}$)—C($R^{D3}R^{D4}$)—C($R^{D5}R^{D6}$)—#, *—$W^1$—C($R^{D3}R^{D4}$)—C($R^{D5}R^{D6}$)—#, *—$W^1$—C(O)—C($R^{D5}R^{D6}$)—#, *—C($R^{D1}R^{D2}$)—C($R^{D3}R^{D4}$)—C(O)—#, *—$W^1$—C($R^{D3}R^{D4}$)—C(O)—#, *—C($R^{D1}R^{D2}$)—$W^2$—C($R^{D5}R^{D6}$)—#, *—C($R^{D1}R^{D2}$)—$W^2$—C(O)—#; wherein the * and # indicate the attachment points of $X^2$ in Formula II;

$W^1$ may be selected from the group consisting of: O or N($R^{N1}$);

$W^2$ may be selected from the group consisting of: O or N($R^{N2}$);

$R^{A1}$ may be selected, independently for each occurrence, from the group consisting of: hydrogen, hydroxyl, cyano, halogen, $C_{1-4}$alkyl or $C_{1-3}$alkoxy; wherein $C_{1-4}$alkyl, or $C_{1-3}$alkoxy may be optionally substituted by one or more fluorines;

n may be 1 or 2;

$R^{A2}$ may be selected from the group consisting of: hydrogen, $R^i R^j N$—, heterocyclyl, heterocyclyloxy, heterocyclyl-(N$R^a$)—; wherein said heterocyclyl may optionally be substituted by one or more substituents selected from $R^g$ and wherein if said heterocyclyl contains a —NH moiety that nitrogen may optionally be substituted by one or more groups $R^h$; or $R^{A2}$ may be selected from the group consisting of: $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— (wherein w is 0, 1 or 2), $C_{1-6}$alkyl-N($R^a$)—, $C_{1-6}$alkyl-N($R^a$)-carbonyl-, $C_{1-6}$alkyl-carbonyl-N($R^a$)—, $C_{1-6}$alkyl-N($R^a$)-carbonyl-N($R^a$)—, $C_{1-6}$alkyl-N($R^a$)—SO$_2$—, $C_{1-6}$alkyl-SO$_2$—N($R^a$)—, $C_{1-6}$alkoxycarbonyl-N($R^a$)—, $C_{1-6}$alkylcarbonyl-N($R^a$)—$C_{1-6}$alkyl-, $C_{1-6}$alkyl-N($R^a$)-carbonyl-$C_{1-6}$alkyl-, $C_{1-6}$alkoxy$C_{1-6}$alkyl-; wherein $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$—, $C_{1-6}$alkyl-N($R^a$)—, $C_{1-6}$alkyl-N($R^a$)-carbonyl-, $C_{1-6}$alkyl-carbonyl-N($R^a$)—, $C_{1-6}$alkyl-N($R^a$)-carbonyl-N($R^a$)—, $C_{1-6}$alkyl-N($R^a$)—SO$_2$—, $C_{1-6}$alkyl-SO$_2$—N($R^a$)—, $C_{1-6}$alkoxycarbonyl-N($R^a$)—, $C_{1-6}$alkylcarbonyl-N($R^a$)$C_{1-6}$alkyl-, $C_{1-6}$alkyl-N($R^a$)-carbonyl-$C_{1-6}$alkyl-, $C_{1-6}$alkoxy-$C_{1-6}$alkyl may optionally be substituted by $R^P$, phenyl, phenoxy, heteroaryl, heteroaryloxy, heteroaryl-(N$R^a$)—, heterocyclyl, heterocyclyloxy or heterocyclyl-N($R^a$)—; wherein said heteroaryl or phenyl may optionally be substituted with one or more substituents selected from $R^f$; wherein said heterocyclyl may optionally be substituted by one or more substituents selected from $R^g$; and wherein if said heterocyclyl contains a —NH moiety that nitrogen may optionally be substituted by one or more groups $R^h$;

$R^{D1}$ and $R^{D2}$ may be each independently selected from the group consisting of: hydrogen, fluorine, hydroxyl, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano or hydroxyl;

$R^{D3}$ and $R^{D4}$ may be each independently selected from the group consisting of: hydrogen, fluorine, hydroxyl, cyano, $C_{1-3}$alkyl or $C_{1-3}$alkoxy; wherein the $C_{1-3}$ alkyl and $C_{1-3}$ alkoxy may optionally be substituted by one or more fluorine atoms or a group selected from cyano, hydroxyl or N($R^a R^b$);

$R^{D5}$ and $R^{D6}$ may be each independently selected from the group consisting of: hydrogen, fluorine, hydroxyl, cyano, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano, hydroxyl or N($R^a R^b$), $R^{C1}$ may be selected from the group consisting of: hydrogen, halogen, $C_{1-2}$alkyl or $C_{1-2}$alkoxy; wherein the $C_{1-2}$alkyl or $C_{1-2}$alkoxy may optionally be substituted by one or more fluorine atoms;

$R^{C2}$ may be selected from the group consisting of: hydrogen, halogen, hydroxyl, cyano, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano, hydroxyl or N($R^a R^b$);

$R^{N1}$ may be selected from the group consisting of: hydrogen or $C_{1-2}$alkyl;

$R^{N2}$ may be selected from the group consisting of: hydrogen, $C_{1-3}$alkyl or $C_{1-2}$alkylcarbonyl; wherein the $C_{1-3}$alkyl and $C_{1-2}$alkylcarbonyl may optionally be substituted by one or more fluorine atoms or a group selected from cyano, hydroxyl or N($R^a R^b$);

$R^a$ and $R^b$ may be independently selected, for each occurrence, from the group consisting of: hydrogen and $C_{1-3}$alkyl; wherein $C_{1-3}$alkyl may optionally be substituted by one or more substituents selected from: fluorine, cyano, oxo and hydroxyl;

or $R^a$ and $R^b$, together with the nitrogen to which they are attached, may form a 4-6 membered heterocyclic ring which may have an additional heteroatom selected from O, S, or N; and wherein the 4-6 membered heterocyclic ring may optionally be substituted on carbon by one or more substituents selected from the group consisting of: fluorine, cyano, oxo or hydroxyl;

$R^f$ may be independently selected, for each occurrence, from the group consisting of: $R^P$, hydrogen, $C_{1-6}$alkyl, $C_{3-6}$cycloalkyl, $C_{2-6}$alkenyl, $C_{2-6}$alkynyl, $C_{3-6}$cycloalkyl, $C_{1-6}$alkoxy, $C_{1-6}$alkyl-S(O)$_w$— (wherein w is 0, 1 or 2), $C_{1-6}$alkylcarbonyl-N($R^a$)—; $C_{1-6}$alkoxycarbonyl-N($R^a$)—; and wherein $C_{1-6}$alkyl, $C_{3-6}$cycloalkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N($R^a$)—, $C_{1-6}$alkoxycarbonyl-N($R^a$)— may be optionally substituted by one or more substituents selected from $R^P$;

$R^g$ may be independently selected for each occurrence from the group consisting of: $R^P$, hydrogen, oxo, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$— (wherein w is 0, 1 or 2), $C_{1-6}$alkylcarbonyl-N($R^a$)—, $C_{1-6}$alkoxycarbonyl-N($R^a$)—; wherein $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N($R^a$)—, $C_{1-6}$alkoxycarbonyl-N($R^a$)— may be optionally substituted by one or more substituents selected from $R^P$;

$R^h$ may be independently selected for each occurrence from the group consisting of: hydrogen, $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkoxycarbonyl-, $R^i R^j N$-carbonyl-, $R^i R^j N$—SO$_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkylcarbonyl- may optionally be substituted by one or more substituents selected from $R^P$;

$R^i$ and $R^j$, may be selected independently for each occurrence from the group consisting of: hydrogen, $C_{1-4}$alkyl and $C_{3-6}$cycloalkyl; wherein $C_{1-4}$alkyl and $C_{3-6}$cycloalkyl may be optionally substituted by one or more substituents selected from fluorine, hydroxyl, cyano, $R^aR^bN—$, $R^aR^bN$-carbonyl-, $C_{1-3}$alkoxy;

or $R^i$ and $R^j$ taken together with the nitrogen to which they are attached may form a 4-7 membered heterocyclic ring which may have an additional heteroatom selected from O, S, or N, optionally substituted on carbon by one or more substituents selected from the group consisting of: fluorine, hydroxyl, oxo, cyano, $C_{1-6}$alkyl, $C_{1-6}$alkoxy, $R^aR^bN—$, $R^aR^bN—SO_2—$, $R^aR^bN$-carbonyl-; and wherein said $C_{1-6}$alkyl or $C_{1-6}$alkoxy may optionally be substituted by fluorine, hydroxyl or cyano; and optionally substituted on nitrogen by one or more substituents selected from the group consisting of: $C_{1-6}$alkyl, $R^aR^bN$-carbonyl-; and wherein said $C_{1-6}$alkyl may be optionally substituted by fluorine, hydroxyl, cyano;

$R^P$ may be independently selected, for each occurrence, from the group consisting of: halogen, hydroxyl, cyano, $C_{1-6}$alkoxy, $R^iR^jN—$, $R^iR^jN$-carbonyl-, $R^iR^jN—SO_2—$, $R^iR^jN$-carbonyl-N($R^a$)—;

and pharmaceutically acceptable salts, stereoisomers, esters and prodrugs thereof.

In certain embodiments, $R^{41}$ of the tricyclic compounds of Formula III, Formula IV and Formula V may be selected from the group consisting of hydrogen, halogen, $C_{1-2}$alkyl, $C_{1-2}$alkoxy; wherein $C_{1-2}$alkyl may optionally be substituted by one or more fluorines. For example, $R^{41}$ may be hydrogen or fluorine.

In another embodiment, $R^{42}$ of the tricyclic compounds of Formula III, Formula IV and Formula V may be selected from the group consisting hydrogen, $R^iR^jN$, heterocyclyl, $C_{1-6}$alkyl, $C_{3-6}$alkenyl, $C_{3-6}$cycloalkyl, $C_{1-6}$alkoxy; wherein said heterocyclyl may optionally be substituted by one or more groups $R^g$, and wherein if said heterocyclyl contains a —NH moiety, that nitrogen may optionally be substituted by on or more groups $R^h$; and wherein said $C_{1-6}$alkyl, $C_{3-6}$alkenyl, $C_{3-6}$cycloalkyl and $C_{1-6}$alkoxy may optionally be substituted by one or more groups $R^P$. For example, $R^{42}$ may be selected from the group consisting of 3-(N,N-diethylamino) propyl, 3-(pyrrolidin-1-yl)propyl, (Z)-3-(N,N-diethylamino) prop-1-enyl, (Z)-3-(azetidin-1-yl)prop-1-enyl and (Z)-3-(pyrrolidin-1-yl)prop-1-enyl.

Also provided herein are compounds that may be selected from the group consisting of: 8-[2-((Z)-3-diethylaminoprop-1-enyl)-4-fluorobenzenesulfonylamino]-pyrazolo[5,1-a]isoquinoline-7-carboxylic acid; 7-[2-((Z)-3-diethylaminoprop-1-enyl)-4-fluorobenzenesulfonylamino]-4H-benzo[b] pyrrolo[1,2-d][1,4]oxazine-6-carboxylic acid; 8-[2-((Z)-3-diethylaminoprop-1-enyl)-4-fluorobenzenesulfonylamino]-5,6-dihydropyrazolo[5,1-a]isoquinoline-7-carboxylic acid; 7-[2-((Z)-3-diethylaminoprop-1-enyl)-4-fluorobenzenesulfonylamino]-4H-5-oxa-3,9b-diazacyclopenta[a]naphthalene-6-carboxylic acid and pharmaceutically acceptable salts, stereoisomers, esters and prodrugs thereof.

Procedures for making compounds described herein are provided below with reference to Schemes 1-7. In the reactions described below, it may be necessary to protect reactive functional groups (such as hydroxyl, amino, thio or carboxyl groups) to avoid their unwanted participation in the reactions. The incorporation of such groups, and the methods required to introduce and remove them are known to those skilled in the art (for example, see Greene, Wuts, *Protective Groups in Organic Synthesis*. 2nd Ed. (1999)). The deprotection step may be the final step in the synthesis such that the removal of protecting groups affords compounds of Formula I and II, as disclosed herein, or as exemplified in, for example, General formula I or II, below. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

A general strategy used to prepare tricyclic compounds of General formula I is depicted in Scheme 1. In Scheme 1, the group G' is a suitably protected carboxylic acid, such as a methyl- or tert-butyl carboxylate or is a functional group that may be readily converted into a carboxylic acid, such as a nitrile or aldehyde. The group G is a sulfonamide group, or a functional group that may be subsequently converted into a sulfonamide group such as a suitably protected aniline. The tricyclic system may be assembled by first attaching an appropriately substituted pyrazole or pyrrole intermediate 1B' to the substituted phenyl ring 1A to give the intermediate 1B. The linker X' may then be formed by an intramolecular reaction between the groups $R^2$ and $R^4$ to give the intermediate 1C. Compounds of Formula I can be prepared from intermediate 1C by removal of any protecting groups. Alternatively, further modifications may be made to 1C, such as modifications at G, before the removal of any protecting groups to give compounds of General formula I. Specific steps in the synthetic process are described in more detail below.

SCHEME 1

In Scheme 1, Step (i), compounds of structure 1A may be coupled with compounds of structure 1B' under a range of conditions known to those skilled in the art to give compounds of structure 1B. It will be recognized by those skilled the art that several steps may be required to prepare the intermediates and that protecting groups may be required.

For example, compounds of structure 1A in which R¹ is an appropriate group (such as a halide or a triflate) may be coupled with an appropriately substituted pyrazole or pyrrole 1B' in which R³ is a boronic acid or ester, in the presence of a palladium catalyst (such as palladium acetate, palladium chloride dppf or tris-(dibenzylideneacetone)dipalladium) optionally in the presence of a phosphine (such as triphenyl phosphine or tri-tert-butylphosphonium tetrafluoroborate) and a base (such as cesium carbonate) in a solvent (such as THF, dioxane or water or mixtures thereof) at a temperature between room temperature and the reflux temperature of the solvent or by irradiation in the microwave at a temperature between 120 and 180° C.

Alternatively, compounds of structure 1A, in which R¹ is an appropriate group (such as a halide or a triflate), may be coupled with an appropriately substituted pyrazole or pyrrole 1B', in which R³ is a trialkyl stannane, in the presence of a palladium catalyst (such as palladium acetate, palladium chloride dppf or tris-(dibenzylideneacetone)dipalladium) optionally in the presence of a phosphine (such as triphenyl phosphine or tri-tert-butylphosphonium tetrafluoroborate) and a base (such as cesium carbonate) in a solvent (such as THF or dioxane) at a temperature between room temperature and the reflux temperature of the solvent or by irradiation in the microwave at a temperature between 120 and 180° C.

Alternatively, compounds of structure 1A, in which R1 is a halide (such as a bromide or iodide), may be coupled with a pyrrole of structure 1B', in which Y is carbon and R³ is H, in the presence of an oxidising agent (such as oxygen or phenyl iodosoacetate) in the presence of a palladium catalyst (such as palladium acetate) in a solvent (such as acetic acid) at a temperature between room temperature and the reflux temperature of the solvent.

Compounds of structure 1B, in which Y is N, may alternatively be prepared according to Scheme 2, in which the pyrazole ring is prepared by reacting an appropriately substituted hydrazine with 1,3-dicarbonyl compound or equivalent.

SCHEME 2

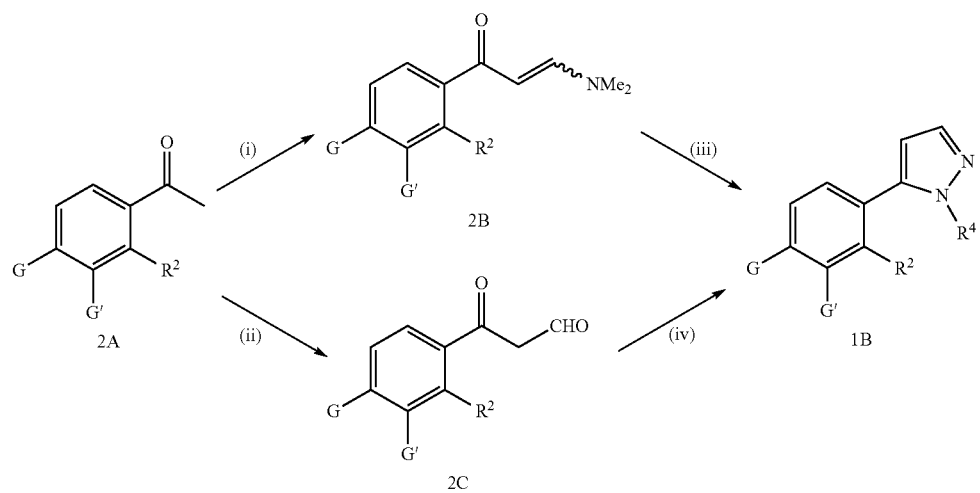

chloride dppf or tris-(dibenzylideneacetone)dipalladium) optionally in the presence of a phosphine (such as triphenyl phosphine or tri-tert-butylphosphonium tetrafluoroborate) and a base (such as cesium carbonate) in a solvent (such as THF or dioxane) at a temperature between room temperature and the reflux temperature of the solvent, or by irradiation in the microwave at a temperature between 120 and 180° C.

Alternatively, compounds of structure 1A, in which R¹ is a boronic acid or ester, may be coupled with compounds of structure 1B', in which R³ is a halide (such as a bromide of iodide), in the presence of a palladium catalyst (such as palladium acetate, palladium chloride dppf or tris-(dibenzylideneacetone)dipalladium), optionally in the presence of a phosphine (such as triphenyl phosphine or tri-tert-butylphosphonium tetrafluoroborate) and a base (such as cesium carbonate) in a solvent (such as THF, dioxane or water or mixtures thereof) at a temperature between room temperature and the reflux temperature of the solvent, or by irradiation in the microwave at a temperature between 120 and 180° C.

Alternatively, compounds of structure 1A, in which R¹ is a trialkyl stannane, may be coupled with compounds of structure 1B', in which R³ is a halide (such as a bromide or iodide), in the presence of a palladium catalyst (such as palladium acetate, palladium chloride dppf or tris-(dibenzylideneacetone)dipalladium), optionally in the presence of a phosphine In Scheme 2, Step (i), compounds of structure 2A may be treated with N,N-dimethylformamide dimethyl acetal or Bredereck's reagent (tert-butoxy-bis(N,N-dimethylamino)methane), optionally in a solvent (such as DCM or toluene) at a temperature between room temperature and the reflux temperature of the solvent to give compounds of structure 2B.

Alternatively, in Scheme 2, Step (ii), compounds of structure 2A may be treated with a base (such as sodium hydride or lithium diisopropylamide) in a solvent (such as THF) followed by treatment with an alkyl formate (such as methyl formate or ethyl formate) at a temperature between room temperature and the reflux temperature of the solvent to give compounds of structure 2C.

In Scheme 2, Step (iii) or Step (iv), compounds of structure 2B or 2C may be converted to compounds of structure 1B by reaction with hydrazine hydrate or an appropriately substituted hydrazine (R⁴NHNH₂) in a solvent (such as DCM, methanol, ethanol or toluene) optionally in the presence of acetic acid and sodium acetate or hydrochloric acid.

In Scheme 1, Step (ii) the groups R² and R⁴ of compound 1B can be coupled together to give the group X'. R² or R⁴ may have been masked by protecting groups during the earlier steps, and may require deprotection before the group X' can be formed. For example, if R² is a nitro group, that group may be reduced, for example using hydrogen in the presence of a suitable catalyst (such as palladium on a solid support, such as carbon); or by treatment with an inorganic reducing agent (such as tin (II) chloride in DMF) to give an amino group. For example, if $R^2$ or $R^4$ is a hydroxyalkyl group, that group may be treated with an oxidising agent (such as Jones reagent or manganese dioxide) to give an aldehyde; or with a different oxidising agent (such as potassium permanganate) to give a carboxylic acid. For example, if $R^2$ or $R^4$ is an aldehyde, that group may be treated with an oxidising agent (such as potassium permanganate) to give a carboxylic acid or with a reducing agent (such as sodium borohydride) to give an alcohol. For example, if $R^2$ or $R^4$ is a ketone, that group may be treated with a reducing agent (such as sodium borohydride) to give a secondary alcohol. For example, if $R^2$ or $R^4$ is a carboxylic acid or ester, that group may be treated with a reducing agent (such as lithium aluminium hydride) to give an alcohol. For example, if $R^2$ or $R^4$ is an alkene group, that group may be treated with a borane (such as 9-borobicyclononane) followed by oxidation with, for example, hydrogen peroxide, to give a primary or secondary alcohol.

The formation of the X' linker may be carried out in a number of ways known to those skilled in the art. Several steps may be necessary to generate the required intermediates and protecting groups may be required.

In Scheme 1, Step (ii), if $R^2$ is an alkyl group attached to a leaving group, for example —C($R^{D1}R^{D2}$)-L, —C($R^{D1}R^{D2}$)—C($R^{D3}R^{D4}$)-L or —C($R^{D1}R^{D2}$)—C($R^{D3}R^{D4}$)—C($R^{D5}R^{D6}$)-L wherein L is a leaving group (such as a halogen, tosylate or mesylate) and $R^4$ is H, then 1B may be treated with a base (such as pyridine, potassium carbonate or sodium hydride) in a solvent (such as DCM, THF or toluene) at a temperature between room temperature and the reflux temperature of the solvent to give a compound of structure 1C, wherein X' is —C($R^{D1}R^{D2}$)—, —C($R^{D1}R^{D2}$)—C($R^{D3}R^{D4}$)— or —C($R^{D1}R^{D2}$)—C($R^{D3}R^{D4}$)—C($R^{D5}R^{D6}$)—.

Alternatively if $R^2$ is a hydroxyalkyl group, for example —C($R^{D1}R^{D2}$)—OH, —C($R^{D1}R^{D2}$)—C($R^{D3}R^{D4}$)—OH or —C($R^{D1}R^{D2}$)—C($R^{D3}R^{D4}$)—C($R^{D5}R^{D6}$)—OH and $R^4$ is H, then 1B may be treated with a dehydrating agent (such as diisopropyl azodicarboxylate) in the presence of a phosphine, (such as triphenylphosphine), to give a compound of structure 1C, wherein X' is —C($R^{D1}R^{D2}$)—, —C($R^{D1}R^{D2}$)—C($R^{D3}R^{D4}$)— or —C($R^{D1}R^{D2}$)—C($R^{D3}R^{D4}$)—C($R^{D5}R^{D6}$)—.

Alternatively, if $R^2$ is a vinyl group (—CH=$CH_2$) and $R^4$ is H, 1B may be treated with a peroxide (such as 3-chloroperbenzoic acid) optionally in the presence of a catalyst (such as N,N'-bis(3,5-di-tert-butylsalicylidene)-1,2-cyclohexanediamino manganese (III) chloride and N-methyl morpholine-N-oxide) in a solvent (such as DCM) at a temperature between room temperature and the reflux temperature of the solvent, to give a compound of structure 1C, wherein X' is —CH(OH)—$CH_2$—.

Compounds of structure 1C, in which X' is —CH(OH)—$CH_2$—, may be modified to provide further compounds of structure 1C. For example, by treatment with methane sulfonyl chloride and a base (such as triethylamine or pyridine) in a solvent (such as DCM) at a temperature between room temperature and the reflux temperature of the solvent to give compounds of structure 1C, wherein X' is —CH=CH—.

Additionally, compounds of structure 1C, in which X' is —CH=CH—, may be reduced to compounds in which X' is —$CH_2$—$CH_2$— by hydrogenation in the presence of a catalyst (such as palladium hydroxide on a solid support, such as carbon) in a solvent (such as dioxane) optionally in the presence of an acid (such as acetic acid) at a temperature between room temperature and 100° C. and a hydrogen pressure between atmospheric pressure and 100 bars.

Alternatively, compounds of structure 1B in which $R^2$ is a vinyl group (—CH=$CH_2$) and $R^4$ is an alkenyl group, (for example an allyl group, —$CH_2$—CH=$CH_2$), may undergo ring closing metathesis on treatment with a metal catalyst (such as Grubbs catalyst) in a solvent (such as DCM) at a temperature between room temperature and the reflux temperature of the solvent to give an intermediate in which X' is —CH=CH—$CH_2$—. Hydrogenation of this intermediate in the presence of a catalyst (such as palladium or palladium hydroxide on a solid support, such as carbon) in a solvent (such as ethanol or dioxane), optionally in the presence of an acid (such as acetic acid), at a temperature between room temperature and 50° C., and at a hydrogen pressure between atmospheric pressure and 5 bars, to give a compound of structure 1C in which X' is —$CH_2$—$CH_2$—$CH_2$—.

Alternatively, compounds of structure 1B, in which $R^2$ is $NH_2$ and $R^4$ is H, may be treated with an ortho ester (such as triethyl orthoformate or triethyl orthoacetate) in a solvent (such as ethanol) and in the presence of an acid (such as 4-toluenesulfonic acid), at a temperature between room temperature and the reflux temperature of the solvent to give a compound of structure 1C, in which X' is —N=C($R^{C2}$)—.

Alternatively, compounds of structure 1B, in which $R^2$ is an amino group (—NH($R^{N1}$)) and $R^4$ is H, may be treated with an aldehyde or ketone (such as formaldehyde or acetone) in a solvent (such as ethanol) and optionally in the presence of an acid catalyst (such as 4-toluenesulfonic acid) at a temperature between room temperature and the reflux temperature of the solvent, to give a compound of structure 1C in which X' is —N($R^{N1}$)—C($R^{D5}R^{D6}$)—.

Alternatively, compounds of structure 1B in which $R^2$ is an amino group (—NH($R^{N1}$)) and $R^4$ is an alkyl group substituted by a leaving group, such as —C($R^{D5}R^{D6}$)-L or —C($R^{D5}R^{D6}$)—C($R^{D3}R^{D4}$)-L, wherein L is a leaving group (such as a halide, mesylate or tosylate), may be treated with a base (such as pyridine or triethylamine) in a solvent (such as DCM or toluene) at a temperature between room temperature and the reflux temperature of the solvent, to give compounds of structure 1C in which X' is —N($R^{N1}$)—C($R^{D5}R^{D6}$)— or —N($R^{N1}$)—C($R^{D3}R^{D4}$)—C($R^{D5}R^{D6}$)—.

Alternatively, compounds of structure 1B, in which $R^2$ is an amino group (—NH($R^{N1}$)) and $R^4$ is H, may be converted to compounds of structure 1C, in which X' is —N($R^{N1}$)—C(O)—, by treatment with an appropriate reagent (such as phosgene, triphosgene or carbonyl-diimidazole) in a solvent (such as DCM or toluene) and in the presence of a base (such as pyridine or triethylamine), optionally in the presence of a catalyst (such as 4-dimethylaminopyridine) at a temperature between room temperature and the reflux temperature of the solvent.

Alternatively, compounds of structure 1B, in which $R^2$ is an amino group (—NH($R^{N1}$)) and $R^4$ is an alkyl group substituted by a carboxylic acid (—C($R^{D5}R^{D6}$)$CO_2H$), can be treated with a dehydrating agent (such as dicyclohexylcarbodiimide) to form 1C, where X' is —N($R^{N1}$)—C(O)—C($R^{D5}R^{D6}$)—.

Alternatively, if $R^2$ is an amino group (—NH($R^{N1}$)) and $R^4$ is an alkyl group substituted by a carboxylic acid (—C($R^{D5}R^{D6}$)$CO_2H$), the carboxylic acid can be converted to an activated ester (for example by treatment with HATU and a base such as diisopropylethylamine or pyridine, or by treatment with TBTU in the presence of N-methylmorpholine) and the activated ester can be treated with further base to form 1C in which X' is —N($R^{N1}$)—C(O)—C($R^{D5}R^{D6}$)—.

Alternatively, a compound of structure 1B, in which $R^2$ is an amino group (—NH($R^{N1}$)) and $R^4$ is an appropriate pyrazole or pyrrole protecting group (such as tetrahydropyran-2-yl), may be converted to other compounds of structure 1B in which $R^2$ is N($R^{N1}$)—C(O)—CH$_2$-L wherein L is a leaving group (such as a halide, for example a chloride or bromide), by treatment with a haloacetyl halide (such as chloroacetyl chloride or bromoacetyl bromide) in a solvent (such as THF or DCM) in the presence of a base (such as triethylamine or pyridine. The protecting group may be removed under conditions known to those skilled in the art (for example, if the protecting group is a tetrahydropyran-2-yl group, by treatment with hydrogen chloride in methanol) to give the intermediate of structure 1B in which $R^2$ is —N($R^{N1}$)—C(O)—CH$_2$-L and $R^4$ is H. Treatment of this intermediate with a base (such as pyridine, potassium carbonate or sodium hydride) in a solvent (such as DCM, THF or toluene), at a temperature between room temperature and the reflux temperature of the solvent, will give a compound of structure 1C wherein X' is —N($R^{N1}$)—C(O)—CH$_2$—.

Alternatively, compounds of structure 1B, in which $R^2$ is OH and $R^4$ is H, may be treated with an aldehyde or ketone (such as formaldehyde or acetone), in a solvent (such as ethanol or toluene), optionally in the presence of an acid catalyst (such as 4-toluenesulfonic acid), at a temperature between room temperature and the reflux temperature of the solvent, to give a compound of structure 1C in which X' is —O—C($R^{D5}R^{D6}$)—.

Alternatively, compounds of structure 1B in which $R^2$ is OH and $R^4$ is a hydroxyalkyl group, for example —C($R^{D5}R^{D6}$)—OH or —C($R^{D5}R^{D6}$)—C($R^{D3}R^{D4}$)—OH, may be treated with a dehydrating agent (such as diisopropyl azodicarboxylate), in the presence of a phosphine, (such as triphenylphosphine), to give a compound of structure 1C in which X' is —O—C($R^{D5}R^{D6}$)— or —O—C($R^{D3}R^{D4}$)—C($R^{D5}R^{D6}$)—.

Alternatively, compounds of structure 1B, in which $R^2$ is OH and $R^4$ is an alkyl group substituted by a leaving group, for example —C($R^{D5}R^{D6}$)-L or C($R^{D5}R^{D6}$)—C($R^{D3}R^{D4}$)-L, wherein L is a leaving group (such as a chloride or mesylate), may be treated with a base (such as potassium carbonate or sodium hydride) in a solvent (such as THF or DMF) at a temperature between room temperature and the reflux temperature of the solvent, to give a compound of structure 1C in which X' is —O—C($R^{D5}R^{D6}$)— or —O—C($R^{D3}R^{D4}$)—C($R^{D5}R^{D6}$)—.

Alternatively, compounds of structure 1B, in which $R^2$ is fluorine and $R^4$ is a hydroxyalkyl group, for example —C($R^{D5}R^{D6}$)—OH or —C($R^{D5}R^{D6}$)—C($R^{D3}R^{D4}$)—OH, may be treated with a base (such as sodium hydride or potassium tert-butoxide) in a solvent (such as THF or DMF) at a temperature between room temperature and the reflux temperature of the solvent, to give a compound of structure 1C in which X' is —O—C($R^{D5}R^{D6}$)— or —O—C($R^{D3}R^{D4}$)—C($R^{D5}R^{D6}$)—.

Alternatively, compounds of structure 1B, in which $R^2$ is OH and $R^4$ is H may be treated with an appropriate reagent (such as phosgene, triphosgene or carbonyl-diimidazole) in a solvent (such as THF, DCM or toluene) and in the presence of a base (such as potassium carbonate or sodium hydride) at a temperature between room temperature and the reflux temperature of the solvent to give compounds of structure 1C in which X' is —O—C(O)—.

Alternatively, compounds of structure 1B, in which $R^2$ is OH and $R^4$ is an alkyl group substituted by a carboxylic acid (—C($R^{D5}R^{D6}$)CO$_2$H), can be treated with a dehydrating agent (such as dicyclohexylcarbodiimide) to form 1C, where X' is —O—C(O)—C($R^{D5}R^{D6}$)—.

Alternatively, if $R^2$ is OH and $R^4$ is an alkyl group substituted by a carboxylic acid (—C($R^{D5}R^{D6}$)CO$_2$H), the carboxylic acid can be converted to an activated ester (for example by treatment with HATU and a base such as diisopropylethylamine or pyridine, or by treatment with TBTU in the presence of N-methylmorpholine) and the activated ester can be treated with further base to form 1C in which X' is —O—C(O)—C($R^{D5}R^{D6}$)—.

Alternatively, a compound of structure 1B, in which $R^2$ is OH and $R^4$ is an appropriate pyrazole or pyrrole protecting group (such as tetrahydropyran-2-yl), may be converted to other compounds of structure 1B, in which $R^2$ is O—C(O)—CH$_2$-L, wherein L is a leaving group (such as a halide, for example a chloride or bromide), by treatment with a haloacetyl halide (such as chloroacetyl chloride or bromoacetyl bromide) in a solvent (such as THF or DCM) in the presence of a base (such as triethylamine or pyridine). The protecting group may be removed under conditions known to those skilled in the art (for example, if the protecting group is a tetrahydropyran-2-yl group, by treatment with hydrogen chloride in methanol) to give the intermediate of structure 1B in which $R^2$ is —O—C(O)—CH$_2$-L and $R^4$ is H. Treatment of this intermediate with a base (such as pyridine, potassium carbonate or sodium hydride) in a solvent (such as DCM, THF or toluene) at a temperature between room temperature and the reflux temperature of the solvent, will give a compound of structure 1C wherein X' is —O—C(O)—CH$_2$—.

Alternatively, compounds of structure 1B, in which $R^2$ is an alkyl group attached to a carboxylic acid, for example —C($R^{D1}R^{D2}$)—CO$_2$H or —C($R^{D1}R^{D2}$)—C($R^{D3}R^{D4}$)—CO$_2$H and $R^4$ is H, can be treated with a dehydrating agent (such as dicyclohexylcarbodiimide) in a solvent (such as DCM) to give a compound of structure 1C in which X' is —C($R^{D1}R^{D2}$)—C(O)— or —C($R^{D1}R^{D2}$)—C($R^{D3}R^{D4}$)—C(O)—.

Alternatively, if $R^2$ is an alkyl group substituted by a carboxylic acid, for example —C($R^{D1}R^{D2}$)—CO$_2$H or —C($R^{D1}R^{D2}$)—C($R^{D3}R^{D4}$)—CO$_2$H, and $R^4$ is H, the carboxylic acid can be converted to an activated ester (for example by treatment with HATU and a base such as diisopropylethylamine or pyridine, or by treatment with TBTU in the presence of N-methylmorpholine) and the activated ester can be treated with further base to form to give a compound of structure 1C in which X' is —C($R^{D1}R^{D2}$)—C(O)— or —C($R^{D1}R^{D2}$)—C($R^{D3}R^{D4}$)—C(O)—.

Alternatively, if $R^2$ is an alkoxy group substituted by a carboxylic acid (—O—C($R^{D3}R^{D4}$)—CO$_2$H) or an aminoalkyl group substituted by a carboxylic acid (—N($R^{N1}$)—C($R^{D3}R^{D4}$)—CO$_2$H), and $R^4$ is H, 1B may be treated with a dehydrating agent (such as dicyclohexylcarbodiimide) in a solvent (such as DCM) to give a compound of structure 1C in which X' is —O—C($R^{D3}R^{D4}$)—C(O)— or —N($R^{N1}$)—C($R^{D3}R^{D4}$)—C(O)—.

Compounds of structure 1C (from Scheme 1) may alternatively be prepared as shown in Scheme 3. Compounds of structure 1A may be converted to intermediates of structure 3A by first forming the X' linker and then cyclisation to give the tricyclic core 1C.

SCHEME 3

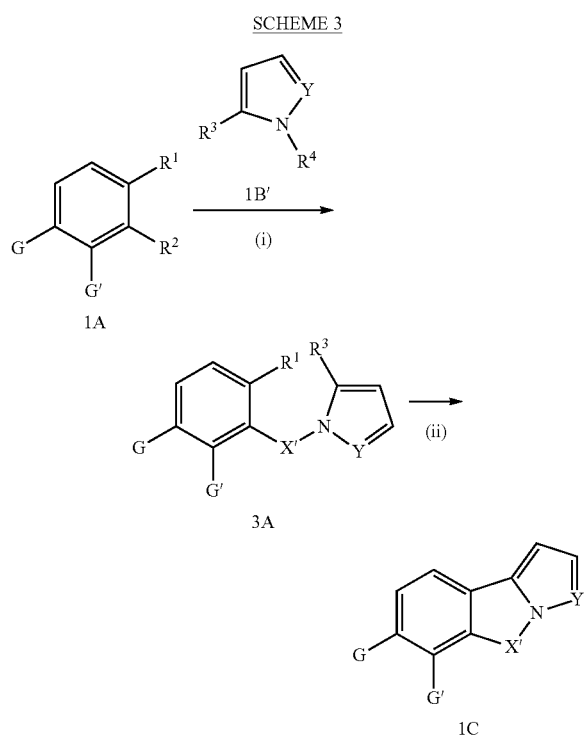

For example, in Scheme 3, Step (i), if $R^2$ is an alkyl group attached to a leaving group, for example —C($R^{D1}R^{D2}$)-L, —C($R^{D1}R^{D2}$)—C($R^{D3}R^{D4}$)-L or —C($R^{D1}R^{D2}$)—C($R^{D3}R^{D4}$)—C($R^{D5}R^{D6}$)-L, wherein L is a leaving group (such as a halogen, tosylate or mesylate) and $R^4$ is H, then 1A and 1B' may be combined and treated with a base (such as pyridine, potassium carbonate or sodium hydride) in a solvent (such as DCM, THF or toluene) at a temperature between room temperature and the reflux temperature of the solvent, to give a compound of structure 3A wherein X' is —C($R^{D1}R^{D2}$)—, —C($R^{D1}R^{D2}$)—C($R^{D3}R^{D4}$)— or —C($R^{D1}R^{D2}$)—C($R^{D3}R^{D4}$)—C($R^{D5}R^{D6}$)—.

Alternatively, in Scheme 3, Step (i), if $R^2$ is a hydroxyalkyl group, for example —C($R^{D1}R^{D2}$)—OH, —C($R^{D1}R^{D2}$)—C($R^{D3}R^{D4}$)—OH or —C($R^{D1}R^{D2}$)—C($R^{D3}R^{D4}$)—C($R^{D5}R^{D6}$)—OH and $R^4$ is H, then 1A and 1B' may be combined in the presence of a dehydrating agent (such as diisopropyl azodicarboxylate) in the presence of a phosphine, (such as triphenylphosphine), to give a compound of structure 3A wherein X' is —C($R^{D1}R^{D2}$)—, —C($R^{D1}R^{D2}$)—C($R^{D3}R^{D4}$)— or —C($R^{D1}R^{D2}$)—C($R^{D3}R^{D4}$)—C($R^{D5}R^{D6}$)—.

Alternatively, in Scheme 3, Step (i), compounds of structure 1A in which $R^2$ is an amino group (—NH($R^{N1}$)) may be combined with compounds of structure 1B' in which $R^4$ is an alkyl group substituted by a leaving group, such as —C($R^{D5}R^{D6}$)-L or —C($R^{D5}R^{D6}$)—C($R^{D3}R^{D4}$)-L, wherein L is a leaving group (such as a chloride or mesylate), and treated with a base (such as pyridine or triethylamine) in a solvent (such as DCM or toluene) at a temperature between room temperature and the reflux temperature of the solvent, to give compounds of structure 3A in which X' is —N($R^{N1}$)—C($R^{D5}R^{D6}$)— or —N($R^{N1}$)—C($R^{D3}R^{D4}$)—C($R^{D5}R^{D6}$)—.

Alternatively, in Scheme 3 Step (i), compounds of structure 1A, in which $R^2$ is an amino group (—NH($R^{N1}$)), may be combined with compounds of structure 1B', in which $R^4$ is H, and treated with an appropriate reagent (such as phosgene, triphosgene or carbonyl-diimidazole) in a solvent (such as DCM or toluene) and in the presence of a base (such as pyridine or triethylamine), optionally in the presence of a catalyst (such as 4-dimethylaminopyridine) at a temperature between room temperature and the reflux temperature of the solvent to give compounds of structure 3A in which X' is —N($R^{N1}$)—C(O)—.

Alternatively, in Scheme 3, Step (i), compounds of structure 1A, in which $R^2$ is an amino group (—NH($R^{N1}$)), may be treated with compounds of structure 1B' in which $R^4$ is an alkyl group substituted by a carboxylic acid (—C($R^{D5}R^{D6}$)CO₂H), in the presence of a dehydrating agent (such as dicyclohexylcarbodiimide) to give compounds of structure 3A, in which X' is —N($R^{N1}$)—C(O)—C($R^{D5}R^{D6}$)—.

Alternatively, in Scheme 3, Step (i), compounds of structure 1B', in which $R^4$ is an alkyl group substituted by a carboxylic acid, for example —C($R^{D5}R^{D6}$)—CO₂H, may be converted to an activated ester (for example by treatment with HATU and a base such as diisopropylethylamine or pyridine, or by treatment with TBTU in the presence of N-methylmorpholine). This activated ester may then be combined with compounds of structure 1A, in which $R^2$ is an amino group (—NH($R^{N1}$)), in the presence of a base (such as diisopropylethylamine or pyridine), to give a compound of structure 3A in which X' is —N($R^{N1}$)—C(O)—C($R^{D5}R^{D6}$)—.

Alternatively, in Scheme 3, Step (i), a compound of structure 1A, in which $R^2$ is an amino group (—NH($R^{N1}$)), may be converted to other compounds of structure 1A, in which $R^2$ is —N($R^{N1}$)—C(O)—CH₂-L, wherein L is a leaving group (such as a halide, for example a chloride or bromide), by treatment with a haloacetyl halide (such as chloroacetyl chloride or bromoacetyl bromide), in a solvent (such as THF or DCM) in the presence of a base (such as triethylamine or pyridine). This intermediate may be treated with a compound of structure 1B', in which $R^4$ is H, in the presence of a base (such as pyridine, potassium carbonate or sodium hydride) in a solvent (such as DCM, THF or toluene), at a temperature between room temperature and the reflux temperature of the solvent, to give a compound of structure 3A wherein X' is —N($R^{N1}$)—C(O)—CH₂—.

Alternatively, in Scheme 3, Step (i), compounds of structure 1A, in which $R^2$ is OH, may be combined with compounds of structure 1B', in which $R^4$ is a hydroxyalkyl group, for example —C($R^{D5}R^{D6}$)—OH or —C($R^{D5}R^{D6}$)—C($R^{D3}R^{D4}$)—OH, in the presence of a dehydrating agent (such as diisopropyl azodicarboxylate) and a phosphine, (such as triphenylphosphine) to give a compound of structure 3A in which X' is —O—C($R^{D5}R^{D6}$)— or —O—C($R^{D3}R^{D4}$)—C($R^{D5}R^{D6}$)—.

Alternatively, in Scheme 3, Step (i), compounds of structure 1A, in which $R^2$ is OH, may be combined with compounds of structure 1B', in which $R^4$ is an alkyl group substituted by a leaving group, for example —C($R^{D5}R^{D6}$)-L or —C($R^{D5}R^{D6}$)—C($R^{D3}R^{D4}$)-L, wherein L is a leaving group (such as a halide or sulfonate, for example a mesylate), in the presence of a base (such as potassium carbonate or sodium hydride) in a solvent (such as THF or DMF), at a temperature between room temperature and the reflux temperature of the solvent, to give a compound of structure 3A in which X' is —O—C($R^{D5}R^{D6}$)— or —O—C($R^{D3}R^{D4}$)—C($R^{D5}R^{D6}$)—.

Alternatively, compounds of structure 1A, in which $R^2$ is OH, may be combined with compounds of structure 1B', in which $R^4$ is H, and treated with an appropriate reagent (such as phosgene, triphosgene or carbonyl-diimidazole) in a solvent (such as THF, DCM or toluene) and in the presence of a base (such as potassium carbonate or sodium hydride) at a temperature between room temperature and the reflux temperature of the solvent, to give a compound of structure 3A in which X' is —O—C(O)—.

Alternatively, in Scheme 3, Step (i), compounds of structure 1A, in which $R^2$ is OH, may be treated with compounds of structure 1B' in which $R^4$ is an alkyl group substituted by a carboxylic acid (—C($R^{D5}R^{D6}$)$CO_2$H), in the presence of a dehydrating agent (such as dicyclohexylcarbodiimide) to give compounds of structure 3A, where X' is —O—C(O)—C($R^{D5}R^{D6}$)—.

Alternatively, in Scheme 3, Step (i), compounds of structure 1B', in which $R^4$ is an alkyl group substituted by a carboxylic acid, for example —C($R^{D5}R^{D6}$)$CO_2$H, may be converted to the corresponding activated ester (for example by treatment with HATU and a base such as diisopropylethylamine or pyridine, or by treatment with TBTU in the presence of N-methylmorpholine). This activated ester may then be combined with compounds of structure 1A, in which $R^2$ is OH, in the presence of a base (such as diisopropylethylamine or pyridiine) to give a compound of structure 3A, in which X' is —O—C(O)—C($R^{D5}R^{D6}$)—.

Alternatively, compounds of structure 1A, in which $R^2$ is OH, may be converted to other compounds of structure 1A, in which $R^2$ is —O—C(O)—$CH_2$-L, wherein L is a leaving group (such as a halide, for example a chloride or bromide), by treatment with a haloacetyl halide (such as chloroacetyl chloride or bromoacetyl bromide) in a solvent (such as THF or DCM), in the presence of a base (such as triethylamine or pyridine). Treatment of this intermediate with a compound of structure 1B', in which $R^4$ is H, in the presence of a base (such as pyridine, potassium carbonate or sodium hydride) in a solvent (such as DCM, THF or toluene) at a temperature between room temperature and the reflux temperature of the solvent, to give a compound of structure 3A, in which X' is —O—C(O)—$CH_2$—.

Alternatively, compounds of structure 1A, in which $R^2$ is an alkyl group attached to a carboxylic acid, for example —C($R^{D1}R^{D2}$)—$CO_2$H or —C($R^{D1}R^{D2}$)—C($R^{D3}R^{D4}$)—$CO_2$H, may be combined with compounds of structure 1B', in which $R^4$ is H, in the presence of a dehydrating agent (such as dicyclohexylcarbodiimide) in a solvent (such as DCM) to give a compound of structure 3A, in which X' is —C($R^{D1}R^{D2}$)—C(O)— or —C($R^{D1}R^{D2}$)—C($R^{D3}R^{D4}$)—C(O)—.

Alternatively, in Scheme 3, Step (i), if $R^2$ is an alkyl group substituted by a carboxylic acid, for example —C($R^{D1}R^{D2}$)$CO_2$H or —C($R^{D1}R^{D2}$)C($R^{D3}R^{D4}$)$CO_2$H, it may be converted to the corresponding activated ester (for example by treatment with HATU and a base such as diisopropylethylamine or pyridine, or by treatment with TBTU in the presence of N-methylmorpholine) and the activated ester can then be treated with a compound of structure 1B', in which $R^4$ is H in the presence of a further base (such as diisopropylethylamine or pyridine) to give a compound of structure 3A, in which X' is —C($R^{D1}R^{D2}$)—C(O)— or —C($R^{D1}R^{D2}$)—C($R^{D3}R^{D4}$)—C(O)—.

Alternatively, compounds of structure 1A, in which $R^2$ is an alkoxy group substituted by a carboxylic acid (—O—C($R^{D3}R^{D4}$)—$CO_2$H), or an aminoalkyl group substituted by a carboxylic acid (—N($R^{N1}$)—C($R^{D3}R^{D4}$)—$CO_2$H), may be combined with a compound of structure 1B', in which $R^4$ is H, in the presence of a dehydrating agent (such as dicyclohexylcarbodiimide) in a solvent (such as DCM) to give a compound of structure 3A, in which X' is —O—C($R^{D3}R^{D4}$)—C(O)— or —N($R^{N1}$)—C($R^{D3}R^{D4}$)—C(O)—.

In Scheme 3, Step (ii), compounds of structure 3A may be converted to compounds of structure 1C by formation of the carbon-carbon bond. One skilled in the art will recognize that it may be necessary to remove protecting groups and modify the groups $R^1$ and $R^3$ groups in order to carry out the reaction to form the carbon-carbon bond.

For example, compounds of structure 3A, in which either $R^1$ or $R^3$ is an appropriate group (such as a halide or a triflate) and the other group is a boronic acid or ester, may be treated with a palladium catalyst (such as palladium acetate, palladium chloride dppf or tris-(dibenzylideneacetone)dipalladium), optionally in the presence of a phosphine (such as triphenyl phosphine or tri-tert-butylphosphonium tetrafluoroborate) and a base (such as cesium carbonate) in a solvent (such as THF, dioxane or water or mixtures thereof) at a temperature between room temperature and the reflux temperature of the solvent, or by irradiation in the microwave at a temperature between 120 and 180° C., to give a compound of structure 1C.

Alternatively, compounds of structure 3A, in which either $R^1$ or $R^3$ is an appropriate group (such as a halide or a triflate) and the other group is a trialkyl stannane, may be treated with a palladium catalyst (such as palladium acetate, palladium chloride dppf or tris-(dibenzylideneacetone)dipalladium), optionally in the presence of a phosphine (such as triphenyl phosphine or tri-tert-butylphosphonium tetrafluoroborate) and a base (such as cesium carbonate) in a solvent (such as THF or dioxane) at a temperature between room temperature and the reflux temperature of the solvent, or by irradiation in the microwave at a temperature between 120 and 180° C., to give a compound of structure 1C.

Alternatively, in Scheme 3, Step (ii), a compound of structure 3A, in which $R^1$ is an appropriate group (such as a bromide or triflate), $R^3$ is H and Y is carbon, may be treated with a palladium catalyst (such as palladium acetate or bis-triphenylphosphine palladium chloride) in the presence of a base (such as cesium carbonate or potassium carbonate) optionally in the presence of a phosphine (such as triphenyl phosphine) in a solvent (such as DMF or dioxane), at a temperature between room temperature and the reflux temperature of the solvent, or alternatively by irradiation in the microwave at a temperature between 120 and 180° C., to give a compound of structure 1C, in which Y is carbon.

Alternatively, compounds of structure 3A, in which $R^1$ is a halide (such as a bromide or iodide), $R^3$ is H and Y is carbon, may be treated with an oxidising agent (such as oxygen or phenyl iodosoacetate) in the presence of a palladium catalyst (such as palladium acetate) in a solvent (such as acetic acid) at a temperature between room temperature and the reflux temperature of the solvent to give a compound of structure 1C in which Y is carbon.

In Scheme 1, Step (iii), compounds of structure 1C may be converted to compounds of General formula I by the conversion of the group G' to a carboxylic acid. If the group G' is a carboxylic ester (such as a methyl, tert-butyl or benzyl ester) then a variety of reagents and conditions known to those skilled in the art can be used to convert 1E into a compound of the General formula I. For example, if G' is a methyl, ethyl or benzyl ester, it may be converted to a carboxylic acid by treatment with an inorganic base (such as lithium hydroxide or sodium hydroxide) in a solvent (such as methanol, dioxane or water, or mixtures thereof) at a temperature between room temperature and the reflux temperature of the solvent, or alternatively by irradiation in the microwave at a temperature between 120 and 180° C. Alternatively, if G' is a benzyl ester it may be converted to a carboxylic acid by hydrogenation in the presence of a catalyst (for example, palladium on a solid support, such as carbon) in a solvent (such as dioxane or ethyl acetate). Alternatively, if G' is a tert-butyl ester, it may be converted to a carboxylic acid by treatment with an acid (such as trifluoromethanesulfonic acid or hydrogen chloride) in a solvent (such as dichloromethane or dioxane).

Alternatively, if the group G' is a nitrile, it may be converted into a carboxylic acid by treatment with aqueous acid (such as a mineral acid, for example hydrochloric acid) under appropriate conditions (such as heating, for example at reflux); or by treatment with aqueous base (such as an aqueous hydroxide, for example aqueous sodium hydroxide) under appropriate conditions (such as heating, for example at reflux).

Alternatively, if the group G' is an aldehyde or a hydroxymethyl moiety then it may be converted into a carboxylic acid by treatment with a suitable oxidising reagent (such as potassium permanganate or chromic acid).

A general strategy to prepare compounds of General formula 2 is shown in Scheme 4. The groups G and G' are as previously defined in Scheme 1.

butoxide or cesium carbonate) in a solvent (such as THF or toluene) at a temperature between room temperature and the reflux temperature of the solvent, or alternatively by irradiation in the microwave at a temperature between 120 and 180° C. to give compounds of structure 4B.

Alternatively, in Scheme 4, Step (i), the carbon-nitrogen bond may be formed by the reaction of a compound of structure 4A, in which $R^1$ is a suitable group (such as a halide or a triflate), with a compound of structure 4B', in the presence of a copper catalyst (such as copper or copper (I) iodide) in the presence of a base (such as potassium carbonate or potassium phosphate) optionally in the presence of an additive (such as a crown ether, for example 18-crown-6, or a ligand, for example 1,10-phenanthroline or 1,4-diaminocyclohexane) in a solvent (such as DMPU, DMF or toluene) at a temperature between room temperature and the reflux temperature of the

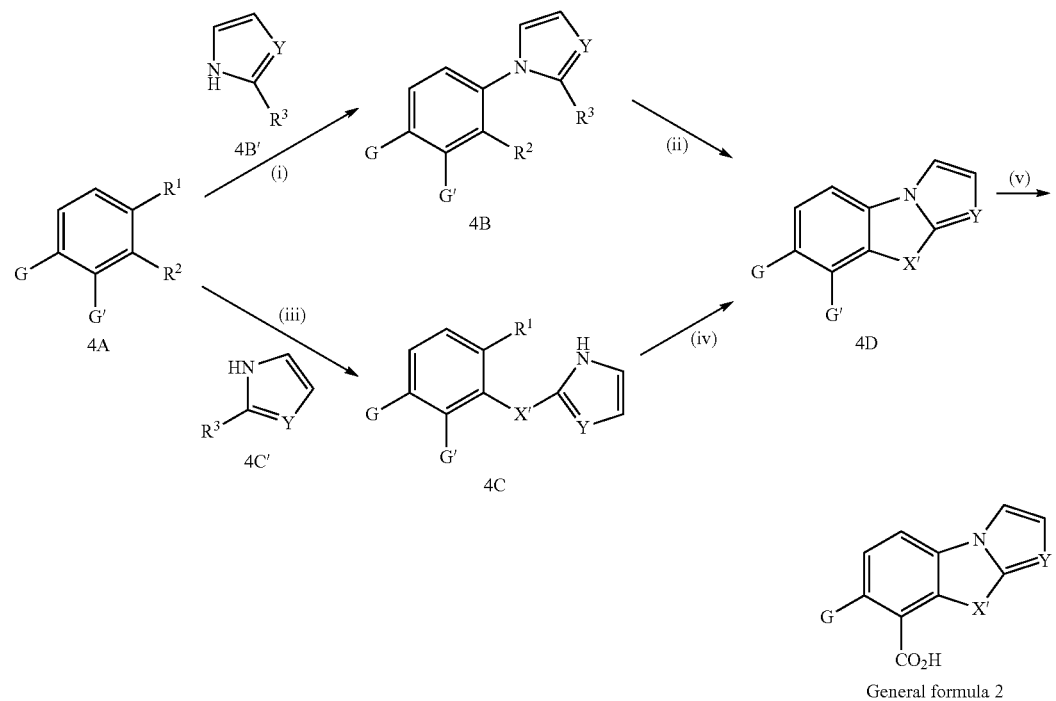

SCHEME 4

General formula 2

In Scheme 4, a compound of structure 4A, may be coupled with an appropriately substituted pyrrole or imidazole to form the carbon-nitrogen bond in 4B. Formation of the X' linker would generate the intermediate 4D. Alternatively, the X' linker may be formed first to give the intermediate 4C which may be cyclised to give 4D. It will be recognised by those skilled in the art that it may be necessary to modify the groups $R^1$, $R^2$ and $R^3$ in order to generate the required intermediates. In addition, protecting groups may be required during some of the steps.

In Scheme 4, Step (i), the carbon-nitrogen bond may be formed under a range of conditions known to those skilled in the art. For example, compounds of structure 4A may be reacted with compounds of structure 4B' in the presence of a palladium catalyst (such as palladium acetate or tris-(dibenzylideneacetone)-dipalladium) in the presence of a phosphine (such as BINAP or tri-tert-butylphosphonium tetrafluoroborate) and in the presence of a base (such as sodium tertsolvent, or alternatively by irradiation in the microwave at a temperature between 120 and 180° C.

In Scheme 4, Step (ii) the groups $R^2$ and $R^3$ of compound 4B can be coupled together to give the group X'. $R^2$ or $R^3$ may have been masked by protecting groups during Step (i), and may require deprotection before the group X' can be formed, or alternatively, $R^2$ and $R^3$ may require modification to other groups prior to the formation of the X' linker. For example, if $R^2$ is a nitro group, that group may be reduced, for example using hydrogen in the presence of a suitable catalyst (such as palladium on a solid support, such as carbon); or by treatment with an inorganic reducing agent (such as tin (II) chloride in DMF) to give an amino group. For example, if $R^2$ or $R^3$ is a hydroxyalkyl group, that group may be treated with an oxidising agent (such as Jones reagent or manganese dioxide) to give an aldehyde; or with a different oxidising agent (such as potassium permanganate) to give a carboxylic acid. For example, if $R^2$ or $R^3$ is an aldehyde, that group may be treated with an oxidising agent (such as potassium permanganate) to give a carboxylic acid, or with a reducing agent (such as sodium borohydride) to give an alcohol. For example, if $R^2$ or $R^3$ is a ketone, that group may be treated with a reducing agent (such as sodium borohydride) to give a secondary alcohol. For example, if $R^2$ or $R^3$ is a carboxylic acid or ester, that group may be treated with a reducing agent (such as lithium aluminium hydride) to give an alcohol. For example, if $R^2$ or $R^3$ is an alkene group, that group may be treated with a borane (such as 9-borobicyclononane) followed by oxidation with, for example, hydrogen peroxide to give a primary or secondary alcohol.

For example, compounds of structure 4B, in which $R^2$ is a vinyl group (—CH=CH$_2$) and $R^3$ is an alkenyl group, for example an allyl group (—CH$_2$—CH=CH$_2$), may undergo ring closing metathesis on treatment with a metal catalyst (such as Grubbs catalyst) in a solvent (such as DCM) at a temperature between room temperature and the reflux temperature of the solvent to give an intermediate in which X' is —CH=CH—CH$_2$—. Hydrogenation of this intermediate in the presence of a catalyst (such as palladium or palladium hydroxide on a solid support, such as carbon) in a solvent (such as ethanol or dioxane) optionally in the presence of an acid (such as acetic acid) to give a compound of structure 4D in which X' is —CH$_2$—CH$_2$—CH$_2$—.

Alternatively, compounds of structure 4B, in which $R^2$ is an amino group (—NH($R^{N1}$)) and $R^3$ is an alkyl group substituted by a leaving group, such as —C($R^{D5}R^{D6}$)-L or —C($R^{D5}R^{D6}$)—C($R^{D3}R^{D4}$)-L, wherein L is a leaving group (such as a chloride or a mesylate), may be treated with a base (such as pyridine or triethylamine) in a solvent (such as DCM or toluene) at a temperature between room temperature and the reflux temperature of the solvent, to give compounds of structure 4D in which X' is —N—($R^{N1}$)—C($R^{D5}R^{D6}$)— or —N($R^{N1}$)—C($R^{D3}R^{D4}$)—C($R^{D5}R^{D6}$)—.

Alternatively, compounds of structure 4B, in which $R^2$ is an alkylamino group (—C($R^{D1}R^{D2}$)NH($R^{N2}$)) and $R^3$ is an alkyl group substituted by a leaving group (—C($R^{D5}R^{D6}$)-L, wherein L is a leaving group, such as a chloride or a mesylate), may be treated with a base (such as pyridine or triethylamine) in a solvent (such as DCM or toluene) at a temperature between room temperature and the reflux temperature of the solvent, to give compounds of structure 4D in which X' is —C($R^{D1}R^{D2}$)—N($R^{N2}$)—C($R^{D5}R^{D6}$)—.

Alternatively, in Scheme 4, Step (ii), compounds of structure 4B, in which $R^2$ is an alkyl group substituted by a leaving group (—C($R^{D1}R^{D2}$)-L, wherein L is a leaving group, such as a chloride or mesylate) and $R^4$ is an alkylamino group (—C($R^{D5}R^{D6}$)—NH($R^{N2}$)), may be treated with a base (such as pyridine or triethylamine) in a solvent (such as DCM or toluene) at a temperature between room temperature and the reflux temperature of the solvent to give compounds of structure 4D in which X' is —C($R^{D1}R^{D2}$)—N($R^{N2}$)—C($R^{D5}R^{D6}$)—.

Alternatively, compounds of structure 4B, in which $R^2$ is an amino group (—NH($R^{N1}$)), and $R^4$ is an alkyl group substituted by a carboxylic acid, (—C($R^{D5}R^{D6}$)CO$_2$H), can be treated with a dehydrating agent (such as dicyclohexylcarbodiimide) to form 4D, where X' is —N($R^{N1}$)—C(O)—C($R^{D5}R^{D6}$)—.

Alternatively, in Scheme 4, Step (ii), if $R^2$ is an amino group (—NH($R^{N1}$)) and $R^4$ is an alkyl group substituted by a carboxylic acid (—C($R^{D5}R^{D6}$)—CO$_2$H), the carboxylic acid can be converted to an activated ester (for example, by treatment with HATU and a base such as diisopropylethylamine or pyridine, or by treatment with TBTU in the presence of N-methylmorpholine) and the activated ester can be treated with further base to form 4D in which X' is —N($R^{N1}$)—C(O)—C($R^{D5}R^{D6}$)—.

Alternatively, compounds of structure 4B, in which either $R^2$ or $R^3$ is NH$_2$ and the other group is an aldehyde group, may be heated in a solvent (such as ethanol or toluene) optionally in the presence of acid catalyst (for example 4-toluenesulfonic acid), to give compounds of structure 4D, in which X' is —CH=N—, or —N=CH—.

Alternatively, compounds of structure 4B, in which $R^2$ is OH and $R^3$ is a hydroxyalkyl group, for example —C($R^{D5}R^{D6}$)—OH or —C($R^{D5}R^{D6}$)—C($R^{D3}R^{D4}$)—OH, may be treated with a dehydrating agent (such as diisopropyl azodicarboxylate) in the presence of a phosphine, (such as triphenylphosphine), to give compounds of structure 4D, in which X' is —O—C($R^{D5}R^{D6}$)— or —O—C($R^{D3}R^{D4}$)—C($R^{D5}R^{D6}$)—.

Alternatively, compounds of structure 4B, in which $R^2$ is OH and $R^3$ is an alkyl group substituted by a leaving group, for example —C($R^{D5}R^{D6}$)-L or —C($R^{D5}R^{D6}$)—C($R^{D3}R^{D4}$)-L, wherein L is a leaving group (such as a chloride or a mesylate), may be treated with a base (such as potassium carbonate or sodium hydride) in a solvent (such as THF or DMF), at a temperature between room temperature and the reflux temperature of the solvent, to give a compound of structure 4D, in which X' is —O—C($R^{D5}R^{D6}$)— or —O—C($R^{D3}R^{D4}$)—C($R^{D5}R^{D6}$)—.

Alternatively, compounds of structure 4B, in which $R^2$ is OH and $R^3$ is an alkyl group substituted by a carboxylic acid (—C($R^{D5}R^{D6}$)—CO$_2$H) can be treated with a dehydrating agent (such as dicyclohexylcarbodiimide) to form 4D, in which X' is —O—C(O)—C($R^{D5}R^{D6}$)—.

Alternatively, if $R^2$ is OH and $R^3$ is an alkyl group substituted by a carboxylic acid (—C($R^{D5}R^{D6}$)—CO$_2$H), the carboxylic acid can be converted to an activated ester (for example by treatment with HATU and a base such as diisopropylethylamine or pyridine, or by treatment with TBTU in the presence of N-methylmorpholine), which can be further treated with base to form 4D, in which X' is —O—C(O)—C($R^{D5}R^{D6}$)—.

In Scheme 4, Step (iii), the linker X' may be formed by the reaction of an appropriately substituted intermediate 4A with an imidazole or pyrrole intermediate 4C'. It will be recognised by those skilled in the art that it may be necessary to have a protecting group present on the imidazole or pyrrole nitrogen prior to reaction and that the protecting group will need to be removed prior to Step (iv).

For example, in Scheme 4, Step (iii), compounds of structure 4A, in which $R^2$ is an amino group (—NH($R^{N1}$)), may be coupled with compounds of structure 4C', in which $R^3$ is an alkyl group substituted by a leaving group, such as —C($R^{D5}R^{D6}$)-L or —C($R^{D5}R^{D6}$)—C($R^{D3}R^{D4}$)-L, wherein L is a leaving group (such as a chloride or mesylate), in the presence of a base (such as pyridine or triethylamine) in a solvent (such as DCM or toluene) at a temperature between room temperature and the reflux temperature of the solvent to give compounds of structure 4C in which X' is —N($R^{N1}$)—C($R^{D5}R^{D6}$)— or —N($R^{N1}$)—C($R^{D3}R^{D4}$)—C($R^{D5}R^{D6}$)—.

Alternatively, compounds of structure 4A, in which $R^2$ is an amino group (—NH($R^{N1}$)), may be coupled with compounds of structure 4C', in which $R^3$ is an alkyl group substituted by a carboxylic acid (—C($R^{D5}R^{D6}$)—CO$_2$), in the presence of a dehydrating agent (such as dicyclohexylcarbodiimide) to form 4C, where X' is —N($R^{N1}$)—C(O)—C($R^{D5}R^{D6}$)—.

Alternatively, compounds of structure 4C', in which $R^3$ is an alkyl group substituted by a carboxylic acid (—C ($R^{D5}R^{D6}$)—CO$_2$H), may be converted to the corresponding activated ester (for example by treatment with HATU and a base such as diisopropylethylamine or pyridine, or by treatment with TBTU in the presence of N-methylmorpholine) and the activated ester may then be reacted with a compound of structure 4A, in which $R^2$ is an amino group (—NH($R^{N1}$)) in the presence of a base (such as diisopropylethylamine or pyridine) to give compounds of structure 4C, in which X' is —N($R^{N1}$)—C(O)—C($R^{D5}R^{D6}$)—.

Alternatively, compounds of structure 4A, in which $R^2$ is OH, may be reacted with compounds of structure 4C', in which $R^3$ is a hydroxyalkyl group, for example —C($R^{D5}R^{D6}$)—OH or —C($R^{D5}R^{D6}$)—C($R^{D3}R^{D4}$)—OH, in the presence of a dehydrating agent (such as diisopropyl azodicarboxylate) and a phosphine, (such as triphenylphosphine) to give a compound of structure 4C, in which X' is —O—C($R^{D5}R^{D6}$)— or —O—C($R^{D3}R^{D4}$)—C($R^{D5}R^{D6}$)—.

Alternatively, in Scheme 4, Step (iii), compounds of structure 4A, in which $R^2$ is OH may be reacted with compounds of structure 4C', in which $R^3$ is an alkyl group substituted by a leaving group, for example —C($R^{D5}R^{D6}$)-L or C($R^{D5}R^{D6}$)—C($R^{D3}R^{D4}$)-L, wherein L is a leaving group (such as a chloride or mesylate), in the presence of a base (such as potassium carbonate or sodium hydride) in a solvent (such as THF or DMF) at a temperature between room temperature and the reflux temperature of the solvent to give a compound of structure 4C, in which X' is —O—C($R^{D5}R^{D6}$)— or —O—C($R^{D3}R^{D4}$)—C($R^{D5}R^{D6}$)—.

Alternatively, compounds of structure 4A, in which $R^2$ is OH, may be reacted with a compound of structure 4C', in which $R^3$ is an alkyl group substituted by a carboxylic acid (—C($R^{D5}R^{D6}$)—CO$_2$H), in the presence of a dehydrating agent (such as dicyclohexylcarbodiimide) to form 4C, in which X' is —O—C(O)—C($R^{D5}R^{D6}$)—.

Alternatively, a compound of structure 4C', in which $R^3$ is an alkyl group substituted by a carboxylic acid (—C($R^{D5}R^{D6}$)—CO$_2$H), may be converted to the corresponding activated ester (for example by treatment with HATU and a base such as diisopropylethylamine or pyridine, or by treatment with TBTU in the presence of N-methylmorpholine), and the activated ester may then be reacted with a compound of structure 4A, in which $R^2$ is OH, in the presence of a base (such as diisopropylethylamine or pyridine) to give a compound of structure 4C, in which X' is —N($R^{N1}$)—C(O)—C($R^{D5}R^{D6}$)—.

In Scheme 4, Step (iv), a compound of structure 4C may be converted to a compound of structure 4D by formation of the carbon-nitrogen bond. It will be recognized by those skilled in the art that protecting groups may have been required during the earlier steps and that these will require removal prior to Step (iv).

In Scheme 4, Step (iv), the carbon nitrogen bond may be formed by the treatment of 4C, in which $R^1$ is a suitable leaving group (such as a halide or triflate), with a palladium catalyst (such as palladium acetate or tris-(dibenzylideneacetone)-dipalladium) in the presence of a phosphine (such as BINAP or tri-tert-butylphosphonium tetrafluoroborate) and in the presence of a base (such as sodium tert-butoxide or cesium carbonate) in a solvent (such as THF or toluene) at a temperature between room temperature and the reflux temperature of the solvent, or alternatively by irradiation in the microwave at a temperature between 120 and 180° C., to give 4D.

Alternatively, in Scheme 4, Step (iv), the carbon-nitrogen bond may be formed by the treatment of 4C, in which $R^1$ is a suitable group (such as a halide or a triflate), with a copper catalyst (such as copper or copper iodide) in the presence of a base (such as potassium carbonate or potassium phosphate) optionally in the presence of an additive (such as a crown ether, for example 18-crown-6, or a ligand, for example 1,10-phenanthroline or 1,4-diaminocyclohexane), in a solvent (such as DMPU, DMF or toluene) at a temperature between room temperature and the reflux temperature of the solvent, or alternatively by irradiation in the microwave at a temperature between 120 and 180° C., to give a compound of structure 4D.

Compounds of formula 4D, in which Y is nitrogen, may alternatively be prepared according to Scheme 5. The compounds of structure 4A may be converted to compounds of structure 5A or 5B, each of which may be cyclised to form compounds of structure 5C. Conversion of compounds of structure 5C to compounds of structure 4D is well known to those skilled in the art and will be described in detail below. It will be recognised that protecting groups may be required during some of the steps which will require removal prior to the additional steps.

SCHEME 5

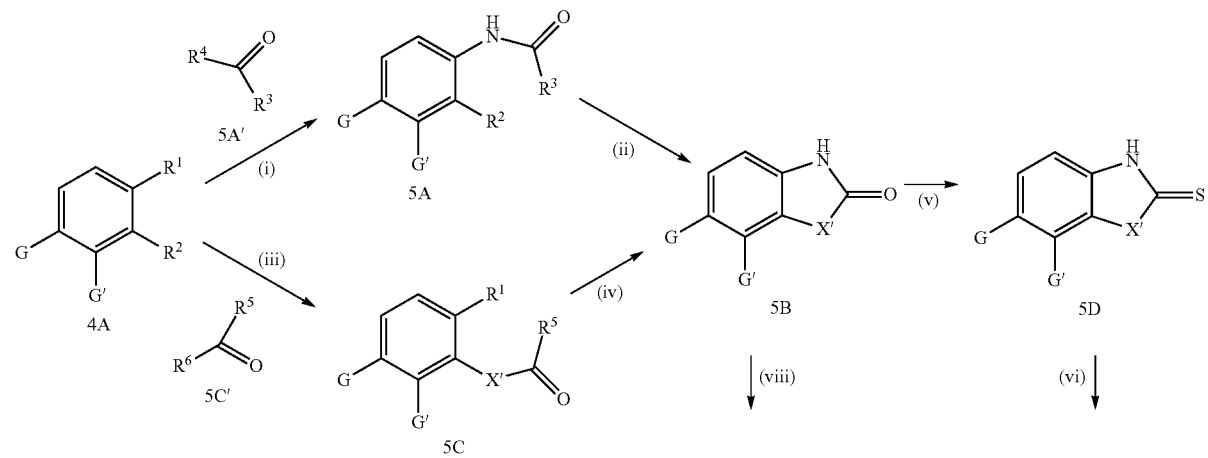

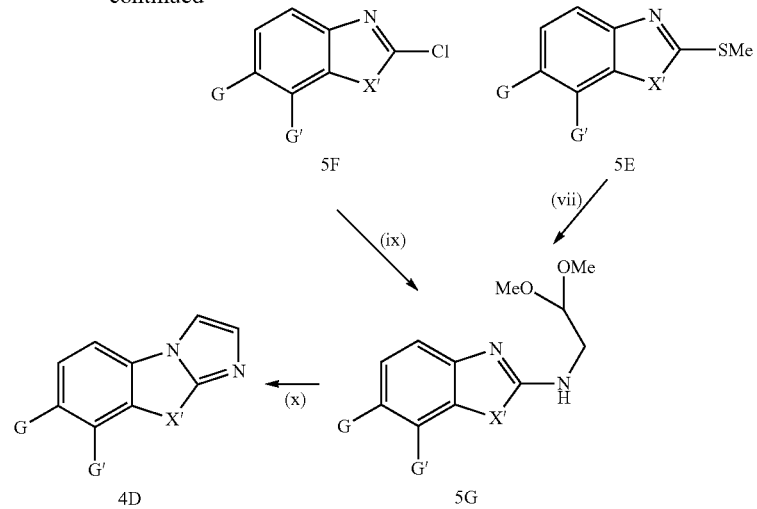

In Scheme 5, Step (i), compounds of structure 4A, in which $R^1$ is an amino group, may be reacted with compounds of structure 5A', in which $R^4$ is a leaving group (such as a chloride), in the presence of a base (such as triethylamine or pyridine) in a solvent (such as DCM or toluene) at a temperature between room temperature and the reflux temperature of the solvent.

Alternatively, in Scheme 5, Step (i), compounds of structure 5A', in which $R^4$ is OH, may be converted to the corresponding activated ester (for example by treatment with HATU and a base such as diisopropylethylamine or pyridine, or by treatment with TBTU in the presence of N-methylmorpholine) and the activated ester can then be reacted with a compound of structure 4A, in which $R^1$ is $NH_2$, in the presence of a base (such as diisopropylethylamine or pyridine) to give a compound of structure 5A.

In Scheme 5, Step (ii), compounds of structure 5A may be converted to compounds of structure 5B by formation of the X' linker. It will be recognised by those skilled in the art that it may be necessary to modify the groups $R^2$ and $R^3$ prior to the formation of the linker and that protecting groups present in Step (i) may need to be removed.

For example, in Scheme 5, Step (ii), compounds of structure 5A, in which either R2 or R3 is a vinyl group ($—CH=CH_2$) and the other group is an alkenyl group, for example an allyl group ($—CH_2—CH=CH_2$), may undergo ring closing metathesis on treatment with a metal catalyst (such as Grubbs catalyst) in a solvent (such as DCM) at a temperature between room temperature and the reflux temperature of the solvent to give an intermediate in which X' is $—CH=CH—CH_2—$ or $—CH_2—CH=CH—$. Hydrogenation of this intermediate in the presence of a catalyst (such as palladium or palladium hydroxide on a solid support, such as carbon) in a solvent (such as ethanol or dioxane) optionally in the presence of an acid (such as acetic acid) may give a compound of structure 5B, in which X' is $—CH_2—CH_2—CH_2—$.

Alternatively, compounds of structure 5A, in which $R^2$ is an amino group ($—NH(R^{N1})$) and $R^3$ is an alkyl group substituted by a leaving group, such as $—C(R^{D5}R^{D6})$-L or $—C(R^{D5}R^{D6})—C(R^{D3}R^{D4})$-L, wherein L is a leaving group (such as a chloride or mesylate), may be treated with a base (such as pyridine or triethylamine) in a solvent (such as DCM or toluene) at a temperature between room temperature and the reflux temperature of the solvent, to give compounds of structure 5B, in which X' is $—N(R^{N1})—C(R^{D5}R^{D6})—$ or $—N(R^{N1})—C(R^{D3}R^{D4})—C(R^{D5}R^{D6})—$.

Alternatively, compounds of structure 5A, in which $R^2$ is an amino group ($—NH(R^{N1})$) and $R^3$ is a carboxylic acid ($—CO_2H$) or an alkyl group substituted by a carboxylic acid ($—C(R^{D5}R^{D6})—CO_2H$), can be treated with a dehydrating agent (such as dicyclohexylcarbodiimide) to form 5B, in which X' is $—N(R^{N1})—C(O)—C(R^{D5}R^{D6})—$.

Alternatively, in compounds of structure 5A, in which $R^2$ is an amino group ($—NH(R^{N1})$) and $R^3$ is a carboxylic acid ($—CO_2H$) or an alkyl group substituted by a carboxylic acid ($—C(R^{D5}R^{D6})—CO_2H$), the carboxylic acid can be converted to an activated ester (for example by treatment with HATU and a base such as diisopropylethylamine or pyridine, or by treatment with TBTU in the presence of N-methylmorpholine) and the activated ester can be further treated with base to form 5B, in which X' is $—N(R^{N1})—C(O)—C(R^{D5}R^{D6})—$.

Alternatively, compounds of structure 5A, in which $R^2$ is OH and $R^3$ is a hydroxyalkyl group, for example $—C(R^{D5}R^{D6})—OH$ or $—C(R^{D5}R^{D6})—C(R^{D3}R^{D4})—OH$, may be treated with a dehydrating agent (such as diisopropyl azodicarboxylate) in the presence of a phosphine, (such as triphenylphosphine) to give a compound of structure 5B, in which X' is $—O—C(R^{D5}R^{D6})—$ or $—O—C(R^{D3}R^{D4})—C(R^{D5}R^{D6})—$.

Alternatively, compounds of structure 5A, in which $R^2$ is OH and $R^6$ is an alkyl group substituted by a leaving group, for example $—C(R^{D5}R^{D6})$-L or $C(R^{D5}R^{D6})—C(R^{D3}R^{D4})$-L, wherein L is a leaving group (such as a chloride or mesylate), may be treated with a base (such as potassium carbonate or sodium hydride) in a solvent (such as THF or DMF) at a temperature between room temperature and the reflux temperature of the solvent, to give a compound of structure 5B, in which X' is $—O—C(R^{D5}R^{D6})—$ or $—O—C(R^{D3}R^{D4})—C(R^{D5}R^{D6})—$.

Alternatively, compounds of structure 5A, in which $R^2$ is OH and $R^3$ is a carboxylic acid ($—CO_2H$) or an alkyl group substituted by a carboxylic acid ($—C(R^{D5}R^{D6})—CO_2H$), can be treated with a dehydrating agent (such as dicyclohexylcarbodiimide) to form 5B, in which X' is $—O—C(O)—C(R^{D5}R^{D6})—$.

Alternatively, if $R^2$ is OH and $R^3$ is a carboxylic acid ($—CO_2H$) or an alkyl group substituted by a carboxylic acid ($—C(R^{D5}R^{D6})—CO_2H$), the carboxylic acid can be converted to an activated ester (for example by treatment with HATU and a base such as diisopropylethylamine or pyridine, or by treatment with TBTU in the presence of N-methylmorpholine) which can then be treated with further base to form 5B, in which X' is $—O—C(O)—C(R^{D5}R^{D6})—$.

In Scheme 5, Step (iii), the X' linker may be formed by the reaction of an appropriately substituted intermediate 4A with an appropriately substituted and protected carboxylic acid derivative 5C', to give 5C. For example, compounds of structure 4A, in which $R^2$ is an aldehyde (—CHO), may be reacted with an appropriate compound 5C', in which $R^6$ is alkylidene phosphorane (for example ethoxymethylene triphenyl phosphorane), in a solvent (such as DCM, THF or toluene) at a temperature between room temperature and the reflux temperature of the solvent to give a compound of structure 5C, in which X' is —CH=CH—.

Alternatively, compounds of structure 4A, in which $R^2$ is an aldehyde (—CHO), may be reacted with an appropriate compound 5C', in which $R^6$ is a phosphonate (such as trimethyl phosphonoacetate) in the presence of a base (such as sodium hydride, potassium tert-butoxide or butyllithium) in a solvent (such as DMF or THF) at a temperature between −78° C. and room temperature to give a compound of structure 5C, in which X' is —CH=CH—.

A compound of structure 5C, in which X' is —CH=CH—, may be converted to other compounds of structure 5C, in which X' is —$CH_2$—$CH_2$—, by hydrogenation in the presence of a metal catalyst (for example palladium or palladium hydroxide on a solid support, such as carbon) in a solvent (such as methanol, ethanol or ethyl acetate).

Alternatively, compounds of structure 4A, in which $R^2$ is an amino group (—$NH(R^{N1})$), may be coupled with compounds of structure 5C', in which $R^6$ is an alkyl group substituted by a leaving group, such as —$C(R^{D5}R^{D6})$-L or —$C(R^{D5}R^{D6})$—$C(R^{D3}R^{D4})$-L, wherein L is a leaving group (such as a chloride or mesylate), in the presence of a base (such as pyridine or triethylamine) in a solvent (such as DCM or toluene) at a temperature between room temperature and the reflux temperature of the solvent to give compounds of structure 5C, in which X' is —$N(R^{N1})$—$C(R^{D5}R^{D6})$— or —$N(R^{N1})$—$C(R^{D3}R^{D4})$—$C(R^{D5}R^{D6})$—.

Alternatively, in Scheme 5, Step (iii), compounds of structure 4A, in which $R^2$ is an amino group (—$NH(R^{N1})$), may be coupled with compounds of structure 5C', in which $R^6$ is a carboxylic acid (—$CO_2H$) or an alkyl group substituted by a carboxylic acid (—$C(R^{D5}R^{D6})CO_2H$), in the presence of a dehydrating agent (such as dicyclohexylcarbodiimide) to form 5C, in which X' is —$N(R^{N1})$—C(O)— or —$N(R^{N1})$—C(O)—$C(R^{D5}R^{D6})$—.

Alternatively, a compound of structure 5C', in which $R^6$ is a carboxylic acid (—$CO_2H$) or an alkyl group substituted by a carboxylic acid (—$C(R^{D5}R^{D6})$—$CO_2H$), may be converted to the corresponding activated ester (for example by treatment with HATU and a base such as diisopropylethylamine or pyridine, or by treatment with TBTU in the presence of N-methylmorpholine), which can then be reacted with a compound of structure 4A in which $R^2$ is an amino group (—$NH(R^{N1})$), in the presence of a base (such as diisopropylethylamine or pyridine) to give a compound of structure 5C, in which X' is —$N(R^{N1})$—C(O)—$C(R^{D5}R^{D6})$—.

Alternatively, in Scheme 5, Step (iii), compounds of structure 4A, in which $R^2$ is $NH_2$, may be reacted with a compound of structure 5C', in which $R^6$ is an aldehyde group (such as a glyoxylic acid or ester), optionally in the presence of a drying agent (such as anhydrous sodium sulphate) in a solvent (such as DCM or toluene) at a temperature between room temperature and the reflux temperature of the solvent, to give compounds of structure 5C, in which X' is —N=CH—.

Alternatively, compounds of structure 4A, in which $R^2$ is an amino group, for example —$NH(R^{N1})$, may be reacted with a compound of structure 5C', in which $R^6$ is a vinyl group (such as an alkyl acrylate), in a solvent (such as acetic acid) at a temperature between room temperature and the reflux temperature of the solvent to give a compound of structure 5C, in which X' is —$N(R^{N1})$—$CH_2$—$CH_2$—.

Alternatively, compounds of structure 4A, in which $R^2$ is OH, may be reacted with compounds of structure 5C', in which $R^6$ is a hydroxyalkyl group, for example —$C(R^{D5}R^{D6})$—OH or —$C(R^{D5}R^{D6})$—$C(R^{D3}R^{D4})$—OH, in the presence of a dehydrating agent (such as diisopropyl azodicarboxylate) and a phosphine, (such as triphenylphosphine) to give a compound of structure 5C, in which X' is —O—$C(R^{D5}R^{D6})$— or —O—$C(R^{D3}R^{D4})$—$C(R^{D5}R^{D6})$—.

Alternatively, compounds of structure 4A, in which $R^2$ is OH, may be reacted with compounds of structure 5C', in which $R^6$ is an alkyl group substituted by a leaving group, for example —$C(R^{D5}R^{D6})$-L or —$C(R^{D5}R^{D6})$—$C(R^{D3}R^{D4})$-L, wherein L is a leaving group (such as a chloride or mesylate), in the presence of a base (such as potassium carbonate or sodium hydride) in a solvent (such as THF or DMF) at a temperature between room temperature and the reflux temperature of the solvent to give a compound of structure 5C, in which X' is —O—$C(R^{D5}R^{D6})$— or —O—$C(R^{D3}R^{D4})$—$C(R^{D5}R^{D6})$—.

Alternatively, compounds of structure 4A, in which $R^2$ is OH, may be reacted with a compound of structure 5C', in which $R^6$ is a carboxylic acid (—$CO_2H$) or an alkyl group substituted by a carboxylic acid (—$C(R^{D5}R^{D6})$—$CO_2H$), in the presence of a dehydrating agent (such as dicyclohexylcarbodiimide) to form 5C, in which X' is —O—C(O)— or —O—C(O)—$C(R^{D5}R^{D6})$—.

Alternatively, in Scheme 5, Step (iii), a compound of structure 5C', in which $R^6$ is a carboxylic acid (—$CO_2H$) or an alkyl group substituted by a carboxylic acid (—$C(R^{D5}R^{D6})$—$CO_2H$), may be converted to the corresponding activated ester (for example by treatment with HATU and a base such as diisopropylethylamine or pyridine, or by treatment with TBTU in the presence of N-methylmorpholine) and the activated ester can be reacted with a compound of structure 4A, in which $R^2$ is OH, in the presence of a base (such as diisopropylethylamine or pyridine) to give a compound of structure 5C, in which X' is —O—C(O)— or —O—C(O)—$C(R^{D5}R^{D6})$—.

In Scheme 5, Step (iv), compounds of structure 5C, may be converted to compounds of structure 5B by a variety of methods known to those skilled in the art. For example, if $R^1$ is $NH_2$ and $R^5$ is a leaving group (such as a chloride) then 5C may be treated with a base (such as triethylamine) in a solvent (such as DCM) at a temperature between room temperature and the reflux temperature of the solvent, to give compounds of structure 5B.

Alternatively, compounds of structure 5C, in which $R^1$ is $NH_2$ and $R^5$ is OH, may be treated with a dehydrating agent (such as dicyclohexylcarbodiimide) or an appropriate reagent (for example HATU and a base, such as diisopropylamine or pyridine, or TBTU in the presence of N-methylmorpholine) to give compounds of structure 5B.

Alternatively, compounds of structure 5C, in which $R^1$ is $NH_2$ and $R^5$ is an alkoxy group (such as methoxy or ethoxy), may be heated in a solvent (such as methanol or ethanol) to give compounds of structure 5B.

Alternatively, compounds of structure 5C, in which $R^1$ is an appropriate group (such as a bromide or triflate) and $R^5$ is $NH_2$, may be heated in a solvent (such as DMF or N-methylpyrrolidinone) in the presence of a base (such as potassium carbonate) optionally in the presence of a catalyst (for example a copper catalyst, such as copper (I) iodide) and an additive (such as N,N'-dimethylethylenediamine) at a temperature between 50° C. and the reflux temperature of the solvent, or alternatively by irradiating in the microwave at a temperature between 120 and 180° C., to give a compound of structure 5B.

In Scheme 5, Step (v), compounds of structure 5B may be converted to compounds of structure 5D by treatment with either Lawesson's reagent in a solvent (such as toluene, THF or DMF) at a temperature between room temperature and the reflux temperature of the solvent, or phosphorus pentasulfide, in a solvent (such as acetonitrile or toluene) optionally in the presence of a base (such as triethylamine) at a temperature between room temperature and the reflux temperature of the solvent.

In Scheme 5, Step (vi), compounds of structure 5D may be converted to compounds of structure 5E by treatment with methyl iodide in the presence of a base (such as potassium carbonate or cesium carbonate) in a solvent (such as acetone or DMF) at a temperature between room temperature and the reflux temperature of the solvent.

Alternatively, in Scheme 5, Step (viii), compounds of structure 5B may be converted to compounds of structure 5F by treatment with a chlorinating agent (such as phosphorus oxychloride) optionally in a solvent (such as toluene) at a temperature between room temperature and the reflux temperature of the mixture.

In Scheme 5, Step (vii) or Step (ix), compounds of structure 5E or 5F may be converted to compounds of structure 5G by reaction with aminoacetaldehyde dimethyl acetal, optionally in the presence of a base (such as triethylamine) in a solvent (such as ethanol or toluene) at a temperature between room temperature and the reflux temperature of the solvent.

In Scheme 5, Step (x), compounds of structure 5G may be treated with an acid (such as hydrochloric acid) in a solvent (such as methanol) at a temperature between room temperature and the reflux temperature of the solvent, to give compounds of structure 4D.

Compounds of structure 4D, in which Y is CH, may be alternatively prepared by aerial oxidation of the corresponding dihydropyrrole intermediates as shown in Scheme 6.

SCHEME 6

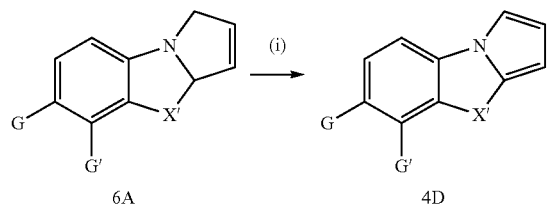

6A      4D

The dihydropyrrole intermediates 6A may be prepared in a similar manner to the corresponding pyrrole intermediates as described in Scheme 4. Oxidation by stirring in a solvent (such as DCM) in air will provide the compounds 4D.

In Scheme 4, Step (v), compounds of structure 4D may be converted to compounds of General formula 2 by conversion of the group G' to a carboxylic acid. This may be carried out as described earlier for compounds of General formula 1.

The general synthetic strategy to modify the group G is depicted in Scheme 7. The group G may be introduced and/or modified either before, during or after the assembly of the tricyclic ring system. Specific steps used to assemble the sulfonamide are described in more detail below.

SCHEME 7

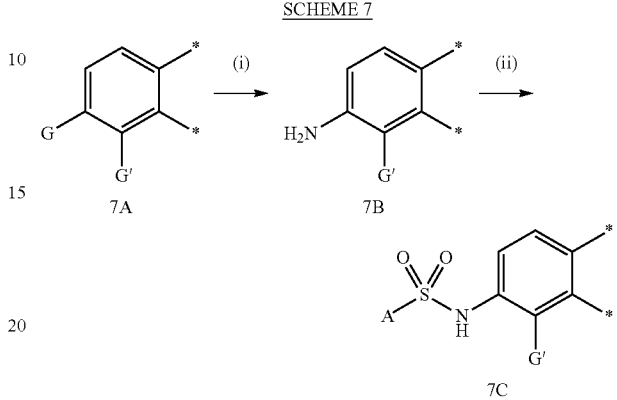

In Scheme 7, the asterisks denote either the presence of the groups $R^1$ and $R^2$ (as shown in Scheme 1 or Scheme 4), or the presence of the one or both of the rings of the tricyclic core, or intermediates towards the preparation of the core (as shown in Schemes 1-6).

In Scheme 7, Step (i), compounds of structure 7A, in which G is a nitro group, may be converted to compounds of structure 7B by reduction, for example by catalytic hydrogenation in the presence of a metal catalyst (for example palladium on a solid support such as carbon) in a solvent (such as tetrahydrofuran, methanol or ethanol). Alternatively, compounds of structure 7A, in which G is a nitro group, may be converted to compounds of structure 7B by chemical reduction. For example, the reduction may be achieved using a metal or metal salt (such as iron, zinc or tin (II) chloride) in the presence of an acid (such as hydrochloric acid or acetic acid).

In Scheme 7, Step (i), compounds of structure 7A, in which G is a protected amino group, may be converted to compounds of structure 7B by removal of the protecting groups. Protecting groups for amines are well known to those skilled in the art and methods for their removal are equally well known (for example, see Greene, Wuts, *Protective Groups in Organic Synthesis*. 2nd Ed. (1999)). For example, compounds of structure 7A, in which G is an amino group protected with one or two Boc groups, may be converted to compounds of structure 7B by treatment with an acid (such as trifluoroacetic acid, formic acid or hydrogen chloride) in a solvent (such as dichloromethane or dioxane).

Alternatively, in Scheme 7, Step (i), compounds of structure 7A, in which G is a pivaloyl protected amino group, may be converted to compounds of structure 7B by treatment with an acid (such as concentrated sulfuric acid) in a solvent (such as methanol or water) at a temperature between room temperature and the reflux temperature of the solvent.

In Scheme 7, Step (ii), compounds of structure 7B may be converted to compounds of structure 7C by treatment with an appropriate sulfonyl chloride (such as a substituted or unsubstituted benzenesulfonyl chloride) or an activated sulfonate ester (such as a pentafluorophenyl sulfonate ester) in the presence of a suitable base (such as pyridine, diisopropylethylamine or cesium carbonate) in a suitable solvent (such as dichloromethane or dimethylformamide) at a temperature between room temperature and the reflux temperature of the solvent.

Compounds of any of Formula I or II or, for example, General Formula I or II as depicted above, or any of the intermediates described in the schemes above, can be further derivatised by using one or more standard synthetic methods known to those skilled in the art. Such methods can involve substitution, oxidation or reduction reactions. These methods can also be used to obtain or modify compounds of General Formula I or any preceding intermediates by modifying, introducing or removing appropriate functional groups. Particular substitution approaches include alkylation, arylation, heteroarylation, acylation, thioacylation, halogenation, sulfonylation, nitration, formylation, hydrolysis and coupling procedures. These procedures can be used to introduce a functional group onto the parent molecule (such as the nitration or sulfonylation of aromatic rings) or to couple two molecules together (for example to couple an amine to a carboxylic acid to afford an amide; or to form a carbon-carbon bond between two heterocycles). For example, alcohol or phenol groups can be converted to ether groups by coupling a phenol with an alcohol in a solvent (such as tetrahydrofuran) in the presence of a phosphine (such as triphenylphosphine) and a dehydrating agent (such as diethyl, diisopropyl or dimethyl azodicarboxylate). Alternatively, ether groups can be prepared by deprotonation of an alcohol, using a suitable base (such as sodium hydride) followed by the addition of an alkylating agent (such as an alkyl halide or an alkyl sulfonate).

In another example, a primary or secondary amine can be alkylated using a reductive alkylation procedure. For example, the amine can be treated with an aldehyde and a borohydride (such as sodium triacetoxyborohydride, or sodium cyanoborohydride in a solvent (such as a halogenated hydrocarbon, for example dichloromethane, or an alcohol, for example ethanol) and, where necessary, in the presence of an acid (such as acetic acid).

In another example, hydroxy groups (including phenolic OH groups) can be converted into leaving groups, such as halogen atoms or sulfonyloxy groups (such as alkylsulfonyloxy, for example trifluoromethanesulfonyloxy, or aryl sufonyloxy, for example p-toluenesulfonyloxy) using conditions known to those skilled in the art. For example, an aliphatic alcohol can be reacted with thionyl chloride in a halogenated hydrocarbon (such as dichloromethane) to afford the corresponding alkyl chloride. A base (such as triethylamine) can also be used in the reaction.

In another example, ester groups can be converted to the corresponding carboxylic acid by acid- or base-catalysed hydrolysis depending on the nature of the ester group. Acid catalysed hydrolysis can be achieved by treatment with an organic or inorganic acid (such as trifluoroacetic acid in an aqueous solvent, or a mineral acid such as hydrochloric acid in a solvent such as dioxane). Base catalysed hydrolysis can be achieved by treatment with an alkali metal hydroxide (such as lithium hydroxide in an aqueous alcohol, for example methanol).

In another example, aromatic halogen substituents in the compounds may be subjected to halogen-metal exchange by treatment with a base (such as a lithium base, for example n-butyl or tert-butyl lithium) optionally at a low temperature (such as −78° C.) in a solvent (such as tetrahydrofuran) and the mixture may then be quenched with an electrophile to introduce a desired substituent. Thus, for example, a formyl group can be introduced by using dimethylformamide as the electrophile. Aromatic halogen substituents can also be subjected to palladium catalysed reactions to introduce groups such as carboxylic acids, esters, cyano or amino substituents.

In another example, an aryl, or heteroaryl ring substituted with an appropriate leaving group (such as a halogen or sulfonyl ester, for example a triflate) can undergo a palladium catalysed coupling reaction with a wide variety of substrates to form a carbon-carbon bond. For example, a Heck reaction can be used to couple such a ring system to an alkene (which may, or may not, be further substituted) by treatment with an organopalladium complex (such as tetrakis-(triphenylphosphine)palladium, palladium (II) acetate or palladium (II) chloride) in the presence of a ligand (such as a phosphine, for example triphenylphosphine) in the presence of a base (such as potassium carbonate or a tertiary amine, for example, triethylamine), in an appropriate solvent (such as THF or DMF), at a temperature between room temperature and the reflux temperature of the solvent. In another example, a Sonogashira reaction can be used to couple such a ring system to an alkyne (which may, or may not be further substituted) by treatment with a palladium complex (such as tetrakis-(triphenylphosphine)palladium) and a halide salt of copper (I) (such as copper (I) iodide), in the presence of a base (such as a potassium carbonate or a tertiary amine, for example, triethylamine), in an appropriate solvent (such as THF or DMF), at a temperature between room temperature and the reflux temperature of the solvent. In another example, a Stille reaction can be used to couple such a ring system to an alkene or alkyne, by treatment with an organotin compound (such as an alkenyltin or alkynyltin reagent, for example an alkenyltributylstannane) in the presence of a palladium complex (such as tetrakis-(triphenylphosphine)palladium(0)), optionally in the presence of a salt (such as a copper (I) halide), in an appropriate solvent (such as dioxane or DMF), at a temperature between room temperature and the reflux temperature of the solvent.

Particular oxidation approaches include dehydrogenations and aromatisation, decarboxylation and the addition of oxygen to certain functional groups. For example, aldehyde groups can be prepared by oxidation of the corresponding alcohol using conditions well known to those skilled in the art. For example, an alcohol can be treated with an oxidising agent (such as Dess-Martin periodinane) in a solvent (such as a halogenated hydrocarbon, for example dichloromethane). Alternative oxidising conditions can be used, such as treatment with oxalyl chloride and an activating amount of dimethylsulfoxide and subsequent quenching by the addition of an amine (such as triethylamine). Such a reaction can be carried out in an appropriate solvent (such as a halogenated hydrocarbon, for example dichloromethane) and under appropriate conditions (such as cooling below room temperature, for example to −78° C. followed by warming to room temperature). In another example, sulfur atoms can be oxidised to the corresponding sulfoxide or sulfone using an oxidising agent (such as a peroxy acid, for example 3-chloroperoxybenzoic acid) in an inert solvent (such as a halogenated hydrocarbon, for example dichloromethane) at around ambient temperature.

Particular reduction approaches include the removal of oxygen atoms from particular functional groups or saturation (or partial saturation) of unsaturated compounds including aromatic or heteroaromatic rings. For example, primary alcohols can be generated from the corresponding ester or aldehyde by reduction, using a metal hydride (such as lithium aluminium hydride or sodium borohydride in a solvent such as methanol). Alternatively, $CH_2OH$ groups can be generated from the corresponding carboxylic acid by reduction, using a metal hydride (such as lithium aluminium hydride in a solvent such as THF). In another example, a nitro group may be reduced to an amine by catalytic hydrogenation in the presence of a metal catalyst (such as palladium on a solid support such as carbon) in a solvent (such as an ether, for example THF, or an alcohol, such as methanol), or by chemical reduction using a metal (such as zinc, tin or iron) in the presence of an acid (such as acetic acid or hydrochloric acid). In a further example an amine can be obtained by reduction of a nitrile, for example by catalytic hydrogenation in the presence of a metal catalyst (for example palladium on a solid support such as carbon, or Raney nickel) in a solvent (such as THF) and under suitable conditions (such as cooling to below room temperature, for example to −78° C., or heating, for example to reflux).

Salts of compounds of General Formula I can be prepared by the reaction of a compound of General Formula I with an appropriate acid or base in a suitable solvent, or mixture of solvents (such as an ether, for example, diethyl ether, or an alcohol, for example ethanol, or an aqueous solvent) using conventional procedures. Salts of compound of General Formula I can be exchanged for other salts using methods known to those skilled in the art, for example by treatment using conventional ion-exchange chromatography procedures.

Where it is desired to obtain a particular enantiomer of a compound of General Formula I, this may be produced from a corresponding mixture of enantiomers by employing any suitable conventional procedure for resolving enantiomers known to those skilled in the art. For example, diastereomeric derivatives (such as salts) can be produced by reaction of a mixture of enantiomers of a compound of General Formula I (such a racemate) and an appropriate chiral compound (such as a chiral base). The diastereomers can then be separated by any conventional means such as crystallization or chromatography, and the desired enantiomer recovered (such as by treatment with an acid in the instance where the diastereomer is a salt). Alternatively, a racemic mixture of esters can be resolved by kinetic hydrolysis using a variety of biocatalysts (for example, see Patel *Steroselective Biocatalysts*, Marcel Decker; New York 2000).

In another resolution process a racemate of compounds of General Formula I can be separated using chiral High Performance Liquid Chromatography. Alternatively, a particular enantiomer can be obtained by using an appropriate chiral intermediate in one of the processes described above. Chromatography, recrystallisation and other conventional separation procedures may also be used with intermediates or final products where it is desired to obtain a particular geometric isomer of the invention.

II. Methods

Another aspect of the invention provides methods of modulating the activity of MetAP2. Such methods comprise exposing said receptor to a compound described herein. In some embodiments, the compound utilized by one or more of the foregoing methods is one of the generic, subgeneric, or specific compounds described herein, such as a compound of Formula I, Ia, Ib, Ic, II, IIa, IIb, IIc, IId, IIe, III, IV and V. The ability of compounds described herein to modulate or inhibit MetAP2 can be evaluated by procedures known in the art and/or described herein. Another aspect of the invention provides methods of treating a disease associated with expression or activity of MetAP2 in a patient. For example, a contemplated method includes administering a disclosed compound in an amount sufficient to establish inhibition of intracellular MetAP2 effective to increase thioredoxin production in the patient and to induce multi organ stimulation of anti-obesity processes in the subject, for example, by administering a disclosed compound in an amount insufficient to reduce angiogenesis in the patient.

In certain embodiments, the invention provides a method of treating and or ameliorating obesity in a patient by administering an effective amount of a disclosed compound. Also provided herein are methods for inducing weight loss in a patient in need thereof. Contemplated patients include not only humans, but other animals such as companion animals (e.g., dogs, cats).

Other contemplated methods of treatment include method of treating or ameliorating an obesity-related condition or co-morbidity, by administering a compound disclosed herein to a subject. For example, contemplated herein are methods for treating type 2 diabetes in a patient in need thereof.

Exemplary co-morbidities include cardiac disorders, endocrine disorders, respiratory disorders, hepatic disorders, skeletal disorders, psychiatric disorders, metabolic disorders, and reproductive disorders.

Exemplary cardiac disorders include hypertension, dyslipidemia, ischemic heart disease, cardiomyopathy, cardiac infarction, stroke, venous thromboembolic disease and pulmonary hypertension. Exemplary endocrine disorders include type 2 diabetes and latent autoimmune diabetes in adults. Exemplary respiratory disorders include obesity-hypoventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary reproductive disorders include sexual dysfunction, erectile dysfunction, infertility, obstetric complications, and fetal abnormalities. Exemplary psychiatric disorders include weight-associated depression and anxiety.

In particular, in certain embodiments, the invention provides a method of treating the above medical indications comprising administering to a subject in need thereof a therapeutically effective amount of a compound described herein, such as a compound of Formula I, Ia, Ib, Ic, II, IIa, IIb, IIc, IId, IIe, III, IV and V.

Obesity or reference to "overweight" refers to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using either of the formulas: weight(kg)/height$^2$(m$^2$) (SI) or 703× weight(lb)/height$^2$(in$^2$) (US).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. Obesity can also refer to patients with a waist circumference of about 102 cm for males and about 88 cm for females. For children, the definitions of overweight and obese take into account age and gender effects on body fat. Patients with differing genetic background may be considered "obese" at a level differing from the general guidelines, above.

The compounds of the present invention also are useful for reducing the risk of secondary outcomes of obesity, such as reducing the risk of left ventricular hypertrophy. Methods for treating patients at risk of obesity, such as those patients who are overweight, but not obese, e.g. with a BMI of between about 25 and 30 kg/m², are also contemplated. In certain embodiments, a patient is a human.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink.

In another aspect, the invention provides methods for treating an overweight or obese subject involving determining a level of at least one biomarker related to being overweight or obese in the subject, and administering an effective amount of a disclosed compound to achieve a target level in the subject. Exemplary biomarkers include body weight, Body Mass Index (BMI), Waist/Hip ratio WHR, plasma adipokines, and a combination of two or more thereof.

In certain embodiments, the compound utilized by one or more of the foregoing methods is one of the generic, subgeneric, or specific compounds described herein, such as a compound of Formula I, Ia, Ib, Ic, II, IIa, IIb, IIc, IId, IIe, III, IV and V.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound of this invention may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, is achieved. A treatment regimen can include a corrective phase, during which dose sufficient to provide reduction of weight is administered, and can be followed by a maintenance phase, during which a e.g. a lower dose sufficient to prevent weight gain is administered. A suitable maintenance dose is likely to be found in the lower parts of the dose ranges provided herein, but corrective and maintenance doses can readily be established for individual subjects by those of skill in the art without undue experimentation, based on the disclosure herein. Maintenance doses can be employed to maintain body weight in subjects whose body weight has been previously controlled by other means, including diet and exercise, bariatric procedures such as bypass or banding surgeries, or treatments employing other pharmacological agents.

III. Pharmaceutical Compositions and Kits

Another aspect of the invention provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the invention provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e. g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Advantageously, the invention also provides kits for use by a e.g. a consumer in need of weight loss. Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent, or administering a second active agent. For example, in addition to being overweight or obese, a subject or patient can further have overweight- or obesity-related co-morbidities, i.e., diseases and other adverse health conditions associated with, exacerbated by, or precipitated by being overweight or obese. Contemplated herein are disclosed compounds in combination with at least one other agent that has previously been shown to treat these overweight- or obesity-related conditions.

For example, Type II diabetes has been associated with obesity. Certain complications of Type II diabetes, e.g., disability and premature death, can be prevented, ameliorated, or eliminated by sustained weight loss (Astrup, A. Pub Health Nutr (2001) 4:499-5 15). Agents administered to treat Type II diabetes include sulfonylureas (e.g., Chlorpropamide, Glipizide, Glyburide, Glimepiride); meglitinides (e.g., Repaglinide and Nateglinide); biguanides (e.g., Metformin); thiazolidinediones (Rosiglitazone, Troglitazone, and Pioglitazone); dipeptidylpeptidase-4 inhibitors (e.g., Sitagliptin, Vildagliptin, and Saxagliptin); glucagon-like peptide-1 mimetics (e.g., Exenatide and Liraglutide); and alpha-glucosidase inhibitors (e.g., Acarbose and Miglitol.

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss. Agents administered to treat hypertension include Chlorthalidone; Hydrochlorothiazide; Indapamide, Metolazone; loop diuretics (e.g., Bumetanide, Ethacrynic acid, Furosemide, Lasix, Torsemide); potassium-sparing agents (e.g., Amiloride hydrochloride, benzamil, Spironolactone, and Triamterene); peripheral agents (e.g., Reserpine); central alpha-agonists (e.g., Clonidine hydrochloride, Guanabenz acetate, Guanfacine hydrochloride, and Methyldopa); alpha-blockers (e.g., Doxazosin mesylate, Prazosin hydrochloride, and Terazosin hydrochloride); beta-blockers (e.g., Acebutolol, Atenolol, Betaxolol, Bisoprolol fumarate, Carteolol hydrochloride, Metoprolol tartrate, Metoprolol succinate, Nadolol, Penbutolol sulfate, Pindolol, Propranolol hydrochloride, and Timolol maleate); combined alpha- and beta-blockers (e.g., Carvedilol and Labetalol hydrochloride); direct vasodilators (e.g., Hydralazine hydrochloride and Minoxidil); calcium antagonists (e.g., Diltiazem hydrochloride and Verapamil hydrochloride); dihydropyridines (e.g., Amlodipine besylate, Felodipine, Isradipine, Nicardipine, Nifedipine, and Nisoldipine); ACE inhibitors (benazepril hydrochloride, Captopril, Enalapril maleate, Fosinopril sodium, Lisinopril, Moexipril, Quinapril hydrochloride, Ramipril, Trandolapril); Angiotensin II receptor blockers (e.g., Losartan potassium, Valsartan, and Irbesartan); Renin inhibitors (e.g., Aliskiren); and combinations thereof. These compounds are administered in regimens and at dosages known in the art.

Carr et al. (The Journal of Clinical Endocrinology & Metabolism (2004) Vol. 89, No. 6 2601-2607) discusses a link between being overweight or obese and dyslipidemia. Dyslipidemia is typically treated with statins. Statins, HMG-CoA reductase inhibitors, slow down production of cholesterol in a subject and/or remove cholesterol buildup from arteries. Statins include mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin. These compounds are administered in regimens and at dosages known in the art. Eckel (Circulation (1997) 96:3248-3250) discusses a link between being overweight or obese and ischemic heart disease. Agents administered to treat ischemic heart disease include statins, nitrates (e.g., Isosorbide Dinitrate and Isosorbide Mononitrate), beta-blockers, and calcium channel antagonists. These compounds are administered in regimens and at dosages known in the art.

Wong et al. (Nature Clinical Practice Cardiovascular Medicine (2007) 4:436-443) discusses a link between being overweight or obese and cardiomyopathy. Agents administered to treat cardiomyopathy include inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers. These compounds are administered in regimens and at dosages known in the art. Yusef et al. (Lancet (2005) 366(9497):1640-1649) discusses a link between being overweight or obese and cardiac infarction. Agents administered to treat cardiac infarction include ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase). These compounds are administered in regimens and at dosages known in the art.

Suk et al. (Stroke (2003) 34:1586-1592) discusses a link between being overweight or obese and strokes. Agents administered to treat strokes include anti-platelet agents (e.g., Aspirin, Clopidogrel, Dipyridamole, and Ticlopidine), anti-coagulant agents (e.g., Heparin), and thrombolytic agents. Stein et al. (The American Journal of Medicine (2005) 18(9): 978-980) discusses a link between being overweight or obese and venous thromboembolic disease. Agents administered to treat venous thromboembolic disease include anti-platelet agents, anticoagulant agents, and thrombolytic agents. Sztrymf et al. (Rev Pneumol Clin (2002) 58(2):104-10) discusses a link between being overweight or obese and pulmonary hypertension. Agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil. Respiratory disorders and conditions such as obesity-hypoventilation syndrome, asthma, and obstructive sleep apnea, have been linked to being overweight or obese. Elamin (Chest (2004) 125:1972-1974) discusses a link between being overweight or obese and asthma. Agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex.

Kessler et al. (Eur Respir J (1996) 9:787-794) discusses a link between being overweight or obese and obstructive sleep apnea. Agents administered to treat sleep apnea include Modafinil and amphetamines.

Hepatic disorders and conditions, such as nonalcoholic fatty liver disease, have been linked to being overweight or obese. Tolman et al. (Ther Clin Risk Manag (2007) 6:1153-1163) discusses a link between being overweight or obese and nonalcoholic fatty liver disease. Agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents.

Skeletal disorders and conditions, such as, back pain and osteoarthritis of weight-bearing joints, have been linked to being overweight or obese. van Saase (J Rheumatol (1988) 15(7):1152-1158) discusses a link between being overweight or obese and osteoarthritis of weight-bearing joints. Agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid.

Metabolic disorders and conditions, for example, Prader-Willi Syndrome and polycystic ovary syndrome, have been linked to being overweight or obese. Cassidy (Journal of Medical Genetics (1997) 34:917-923) discusses a link between being overweight or obese and Prader-Willi Syndrome. Agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax).

Hoeger (Obstetrics and Gynecology Clinics of North America (2001) 28(1):85-97) discusses a link between being overweight or obese and polycystic ovary syndrome. Agents administered to treat polycystic ovary syndrome include insulin-sensitizers, combinations of synthetic estrogen and progesterone, Spironolactone, Eflornithine, and Clomiphene. Reproductive disorders and conditions such as sexual dysfunction, erectile dysfunction, infertility, obstetric complications, and fetal abnormalities, have been linked to being overweight or obese. Larsen et al. (Int J Obes (Lond) (2007) 8:1189-1198) discusses a link between being overweight or obese and sexual dysfunction. Chung et al. (Eur Urol (1999) 36(1):68-70) discusses a link between being overweight or obese and erectile dysfunction. Agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone. Pasquali et al. (Hum Reprod (1997) 1:82-87) discusses a link between being overweight or obese and infertility. Agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta.

Weiss et al. (American Journal of Obstetrics and Gynecology (2004) 190(4):1091-1097) discusses a link between being overweight or obese and obstetric complications. Agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic.

Psychiatric disorders and conditions, for example, weight-associated depression and anxiety, have been linked to being overweight or obese. Dixson et al. (Arch Intern Med (2003) 163:2058-2065) discusses a link between being overweight or obese and depression. Agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine);

monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate).

Simon et al. (Archives of General Psychiatry (2006) 63(7): 824-830) discusses a link between being overweight or obese and anxiety. Agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers.

Another aspect of the invention provides methods for facilitating and maintaining weight loss in a subject involving administering to the subject an amount of a disclosed compound effective to result in weight loss in the subject; and administering a therapeutically effective amount of a different weight loss agent to maintain a reduced weight in the subject. Weight loss agents include serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, bromocriptine, lorcaserin, topiramate, or agents acting to modulate food intake by blocking ghrelin action, inhibiting diacylglycerol acyltransferase 1 (DGAT1) activity, inhibiting stearoyl CoA desaturase 1 (SCD1) activity, inhibiting neuropeptide Y receptor 1 function, activating neuropeptide Y receptor 2 or 4 function, or inhibiting activity of sodium-glucose cotransporters 1 or 2. These compounds are administered in regimens and at dosages known in the art.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the invention.

$^1$H NMR spectra were recorded at ambient temperature using a Varian Unity Inova (400 MHz) spectrometer with a triple resonance 5 mm probe for Example compounds, and either a Bruker Avance DRX (400 MHz) spectrometer or a Bruker Avance DPX (300 MHz) spectrometer for Intermediate compounds. Chemical shifts are expressed in ppm relative to tetramethylsilane. The following abbreviations have been used: br=broad signal, s=singlet, d=doublet, dd=double doublet, dt=double triplet, ddd=double double doublet, t=triplet, td=triple doublet, tdd=triple double doublet, q=quartet, m=multiplet.

Mass Spectrometry (LCMS) experiments to determine retention times and associated mass ions were performed using the following methods:

Method A: Experiments were performed on a Waters ZMD single quadrapole mass spectrometer linked to a Hewlett Packard HP1100 LC system with a diode array detector. The spectrometer has an electrospray source operating in positive and negative ion mode. LC was carried out using a Luna 3 micron 30×4.6 mm C18 column and a 2 mL/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 minutes. The final solvent system was held constant for a further 1 minute.

Method B: Experiments were performed on a Waters platform LC quadrupole mass spectrometer linked to a Hewlett Packard HP1100 LC system with a diode array detector. The spectrometer has an electrospray source operating in positive and negative ion mode. Additional detection was achieved using a Sedex 85 evaporative light scattering device. LC was carried out using a Luna 3 micron 30×4.6 mm C18 column and a 2 mL/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 minutes. The final solvent system was held constant for a further 1 minute.

Method C: Experiments were performed on a Waters Micromass ZQ2000 quadrapole mass spectrometer linked to a Waters Acquity UPLC system with a PDA UV detector. The spectrometer has an electrospray source operating in positive and negative ion mode. LC was carried out using an Acquity BEH 1.7 micron C18 column, an Acquity BEH Shield 1.7 micron RP18 column or an Acquity HSST 1.8 micron column. Each column has dimensions of 100×2.1 mm and was maintained at 40° C. with a flow rate of 0.4 mL/minute. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 6 minutes. The final solvent system was held constant for a further 0.8 minutes.

Microwave experiments were carried out using a Biotage Initiator™, which uses a single-mode resonator and dynamic field tuning. Temperatures from 40-250° C. can be achieved, and pressures of up to 20 bars can be reached. A facility exists to apply air cooling during the irradiation.

H-Cube® is a continuous flow hydrogenation reactor from ThalesNano which allows temperatures up to 100° C. and pressures up to 100 bars. Various catalysts, housed in packed cartridges may be used and the product may be collected in fractions.

Preparative HPLC purification was carried out using either a C18-reverse-phase column from Genesis (C18) or a C6-phenyl column from Phenomenex (C6-phenyl) (100×22.5 mm i.d. with 7 micron particle size, UV detection at 230 or 254 nm, flow 5-15 mL/min), eluting with gradients from 100-0 to 0-100% water/acetonitrile or water/methanol containing 0.1% formic acid. Fractions containing the required product (identified by LCMS analysis) were pooled, the organic fraction was removed by evaporation, and the remaining aqueous fraction was lyophilised, to give the product.

Compounds which required column chromatography were purified manually or fully automatically using either a Biotage SP1™ Flash Purification system with Touch Logic Control™ or a Combiflash Companion® with pre-packed silica gel Isolute® SPE cartridge, Biotage SNAP cartridge or Redisep® Rf cartridge respectively.

Compounds have been named using Autonom2000 within ISISDraw.

ABBREVIATIONS

DCM Dichloromethane
DMF N,N-Dimethylformamide
DMAP 4-dimethylaminopyridine
THF Tetrahydrofuran
DMSO Dimethylsulfoxide
TFA Trifluoroacetic acid Example 1

8-[2-((Z)-3-Diethylaminoprop-1-enyl)-4-fluorobenzenesulfonylamino]-pyrazolo[5,1-a]isoquinoline-7-carboxylic acid

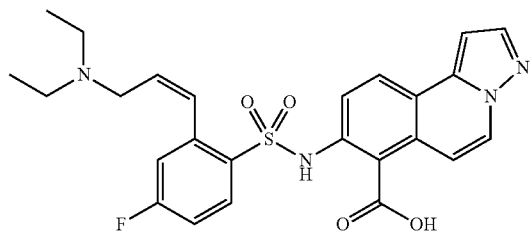 [SMILES: CCN(CC)C/C=C\c1cc(F)ccc1S(=O)(=O)Nc1ccc2c(ccn3nccc23)c1C(=O)O]

A mixture of methyl 8-[2-((Z)-3-diethylaminoprop-1-enyl)-4-fluorobenzenesulfonylamino]-pyrazolo[5,1-a]isoquinoline-7-carboxylate (Intermediate 1, 0.075 g) and lithium hydroxide (3M aqueous solution, 2 mL) in dioxane (6 mL) was heated to 80° C. for 6 hours. The resultant mixture was cooled and concentrated in vacuo. The residue was acidified using formic acid and then concentrated in vacuo. The residue was partitioned between ethyl acetate and water and the organic layer was dried (MgSO$_4$) and filtered. The filtrate was concentrated in vacuo and the residue was triturated with methanol. The mixture was centrifuged and the supernatant was decanted twice. The resultant solid was dried in vacuo overnight to give 8-[2-((Z)-3-diethylaminoprop-1-enyl)-4-fluorobenzenesulfonylamino]-pyrazolo[5,1-a]isoquinoline-7-carboxylic acid (0.044 g) as a solid.

$^1$H NMR (DMSO-d$_6$) δ: 8.38 (1H, d), 8.26 (1H, br, m), 8.17 (1H, d), 7.95 (1H, d), 7.83 (1H, br, m), 7.67 (1H, br, d), 7.43 (1H, br, d), 7.30-7.19 (2H, m), 7.10 (1H, br, s), 6.11 (1H, br, m), 3.84 (2H, br, m), 3.10 (4H, br, m), 1.07 (6H, br, t).

LCMS (Method C) r/t 3.48 (M+H) 497

Example 2

7-[2-((Z)-3-Diethylaminoprop-1-enyl)-4-fluorobenzenesulfonylamino]-4H-benzo[b]pyrrolo[1,2-d][1,4]oxazine-6-carboxylic acid

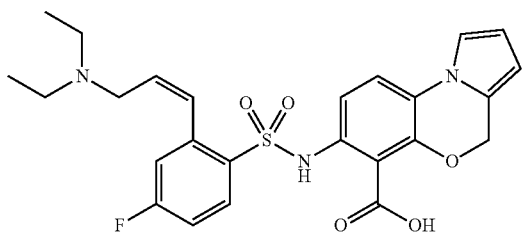 [SMILES: CCN(CC)C/C=C\c1cc(F)ccc1S(=O)(=O)Nc1ccc2c(c1C(=O)O)OCc1cccn1-2]

A suspension of methyl 7-[2-((Z)-3-diethylaminoprop-1-enyl)-4-fluorobenzenesulfonylamino]-4H-benzo[b]pyrrolo[1,2-d][1,4]oxazine-6-carboxylate (Intermediate 15, 0.074 g) and lithium hydroxide monohydrate (0.060 g) in dioxane (2 mL) and water (0.5 mL) was irradiated in the microwave at 130° C. for 45 minutes. After cooling, the mixture was acidified to pH3 with formic acid, diluted with ethanol and toluene and concentrated in vacuo. The residue was triturated with a solution of methanol in DCM (10%) and the solid was filtered off and washed with DCM. The filtrate was concentrated in vacuo and the residue was purified by chromatography on silica, eluting with a mixture of methanol and DCM with a gradient of 0-6%. The resultant solid was triturated with a mixture of ethyl acetate and ether and the solid obtained was dried in vacuo at 60° C. overnight to give 7-[2-((Z)-3-diethylaminoprop-1-enyl)-4-fluorobenzenesulfonylamino]-4H-benzo[b]pyrrolo[1,2-d][1,4]oxazine-6-carboxylic acid (0.012 g) as a white solid.

$^1$H NMR (DMSO-d$_6$) δ: 7.64 (1H, m), 7.53 (1H, d), 7.38 (2H, m), 7.24 (2H, m), 7.10 (1H, d), 6.24 (1H, t), 6.16 (1H, m), 6.00 (1H, d), 5.02 (2H, s), 3.80 (2H, br, d), 3.14 (4H, br, d), 1.14 (6H, t).

LCMS (Method C) r/t 3.54 (M+H) 500

Example 3

8-[2-((Z)-3-Diethylaminoprop-1-enyl)-4-fluorobenzenesulfonylamino]-5,6-dihydropyrazolo[5,1-a]isoquinoline-7-carboxylic acid

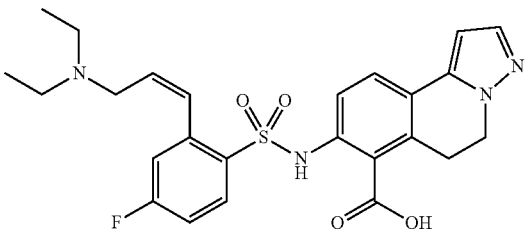 [SMILES: CCN(CC)C/C=C\c1cc(F)ccc1S(=O)(=O)Nc1ccc2c(c1C(=O)O)CCn1nccc1-2]

A mixture of methyl 8-[2-((Z)-3-diethylaminoprop-1-enyl)-4-fluorobenzenesulfonylamino]-5,6-dihydropyrazolo[5,1-a]isoquinoline-7-carboxylate (Intermediate 20, 0.057 g) and lithium hydroxide monohydrate (0.090 g) in dioxane (4 mL) and water (1 mL) was heated to 80° C. for 32 hours. The resultant mixture was concentrated in vacuo and the residue was acidified with aqueous citric acid solution (10%) and extracted into DCM, dried (MgSO$_4$) and filtered. The filtrate was concentrated in vacuo and the residue was purified by chromatography on silica, eluting with a mixture of methanol and DCM with a gradient of 0-15% to give 8-[2-((Z)-3-diethylaminoprop-1-enyl)-4-fluorobenzenesulfonylamino]-5,6-dihydropyrazolo[5,1-a]isoquinoline-7-carboxylic acid (0.020 g) as a white solid.

$^1$H NMR (DMSO-d$_6$) δ: 7.73 (1H, br, s), 7.53 (1H, br, d), 7.43-7.34 (3H, m), 7.29-7.19 (2H, m), 6.59 (1H, s), 6.14 (1H, br, s), 4.10 (2H, t), 3.82 (2H, br, s), 3.16 (2H, d), 3.13 (4H, br, s), 1.10 (6H, br, s).

LCMS (Method C) r/t 3.33 (M+H) 499

Example 4

7-[2-((Z)-3-Diethylaminoprop-1-enyl)-4-fluorobenzenesulfonylamino]-4H-5-oxa-3,9b-diazacyclopenta[a]naphthalene-6-carboxylic acid

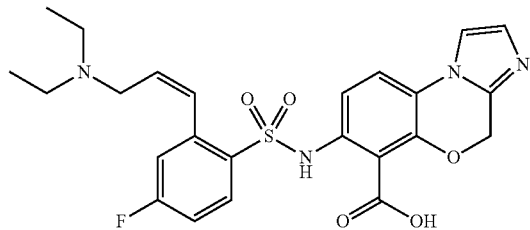 [SMILES: CCN(CC)C/C=C\c1cc(F)ccc1S(=O)(=O)Nc1ccc2c(c1C(=O)O)OCc1nccn1-2]

A mixture of methyl 7-[2-((Z)-3-diethylaminoprop-1-enyl)-4-fluorobenzenesulfonylamino]-4H-5-oxa-3,9b-diazacyclopenta[a]naphthalene-6-carboxylate (Intermediate 24, 0.138 g) and lithium hydroxide monohydrate (0.421 g) in dioxane (8 mL) and water (2 mL) was irradiated in the microwave at 135° C. for 45 minutes. After cooling, the mixture was diluted with methanol, acidified with formic acid and concentrated in vacuo. The residue was triturated with a solution of methanol in DCM (15%) and the solid was removed by filtration. The filtrate was concentrated in vacuo and the residue was purified by chromatography on silica, eluting with a mixture of methanol and DCM with a gradient of 0-30%. The resultant gum was triturated with ethyl acetate and the solid was collected by filtration to give 7-[2-((Z)-3-diethylaminoprop-1-enyl)-4-fluorobenzenesulfonylamino]-4H-5-oxa-3,9b-diazacyclopenta[a]naphthalene-6-carboxylic acid (0.091 g) as a white solid.

$^1$H NMR (DMSO-d$_6$) δ: 7.80 (1H, d), 7.70 (1H, m), 7.53 (1H, d), 7.37 (1H, d), 7.28-7.20 (2H, m), 7.12 (1H, d), 7.07 (1H, d), 6.13 (1H, m), 5.14 (2H, s), 3.78 (2H, br, s), 3.10 (4H, br, s), 1.11 (6H, t).

LCMS (Method C) r/t 2.52 (M+H) 501

Intermediate 1: Methyl 8-[2-((Z)-3-diethylaminoprop-1-enyl)-4-fluorobenzenesulfonylamino]-pyrazolo[5,1-a]isoquinoline-7-carboxylate

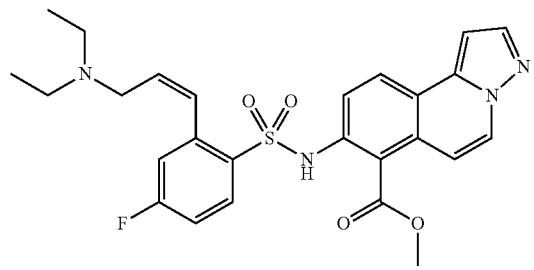 [SMILES: CCN(CC)C/C=C\c1cc(F)ccc1S(=O)(=O)Nc1ccc2c(ccn3nccc23)c1C(=O)OC]

A mixture of methyl 8-(2-bromo-4-fluorobenzenesulfonylamino]-pyrazolo[5,1-a]isoquinoline-7-carboxylate (Intermediate 2, 0.103 g), tris-(dibenzylideneacetone)-dipalladium (0) (0.025 g), tri-tert-butylphosphonium tetrafluoroborate (0.0127 g) and N,N-diethyl-N—((Z)-1-tributylstannanyl-prop-1-en-3-yl)-amine (Intermediate 3, 0.265 g) in dioxane (3 mL) was irradiated in the microwave at 80° C. for 2 hours. After cooling, the mixture was diluted with ethyl acetate and filtered through Celite. The filtrate was concentrated in vacuo and the residue was purified by chromatography on silica, eluting with a mixture of methanol and DCM with a gradient of 0-20% to give methyl 8-[2-((Z)-3-diethylaminoprop-1-enyl)-4-fluorobenzenesulfonylamino]-pyrazolo[5,1-a]isoquinoline-7-carboxylate (0.030 g).

$^1$H NMR (CDCl$_3$) δ: 8.26 (1H, d), 8.17 (1H, dd), 8.06 (1H, d), 7.96 (1H, s), 7.63 (1H, d), 7.40 (1H, d), 7.15-7.00 (3H, m), 6.89 (1H, s), 6.07 (1H, m), 4.05 (3H, s), 3.02 (2H, d), 2.44 (4H, q), 0.85 (6H, t).

Intermediate 2: Methyl 8-(2-bromo-4-fluorobenzenesulfonylamino]-pyrazolo[5,1-a]isoquinoline-7-carboxylate

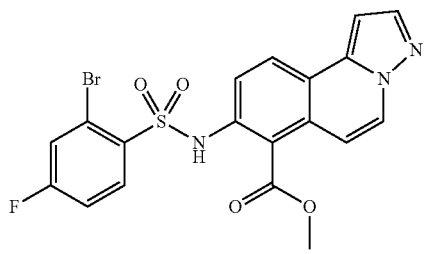

A mixture of methyl 8-aminopyrazolo[5,1-a]isoquinoline-7-carboxylate (Intermediate 6, 0.140 g) and 2-bromo-4-fluorobenzenesulfonyl chloride (0.190 g) in pyridine (4 mL) and DCM (3 mL) was stirred at room temperature overnight. The resultant mixture was concentrated in vacuo and the residue was purified by chromatography on silica, eluting with a mixture of ethyl acetate and cyclohexane with a gradient of 0-60%. The resultant glass was triturated with ether to give methyl 8-(2-bromo-4-fluorobenzenesulfonylamino]-pyrazolo[5,1-a]isoquinoline-7-carboxylate (0.103 g) as an off-white solid.

$^1$H NMR (CDCl$_3$) δ: 9.89 (1H, br, s), 8.30-8.20 (2H, m), 8.11 (1H, d), 7.97 (1H, s), 7.83 (1H, d), 7.43 (2H, m), 7.15 (1H, m), 6.93 (1H, s), 4.11 (3H, s).

Intermediate 3: N,N-Diethyl-N—((Z)-1-tributylstannanylprop-1-en-3-yl)-amine

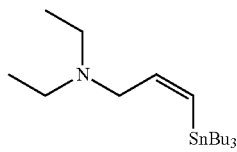

Diethylamine (19 mL) was added to a solution of ((Z)-3-bromoprop-1-enyl)-tributyl-stannane (Intermediate 4, 7.52 g) in THF (60 mL) and the mixture was stirred for 3 hours. The reaction mixture was evaporated to dryness and the residue was purified by chromatography on a silica column which had been pre-washed with 20% triethylamine in acetonitrile. The column was eluted with a mixture of ethyl acetate and pentane with a gradient of 0-10% to give N,N-diethyl-N—((Z)-1-tributylstannanylprop-1-en-3-yl)-amine (4.75 g) as an orange oil.

$^1$H NMR (CDCl$_3$) δ: 6.59 (1H, dt), 5.97 (1H, dt), 3.08 (2H, dd), 2.53 (4H, q), 1.49 (6H, m), 1.37-1.24 (6H, m), 1.04 (6H, t), 0.92-0.89 (15H, m).

Intermediate 4: ((Z)-3-Bromoprop-1-enyl)-tributylstannane

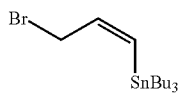

A solution of triphenylphosphine (5.32 g) in DCM (60 mL) was added to a solution of (Z)-3-tributylstannanylprop-2-en-1-ol (Intermediate 5, 6.4 g) and carbon tetrabromide (9.18 g) in DCM (60 mL) and the mixture was stirred for 2.5 hours. The mixture was evaporated to low volume and pentane was added. The solid was removed by filtration and the filtrate was evaporated to dryness. Pentane was added and the solid was again removed by filtration and the filtrate was evaporated to dryness to give ((Z)-3-bromoprop-1-enyl)-tributylstannane (12.14 g) as an oil.

$^1$H NMR (CDCl$_3$) δ: 6.71 (1H, dt), 6.11 (1H, d), 3.88 (2H, d), 1.52-1.50 (6H, m), 1.37-1.27 (6H, m), 0.99-0.97 (6H, m), 0.90 (9H, t).

Intermediate 5: (Z)-3-Tributylstannanylprop-2-en-1-ol

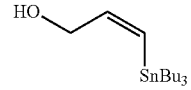

Propargyl alcohol (5 mL) was added to a solution of lithium aluminium hydride (1M in THF, 43 mL) in THF (70 mL) at −78° C. The resultant mixture was warmed to room temperature and stirred for 18 hours. It was re-cooled to −78° and a solution of tri-n-butyl tin chloride (8.3 mL) in ether (50 mL) was added and the mixture was stirred for 3 hours whilst gradually warming to room temperature. The reaction mixture was cooled to −5° C. and quenched by addition of water and 15% aqueous sodium hydroxide solution then it was allowed to warm to room temperature. Ethyl acetate was added and the mixture was stirred for 1 hour. The mixture was filtered through Celite and the filtrate was evaporated to dryness. The residue was purified by chromatography on a silica column which had been pre-washed with 20% triethylamine in acetonitrile. The column was eluted with a mixture of ethyl acetate and pentane with a gradient of 0-10% to give (Z)-3-tributylstannanylprop-2-en-1-ol (5.06 g) as a clear oil.

$^1$H NMR (CDCl$_3$) δ: 6.70 (1H, dt), 6.08 (1H, dt), 4.12 (2H, dd), 1.49 (6H, m), 1.31 (6H, m), 0.98-0.84 (15H, m).

Intermediate 6: Methyl 8-amino-pyrazolo[5,1-a]isoquinoline-7-carboxylate

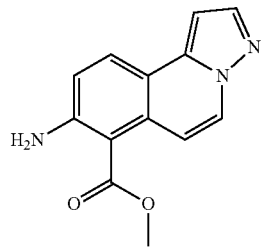 [SMILES: COC(=O)c1c(N)ccc2c1ccn1nccc21]

TFA (3 mL) was added to a solution of methyl 8-[bis-(tert-butoxycarbonyl)amino]-pyrazolo[5,1-a]isoquinoline-7-carboxylate (Intermediate 7, 0.280 g) in DCM (3 mL) and the reaction mixture was stirred at room temperature for 2 hours. The mixture was stirred with saturated aqueous sodium bicarbonate solution for 30 minutes and then the organic layer was separated, dried (MgSO$_4$) and filtered. The filtrate was concentrated in vacuo and the residue was purified by chromatography on silica, eluting with a mixture of ethyl acetate and cyclohexane with a gradient of 0-100% to give methyl 8-aminopyrazolo[5,1-a]isoquinoline-7-carboxylate (0.140 g) as a glass.

$^1$H NMR (CDCl$_3$) δ: 8.25 (1H, d), 7.96 (1H, d), 7.91 (1H, d), 7.72 (1H, d), 6.92 (1H, d), 6.78 (1H, d), 5.87-5.4 (2H, br), 4.03 (3H, s).

Intermediate 7: Methyl 8-[bis-(tert-butoxycarbonyl)amino]-pyrazolo[5,1-a]isoquinoline-7-carboxylate

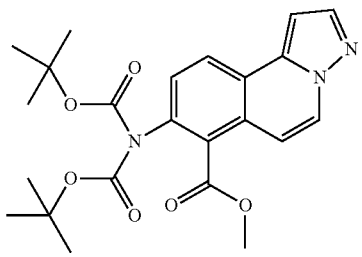 [SMILES: COC(=O)c1c(N(C(=O)OC(C)(C)C)C(=O)OC(C)(C)C)ccc2c1ccn1nccc21]

Methanesulfonyl chloride (0.5 mL) was added to a solution of methyl 8-[bis-(tert-butoxycarbonyl)amino]-6-hydroxy-5,6-dihydro-pyrazolo[5,1-a]isoquinoline-7-carboxylate (Intermediate 8, 0.290 g) in triethylamine (0.7 mL) and DCM (10 mL) and the reaction mixture was stirred at room temperature for 30 minutes. The resultant mixture was washed with 1M aqueous hydrochloric acid and the organic layer was separated, dried (MgSO$_4$) and filtered. The filtrate was concentrated in vacuo to give methyl 8-[bis-(tert-butoxycarbonyl)amino]-pyrazolo[5,1-a]isoquinoline-7-carboxylate (0.280 g) as a gum.

LCMS (Method B) r/t 3.83 (M+H) 442

Intermediate 8: Methyl 8-[bis-(tert-butoxycarbonyl)amino]-6-hydroxy-5,6-dihydro-pyrazolo[5,1-a]isoquinoline-7-carboxylate

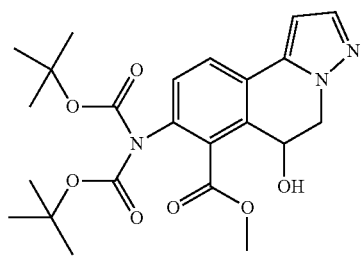 [SMILES: COC(=O)c1c(N(C(=O)OC(C)(C)C)C(=O)OC(C)(C)C)ccc2c1C(O)Cn1nccc1-2]

To a cooled solution of methyl 6-[bis-(tert-butoxycarbonyl)amino]-3-(2H-pyrazol-3-yl)-2-vinylbenzoate (Intermediate 9, 2.4 g) in anhydrous DCM (100 mL) at 0° C. was added (S,S)-(+)-N,N'-bis(3,5-di-tert-butylsalicylidene)-1,2-cyclohexanediamino manganese (III) chloride (0.280 g) and N-methylmorpholine N-oxide (3.2 g). m-Chloroperbenzoic acid (3.8 g) was then added portionwise and the reaction mixture was stirred at 0° C. for 20 minutes. The resultant mixture was quenched by the addition of 2M aqueous sodium carbonate solution and the organic layer was separated, dried (MgSO$_4$) and filtered. The filtrate was concentrated in vacuo and the residue was purified by chromatography on silica, eluting with a mixture of ethyl acetate and DCM with a gradient of 0-100%. The resultant material was repurified by chromatography on silica, eluting with a mixture of ethyl acetate and DCM with a gradient of 0-100% to give methyl 8-[bis-(tert-butoxycarbonyl)amino]-6-hydroxy-5,6-dihydro-pyrazolo[5,1-a]isoquinoline-7-carboxylate (0.290 g).

$^1$H NMR (CDCl$_3$) δ: 7.75 (1H, d), 7.59 (1H, s), 7.27 (1H, d), 6.64 (1H, s), 5.08 (1H, br, s), 4.79 (1H, d), 4.25 (1H, d), 3.96 (3H, s), 3.39 (1H, br, s), 1.39 (18H, s).

Intermediate 9: Methyl 6-[bis-(tert-butoxycarbonyl)amino]-3-(2H-pyrazol-3-yl)-2-vinylbenzoate

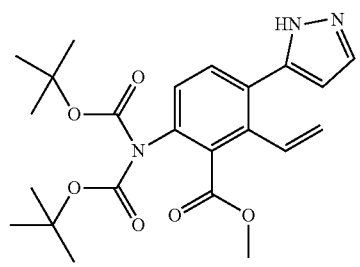 [SMILES: C=Cc1c(-c2ccn[nH]2)ccc(N(C(=O)OC(C)(C)C)C(=O)OC(C)(C)C)c1C(=O)OC]

A mixture of methyl 6-[bis-(tert-butoxycarbonyl)amino]-3-[2-(tetrahydropyran-2-yl)-2H-pyrazol-3-yl]-2-vinylbenzoate (Intermediate 10, 2.6 g) and concentrated hydrochloric acid (3 drops) in methanol (80 mL) was stirred at room temperature for 30 minutes. The solution was treated with saturated aqueous sodium bicarbonate solution and the mixture was concentrated in vacuo. The residue was partitioned between ethyl acetate and water and the organic layer was dried (MgSO$_4$) and filtered. The filtrate was concentrated in vacuo to give methyl 6-[bis-(tert-butoxycarbonyl)amino]-3-(2H-pyrazol-3-yl)-2-vinylbenzoate (2.38 g) as a white solid.

$^1$H NMR (CDCl$_3$) δ: 7.66 (2H, m), 7.19 (1H, d), 6.91 (1H, dd), 6.54 (1H, s), 5.43 (2H, m), 3.81 (3H, s), 1.42 (18H, s).

Intermediate 10: Methyl 6-[bis-(tert-butoxycarbonyl)amino]-3-[2-(tetrahydropyran-2-yl)-2H-pyrazol-3-yl]-2-vinylbenzoate

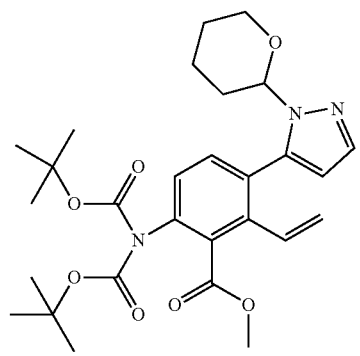 [SMILES: C=Cc1c(-c2ccnn2C2CCCCO2)ccc(N(C(=O)OC(C)(C)C)C(=O)OC(C)(C)C)c1C(=O)OC]

A mixture of methyl 6-[bis-(tert-butoxycarbonyl)amino]-3-[2-(tetrahydropyran-2-yl)-2H-pyrazol-3-yl]-2-trifluoromethanesulfonyloxybenzoate (Intermediate 11, 4.35 g), vinylboronic acid pinacol ester (1.9 mL), bis(triphenylphosphine)palladium (II) dichloride (0.255 g) and cesium carbonate (7.1 g) in dioxane (300 mL) and water (47 mL) was de-gassed and purged with nitrogen. The mixture was then heated to 80° C. for 4 hours. After cooling, the mixture was diluted with ether and the organic layer was separated, dried (MgSO$_4$) and filtered. The filtrate was concentrated in vacuo and the residue was purified by chromatography on silica, eluting with a mixture of ethyl acetate and cyclohexane with a gradient of 0-60% to give methyl 6-[bis-(tert-butoxycarbonyl)amino]-3-[2-(tetrahydropyran-2-yl)-2H-pyrazol-3-yl]-2-vinylbenzoate (2.84 g) as a gum.

$^1$H NMR (CDCl$_3$) δ: 7.62 (1H, s), 7.42 (1H, d), 7.19 (1H, d), 6.53 (1H, dd), 6.24 (1H, s), 5.25 (2H, m), 4.85 (1H, d), 3.98 (1H, d), 3.81 (3H, s), 3.29 (1H, t), 2.46 (1H, m), 2.00 (1H, d), 1.78 (1H, d), 1.73-1.57 (1H, m), 1.46 (2H, m), 1.43 (18H, m).

Intermediate 11: Methyl 6-[bis-(tert-butoxycarbonyl)amino]-3-[2-(tetrahydropyran-2-yl)-2H-pyrazol-3-yl]-2-trifluoromethanesulfonyloxybenzoate

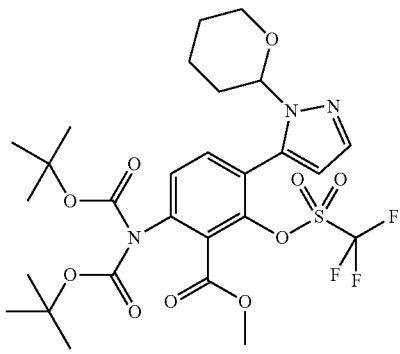 [SMILES: COC(=O)c1c(N(C(=O)OC(C)(C)C)C(=O)OC(C)(C)C)ccc(-c2ccnn2C2CCCCO2)c1OS(=O)(=O)C(F)(F)F]

A mixture of methyl 6-[bis-(tert-butoxycarbonyl)amino]-2-hydroxy-3-[2-(tetrahydropyran-2-yl)-2H-pyrazol-3-yl]-benzoate (Intermediate 12, 4.84 g), N,N-bis-(trifluoromethanesulfonyl)aniline (4.53 g), triethylamine (2.5 mL) and DMAP (0.1 g) in DCM (200 mL) was stirred at room temperature overnight. The resultant mixture was concentrated in vacuo and the residue was purified by chromatography on silica, eluting with a mixture of ethyl acetate and cyclohexane with a gradient of 0-70%. The resultant gum was dissolved in the minimum amount of ether and sonicated. It was then diluted with heptane and the resultant solid was collected by filtration to give methyl 6-[bis-(tert-butoxycarbonyl)amino]-3-[2-(tetrahydropyran-2-yl)-2H-pyrazol-3-yl]-2-trifluoromethanesulfonyloxybenzoate (4.35 g) as a white solid.

$^1$H NMR (CDCl$_3$) δ: 7.76 (1H, d), 7.68 (1H, s), 7.36 (1H, d), 6.50 (1H, d), 4.96 (1H, d), 4.09 (1H, d), 3.93 (3H, s), 3.45 (1H, t), 2.54 (1H, m), 2.08 (1H, d), 1.88 (1H, d), 1.74 (1H, m), 1.53 (2H, m), 1.43 (18H, s).

Intermediate 12: Methyl 6-[bis-(tert-butoxycarbonyl)amino]-2-hydroxy-3-[2-(tetrahydropyran-2-yl)-2H-pyrazol-3-yl]-benzoate

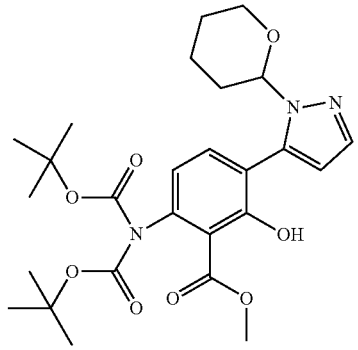 [SMILES: COC(=O)c1c(N(C(=O)OC(C)(C)C)C(=O)OC(C)(C)C)ccc(-c2ccnn2C2CCCCO2)c1O]

A mixture of methyl 3-bromo-6-[bis-(tert-butoxycarbonyl)amino]-2-hydroxy benzoate (Intermediate 13, 5.0 g), 1-(tetrahydropyran-2-yl)-5-(4,4,5,5-tetramethyl-[1,3,2]dioxaborolan-2-yl)-1H-pyrazole (3.9 g), tris-(dibenzylideneacetone)dipalladium (0) (0.51 g), tri-tert-butylphosphonium tetrafluoroborate (0.33 g) and cesium carbonate (11.0 g) in dioxane (150 mL) and water (20 mL) was degassed and purged with nitrogen. The resultant mixture was then heated to 65° C. for 1 hour. After cooling, the mixture was filtered through Celite and washed with ethyl acetate The filtrate was concentrated in vacuo and the residue was purified by chromatography on silica, eluting with a mixture of ethyl acetate and cyclohexane with a gradient of 0-70% to give methyl 6-[bis-(tert-butoxycarbonyl)amino]-2-hydroxy-3-[2-(tetrahydropyran-2-yl)-2H-pyrazol-3-yl]-benzoate (4.84 g) as a gum.

$^1$H NMR (CDCl$_3$) δ: 11.64 (1H, s), 7.66 (1H, s), 7.56 (1H, s), 6.81 (1H, d), 6.37 (1H, d), 5.07 (1H, d), 4.01 (1H, d), 3.96 (3H, s), 3.40 (1H, t), 2.50 (1H, m), 2.04 (1H, d), 1.97 (1H, d), 1.70 (2H, m), 1.51 (1H, m), 1.42 (18H, s).

Intermediate 13: Methyl 3-bromo-6-[bis-(tert-butoxycarbonyl)amino]-2-hydroxy benzoate

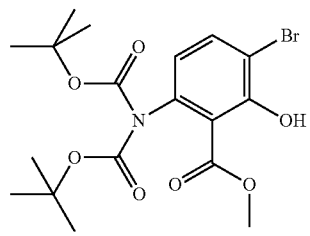 [SMILES: COC(=O)c1c(N(C(=O)OC(C)(C)C)C(=O)OC(C)(C)C)ccc(Br)c1O]

Methyl 3-bromo-6-bis-(tert-butoxycarbonyl)amino-2-(4-methylbenzenesulfonyl-oxy)benzoate (Intermediate 14, 6.2 g) was dissolved in methanol (200 mL) and 1M aqueous sodium hydroxide solution (50 mL) was added. The reaction mixture was stirred at room temperature for 30 minutes then the methanol was removed in vacuo and the residue was diluted with a mixture of ethyl acetate and water and then acidified with acetic acid. The layers were separated and the organic phase was dried (Na$_2$SO$_4$) and filtered. The filtrate was concentrated in vacuo to give methyl 3-bromo-6-bis- (tert-butoxycarbonyl)amino-2-hydroxybenzoate (4.51 g) as a sandy coloured solid.

¹H NMR (CDCl₃) δ: 11.88 (1H, s), 7.71 (1H, d), 6.64 (1H, d), 3.96 (3H, s), 1.39 (18H, s).

Intermediate 14: Methyl 3-bromo-6-bis-(tert-butoxycarbonyl)amino-2-(4-methylbenzenesulfonyloxy) benzoate

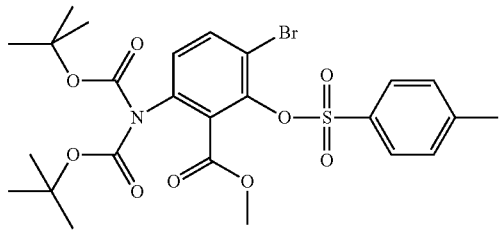 [SMILES: COC(=O)c1c(N(C(=O)OC(C)(C)C)C(=O)OC(C)(C)C)ccc(Br)c1OS(=O)(=O)c1ccc(C)cc1]

Methyl 6-amino-3-bromo-2-hydroxybenzoate (prepared according to Wang et al, *Bioorg Med Chem Lett,* 2007, 17, 2817; 19.88 g) was dissolved in DCM (390 mL) and triethylamine (17.96 g), DMAP (9.86 g) and 4-methylbenzenesulfonyl chloride (15.43 g) were added. The mixture was stirred at room temperature for 4 hours then washed with water, dried (MgSO₄) and filtered. The filtrate was concentrated in vacuo to give a yellow gum. This was dissolved in acetonitrile (390 mL) and DMAP (9.86 g) and di-tert-butyl dicarbonate (37.2 g) were added and the resultant mixture was stirred at room temperature overnight. Further di-tert-butyl dicarbonate (14.5 g) was added and the mixture was stirred at room temperature for an additional 1 hour. The mixture was concentrated in vacuo and the residue was dissolved in ethyl acetate and washed with aqueous citric acid (10%), aqueous sodium bicarbonate solution and brine, dried (MgSO₄) and filtered. The filtrate was concentrated in vacuo and the residue was triturated with a mixture of ether and cyclohexane (4:1, 100 mL) and the solid was removed by filtration. The filtrate was concentrated in vacuo and the residue was purified by chromatography on silica, eluting with a mixture of ethyl acetate and cyclohexane with a gradient of 0-60% to give methyl 3-bromo-6-bis-(tert-butoxycarbonyl)amino-2-(4-methylbenzenesulfonyloxy)benzoate (43.37 g) as a pale yellow powder.

¹H NMR (CDCl₃) δ: 7.78 (2H, d), 7.62 (1H, d), 7.33 (2H, d), 7.02 (1H, d), 3.81 (3H, s), 2.47 (3H, s), 1.39 (18H, s).

Intermediate 15: Methyl 7-[2-((Z)-3-diethylaminoprop-1-enyl)-4-fluorobenzenesulfonylamino]-4H-benzo[b]pyrrolo[1,2-d][1,4]oxazine-6-carboxylate

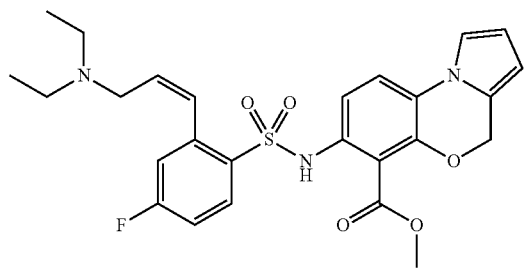 [SMILES: CCN(CC)C/C=C\c1cc(F)ccc1S(=O)(=O)Nc1ccc2c(c1C(=O)OC)OCc1cccn1-2]

A mixture of methyl 7-(2-bromo-4-fluorobenzenesulfonylamino]-4H-benzo[b]pyrrolo[1,2-d][1,4]oxazine-6-carboxylate (Intermediate 16, 0.107 g) and N,N-diethyl-N—((Z)-1-tributylstannanylprop-1-en-3-yl)-amine (Intermediate 3, 0.179 g) in dioxane (3 mL) and DMSO (0.3 mL) was degassed and purged with nitrogen. Tris-(dibenzylideneacetone)dipalladium (0) (0.01 g) and tri-tert-butylphosphonium tetrafluoroborate (0.006 g) were added and the mixture was degassed and purged with nitrogen again, then the mixture was heated to 95° C. for 1 hour. After cooling, the mixture was partitioned between ethyl acetate and water. The aqueous layer was extracted with more ethyl acetate and the combined organic layers were dried (MgSO₄) and filtered. The filtrate was concentrated in vacuo and the residue was purified by chromatography on silica, eluting with a mixture of methanol and DCM with a gradient of 0-5% to give methyl 7-[2-((Z)-3-diethylaminoprop-1-enyl)-4-fluorobenzenesulfonylamino]-4H-benzo[b]pyrrolo[1,2-d][1,4]oxazine-6-carboxylate (0.074 g) as a sticky yellow oil.

¹H NMR (CDCl₃) δ: 8.05 (1H, dd), 7.32 (1H, d), 7.12-7.02 (4H, m), 6.97 (1H, d), 6.32 (1H, t), 6.09-6.03 (2H, m), 5.13 (2H, s), 3.88 (3H, s), 3.19 (2H, br, d), 2.58 (4H, br, q), 0.97 (6H, t).

Intermediate 16: Methyl 7-(2-bromo-4-fluorobenzenesulfonylamino]-4H-benzo[b]pyrrolo[1,2-d][1,4]oxazine-6-carboxylate

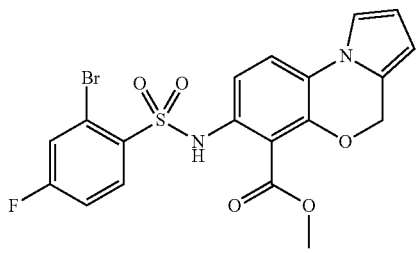 [SMILES: COC(=O)c1c(NS(=O)(=O)c2ccc(F)cc2Br)ccc2c1OCc1cccn1-2]

Methyl 7-amino-3a,4-dihydro-1H-benzo[b]pyrrolo[1,2-d][1,4]oxazine-6-carboxylate (Intermediate 17, 0.370 g) was suspended in a mixture of DCM (6 mL) and pyridine (2.43 mL) and 2-bromo-4-fluorobenzenesulfonyl chloride (0.493 g) was added. The resultant deep red solution was stirred at room temperature overnight then concentrated in vacuo. The residue was diluted with DCM and water and passed through a phase separator. The organic layer was concentrated in vacuo and the residue was purified by chromatography on silica, eluting with a mixture of ethyl acetate and cyclohexane with a gradient of 5-30% to give methyl 7-(2-bromo-4-fluorobenzenesulfonylamino]-4H-benzo[b]pyrrolo[1,2-d][1,4]oxazine-6-carboxylate (0.107 g) as a white solid.

¹H NMR (CDCl₃) δ: 9.33 (1H, s), 8.15 (1H, dd), 7.43 (1H, dd), 7.32 (1H, d), 7.24 (1H, d), 7.12 (1H, ddd), 7.04 (1H, dd), 6.32 (1H, t), 6.04 (1H, m), 5.14 (2H, d), 3.94 (3H, s).

Intermediate 17: Methyl 7-amino-3a,4-dihydro-1H-benzo[b]pyrrolo[1,2-d][1,4]oxazine-6-carboxylate

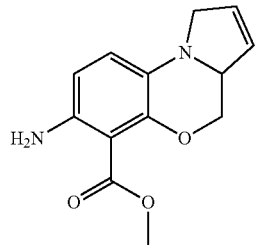 [SMILES: COC(=O)c1c(N)ccc2c1OCC1C=CCN21]

A mixture of methyl 6-amino-3-bromo-2-(2,5-dihydro-1H-pyrrol-2-ylmethoxy)-benzoate (Intermediate 18, 1.64 g), copper (I) iodide (0.095 g), L-proline (0.115 g) and potassium phosphate tribasic (2.13 g) in anhydrous DMSO (10 mL) was evacuated and purged with nitrogen then heated to 90° C., under an atmosphere of nitrogen overnight. The resultant mixture was cooled and partitioned between ethyl acetate and water. The layers were separated and the aqueous layer was extracted with more ethyl acetate. The combined organic layers were dried (MgSO$_4$) and filtered. The filtrate was concentrated in vacuo and the residue was purified by chromatography on silica, eluting with a mixture of ethyl acetate and cyclohexane with a gradient of 10-30% to give methyl 7-amino-3a,4-dihydro-1H-benzo[b]pyrrolo[1,2-d][1,4]oxazine-6-carboxylate (0.370 g) as a brown oil.

LCMS (Method A) r/t 2.19 (M+H) 247.

Intermediate 18: Methyl 6-amino-3-bromo-2-(2,5-dihydro-1H-pyrrol-2-ylmethoxy)-benzoate

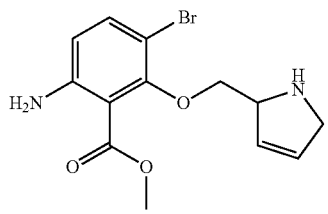 [SMILES: COC(=O)c1c(N)ccc(Br)c1OCC1C=CCN1]

TFA (5 mL) was slowly added to a suspension of tert-butyl 2-(6-bromo-3-[bis-(tert-butoxycarbonyl)amino]-2-methoxycarbonylphenoxymethyl)-2,5-dihydropyrrole-1-carboxylate (Intermediate 19, 3.55 g) in DCM (5 mL). The resultant dark solution was stirred at room temperature for 3 hours. The volatiles were removed in vacuo and the residue was partitioned between ethyl acetate and saturated aqueous potassium carbonate solution. The layers were separated and the aqueous layer was extracted with more ethyl acetate. The combined organic layers were dried (Na$_2$SO$_4$), filtered and concentrated in vacuo to give methyl 6-amino-3-bromo-2-(2,5-dihydro-1H-pyrrol-2-ylmethoxy)-benzoate (1.64 g) as a dark oil.

LCMS (Method A) r/t 1.95 (M+H) 327 and 329

Intermediate 19: tert-Butyl 2-(6-bromo-3-[bis-(tert-butoxycarbonyl)amino]-2-methoxycarbonylphenoxymethyl)-2,5-dihydropyrrole-1-carboxylate

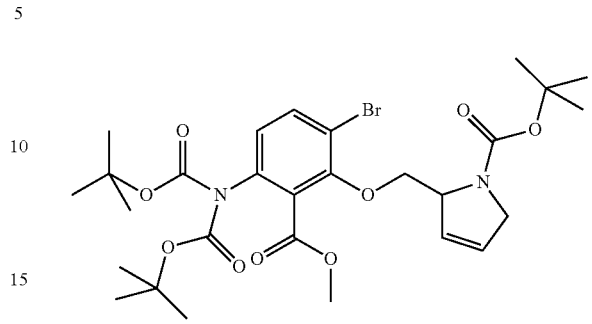

Diisopropylazodicarboxylate (1.4 g) was added to a suspension of methyl 3-bromo-6-[bis-(tert-butoxycarbonyl)amino]-2-hydroxybenzoate (Intermediate 13, 2.58 g), tert-butyl 2-hydroxymethyl-2,5-dihydropyrrole-1-carboxylate (Prepared according to Morriello et al, *Bioorg. Med. Chem,* 2008, 16(5), 2156; 1.27 g) and triphenylphosphine (1.82 g) in anhydrous THF (20 mL) and the mixture was stirred at room temperature overnight. The volatiles were removed in vacuo and the residue was purified by chromatography on silica, eluting with a mixture of ethyl acetate and cyclohexane with a gradient of 5-25% to give tert-butyl 2-(6-bromo-3-[bis-(tert-butoxycarbonyl)amino]-2-methoxycarbonylphenoxymethyl)-2,5-dihydropyrrole-1-carboxylate (4.13 g) as a light brown oil.

$^1$H NMR (CDCl$_3$) δ: 7.60 (1H, t), 6.85 (1H, m), 5.91 (2H, m), 4.81 (1H, d), 4.38-4.21 (2H, m), 3.85 (3H, d), 3.76 (1H, m), 1.86 (1H, m), 1.49 (9H, s), 1.38 (18H, m).

Intermediate 20: Methyl 8-[2-((Z)-3-diethylaminoprop-1-enyl)-4-fluorobenzenesulfonylamino]-5,6-dihydropyrazolo[5,1-a]isoquinoline-7-carboxylate

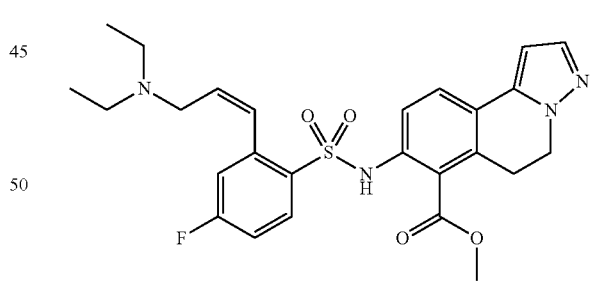

A mixture of methyl 8-(2-bromo-4-fluorobenzenesulfonylamino)-5,6-dihydropyrazolo[5,1-a]isoquinoline-7-carboxylate (Intermediate 21, 0.088 g), N,N-diethyl-N—((Z)-1-tributylstannanylprop-1-en-3-yl)-amine (Intermediate 3, 0.222 g), tris-(dibenzylideneacetone)dipalladium (0) (0.020 g) and tri-tert-butylphosphonium tetrafluoroborate (0.01 g) in dioxane (3 mL) was de-gassed and purged with nitrogen and then heated to 80° C. in a sealed vessel for 2 hours. The resultant mixture was cooled, filtered through Celite and washed with ethyl acetate. The filtrate was concentrated in vacuo and the residue was purified by chromatography on silica, eluting with a mixture of methanol and DCM with a gradient of 0-10% to give methyl 8-[2-((Z)-3-diethylaminoprop-1-enyl)-4-fluorobenzenesulfonylamino]-5,6-dihydropyrazolo[5,1-a]isoquinoline-7-carboxylate (0.057 g) as a glass.

¹H NMR (CDCl₃) δ: 8.11 (1H, dd), 7.51 (2H, m), 7.31 (1H, d), 7.13-7.07 (2H, m), 6.99 (1H, d), 6.47 (1H, d), 6.10 (1H, dt), 4.27 (2H, t), 3.96 (3H, s), 3.29 (2H, t), 3.10 (2H, d), 2.52 (4H, q), 0.94 (6H, t).

Intermediate 21: Methyl 8-(2-bromo-4-fluorobenzenesulfonylamino)-5,6-dihydropyrazolo[5,1-a]isoquinoline-7-carboxylate

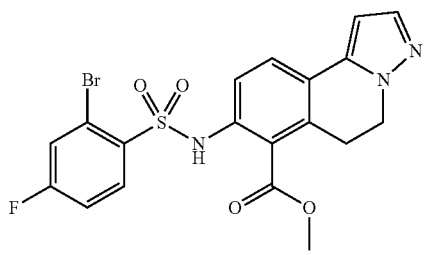 [SMILES: COC(=O)c1c(NS(=O)(=O)c2ccc(F)cc2Br)ccc2c1CCn1nccc1-2]

A mixture of methyl 8-amino-5,6-dihydropyrazolo[5,1-a]isoquinoline-7-carboxylate (Intermediate 22, 0.060 g) and 2-bromo-4-fluorobenzenesulfonyl chloride (0.081 g) in pyridine (2 mL) and DCM (4 mL) was stirred at room temperature overnight. A further amount of 2-bromo-4-fluoro-benzenesulfonyl chloride (0.010 g) was added and the reaction mixture was stirred at room temperature for 2 hours. The resultant mixture was concentrated in vacuo and the residue was dissolved in DCM and washed with 1M hydrochloric acid, dried (MgSO₄) and filtered. The filtrate was concentrated in vacuo and the residue was purified by chromatography on silica, eluting with a mixture of ethyl acetate and cyclohexane with a gradient of 0-100% to give methyl 8-(2-bromo-4-fluorobenzenesulfonylamino)-5,6-dihydropyrazolo[5,1-a]isoquinoline-7-carboxylate (0.088 g) as a glass.

¹H NMR (CDCl₃) δ: 9.31 (1H, br, s), 8.19 (1H, dd), 7.51 (3H, m), 7.43 (1H, dd), 7.14 (1H, ddd), 6.46 (1H, d), 4.26 (2H, t), 3.99 (3H, s), 3.28 (2H, t).

Intermediate 22: Methyl 8-amino-5,6-dihydropyrazolo[5,1-a]isoquinoline-7-carboxylate

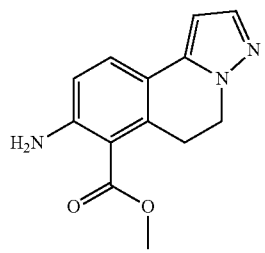 [SMILES: COC(=O)c1c(N)ccc2c1CCn1nccc1-2]

TFA (1 mL) was added to a mixture of methyl 8-[bis-(tert-butoxycarbonyl)amino]-5,6-dihydropyrazolo[5,1-a]isoquinoline-7-carboxylate and methyl 8-tert-butoxycarbonylamino-5,6-dihydropyrazolo[5,1-a]isoquinoline-7-carboxylate (Intermediate 23, 0.114 g) in DCM (2 mL) and the resultant mixture was stirred at room temperature for 1 hour. Saturated aqueous sodium bicarbonate solution was added and the mixture was stirred for 15 minutes, then extracted with DCM, dried (MgSO₄) and filtered. The filtrate was concentrated in vacuo to give methyl 8-amino-5,6-dihydropyrazolo[5,1-a]isoquinoline-7-carboxylate (0.060 g) as a gum.

¹H NMR (CDCl₃) δ: 7.48 (1H, d), 7.41 (1H, d), 6.64 (1H, d), 6.37 (1H, d), 5.16 (2H, br, s), 4.24 (2H, t), 3.93 (3H, s), 3.34 (2H, t).

Intermediate 23: Mixture of methyl 8-[bis-(tert-butoxycarbonyl)amino]-5,6-dihydropyrazolo[5,1-a]isoquinoline-7-carboxylate and methyl 8-tert-butoxycarbonylamino-5,6-dihydropyrazolo[5,1-a]isoquinoline-7-carboxylate

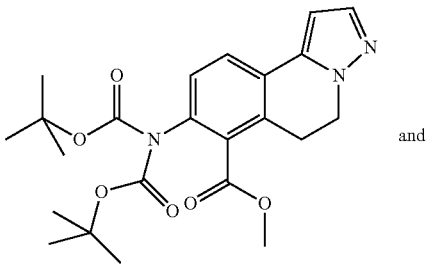

and

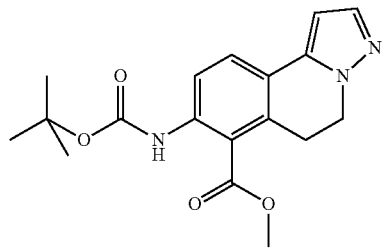

A solution of methyl 8-[bis-(tert-butoxycarbonyl)amino]-pyrazolo[5,1-a]isoquinoline-7-carboxylate (Intermediate 7, 0.36 g) in dioxane was passed through the H-Cube, using a 20% palladium hydroxide on carbon cartridge, eluting at 0.5 mL/minute, at 100° C. and 100 bar. Two fractions were isolated. The first fraction was concentrated in vacuo to give methyl 8-[bis-(tert-butoxycarbonyl)amino]-5,6-dihydropyrazolo[5,1-a]isoquinoline-7-carboxylate (0.044 g). The second fraction, containing the starting material was concentrated in vacuo then dissolved in a mixture of acetic acid in dioxane solution (20%, 40 mL) and was passed through the H-Cube®, using a 20% palladium hydroxide on carbon cartridge, eluting at 1 mL/minute, at 95° C. and 100 bar. The eluent was concentrated in vacuo and the residue purified by chromatography on silica, eluting with a mixture of ethyl acetate and cyclohexane with a gradient of 0-80% to give a solid which was combined with the earlier product to give a 3:7 mixture of methyl 8-[bis-(tert-butoxycarbonyl)amino]-5,6-dihydropyrazolo[5,1-a]isoquinoline-7-carboxylate and methyl 8-tert-butoxycarbonylamino-5,6-dihydropyrazolo[5,1-a]isoquinoline-7-carboxylate (0.084 g).

¹H NMR (CDCl₃) δ: 7.63 (1H, d), 7.56 (1H, d), 7.16 (1H, d), 6.59 (1H, d), 4.36 (2H, t), 3.90 (3H, s), 3.32 (2H, t), 1.41 (18H, s) (30%).

δ: 8.19 (1H, d), 7.62 (1H, d), 7.53 (1H, d), 6.51 (1H, d), 4.30 (2H, t), 4.00 (3H, s), 3.32 (2H, t), 1.54 (9H, s) (70%).

Intermediate 24: Methyl 7-[2-((Z)-3-diethylamino-prop-1-enyl)-4-fluorobenzenesulfonylamino]-4H-5-oxa-3,9b-diazacyclopenta[a]naphthalene-6-carboxylate

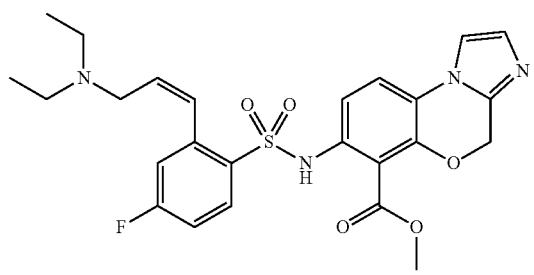 [SMILES: CCN(CC)C/C=C\c1cc(F)ccc1S(=O)(=O)Nc1ccc2c(c1C(=O)OC)OCc1nccn1-2]

A mixture of methyl 7-(2-bromo-4-fluorobenzenesulfonylamino)-4H-5-oxa-3,9b-diazacyclopenta[a]naphthalene-6-carboxylate (Intermediate 25, 0.598 g), N,N-diethyl-N—((Z)-1-tributylstannanylprop-1-en-3-yl)-amine (Intermediate 3, 0.997 g), tris-(dibenzylideneacetone)dipalladium (0) (0.057 g) and tri-tert-butylphosphonium tetrafluoroborate (0.036 g) in dioxane (15 mL) and DMSO (1.5 mL) was de-gassed and purged with nitrogen then heated to 95° C. under an atmosphere of nitrogen for 2 hours. Further amounts of tris-(dibenzylideneacetone)dipalladium (0) (0.057 g) and tri-tert-butylphosphonium tetrafluoroborate (0.036 g) were added and the mixture stirred and heated at 95° C. for 2 hours. Further amounts of N,N-diethyl-N—((Z)-1-tributylstannanylprop-1-en-3-yl)-amine (Intermediate 3, 0.997 g), tris-(dibenzylideneacetone)dipalladium (0) (0.057 g) and tri-tert-butylphosphonium tetrafluoroborate (0.036 g) were added and the mixture was stirred and heated at 95° C. for 30 minutes. After cooling, the mixture was diluted with ethyl acetate and washed with water, dried (Na₂SO₄) and filtered. The filtrate was concentrated in vacuo and the residue was purified by chromatography on silica, eluting with a mixture of methanol and DCM with a gradient of 0-30% to give methyl 7-[2-((Z)-3-diethylaminoprop-1-enyl)-4-fluorobenzenesulfonylamino]-4H-5-oxa-3,9b-diaza-cyclopenta[a]naphthalene-6-carboxylate (0.158 g) as a light brown foam.

¹H NMR (CDCl₃) δ: 8.10 (1H, dd), 7.27 (1H, d), 7.25 (1H, d), 7.17 (1H, d), 7.16-7.06 (3H, m), 6.97 (1H, d), 6.06 (1H, dt), 5.28 (2H, s), 3.93 (3H, s), 3.04 (2H, d), 2.45 (4H, q), 0.91 (6H, t).

Intermediate 25: Methyl 7-(2-bromo-4-fluorobenzenesulfonylamino)-4H-5-oxa-3,9b-diazacyclopenta[a]naphthalene-6-carboxylate

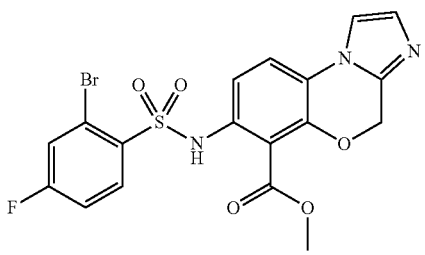 [SMILES: COC(=O)c1c(NS(=O)(=O)c2ccc(F)cc2Br)ccc2c1OCc1nccn1-2]

A mixture of methyl 7-amino-4H-5-oxa-3,9b-diazacyclopenta[a]naphthalene-6-carboxylate (Intermediate 26, 0.379 g) and 2-bromo-4-fluorobenzenesulfonyl chloride (0.466 g) in pyridine (10 mL) and DCM (10 mL) was stirred at room temperature for 17 hours. A further amount of 2-bromo-4-fluorobenzenesulfonyl chloride (0.190 g) was added and the mixture was stirred at room temperature for 5 hours. The resultant mixture was concentrated in vacuo and the residue was dissolved in DCM and water and passed through a phase separator. The filtrate was concentrated in vacuo and the residue was purified by chromatography on silica, eluting with ethyl acetate to give a white solid which was triturated with ether to give methyl 7-(2-bromo-4-fluorobenzenesulfonylamino)-4H-5-oxa-3,9b-diazacyclopenta[a]naphthalene-6-carboxylate (0.603 g) as an off-white solid.

¹H NMR (CDCl₃) δ: 9.57 (1H, br, s), 8.18 (1H, dd), 7.44 (1H, dd), 7.33-7.25 (3H, m), 7.18-7.11 (2H, m), 5.29 (2H, s), 3.97 (3H, s).

Intermediate 26: Methyl 7-amino-4H-5-oxa-3,9b-diazacyclopenta[a]naphthalene-6-carboxylate

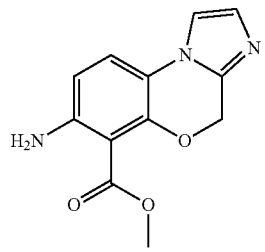 [SMILES: COC(=O)c1c(N)ccc2c1OCc1nccn1-2]

A solution of methyl 7-amino-3-(2,2-dimethoxyethylamino)-2H-benzo[1,4]oxazine-8-carboxylate (Intermediate 27, 0.910 g) in concentrated aqueous hydrochloric acid (8 mL) and methanol (10 mL) was heated to reflux for 3 hours. After cooling, the mixture was concentrated in vacuo and the residue was dissolved in a mixture of ethyl acetate and water and basified with 2M aqueous sodium hydroxide solution. The layers were separated and the aqueous layer was extracted several times with ethyl acetate. The combined organic layers were dried (Na$_2$SO$_4$) and filtered. The filtrate was concentrated in vacuo and the residue was purified by chromatography on silica, eluting with a mixture of ethyl acetate and cyclohexane with a gradient of 50-100% and then a mixture of methanol and ethyl acetate (5%) to give methyl 7-amino-4H-5-oxa-3,9b-diazacyclopenta[a]naphthalene-6-carboxylate (0.383 g) as a sandy coloured solid.

$^1$H NMR (DMSO-d$_6$) δ: 7.76 (1H, d), 7.52 (1H, d), 7.06 (1H, d), 6.50 (1H, d), 5.94 (2H, br, s), 5.23 (2H, s), 3.81 (3H, s).

Intermediate 27: Methyl 7-amino-3-(2,2-dimethoxyethylamino)-2H-benzo[1,4]oxazine-8-carboxylate

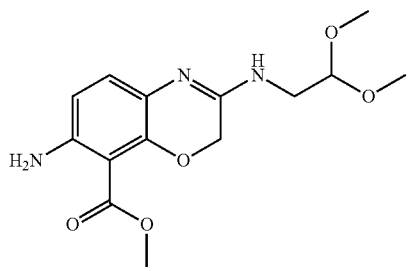 [SMILES: COC(=O)c1c(N)ccc2c1OCC(NCC(OC)OC)=N2]

A solution of methyl 7-amino-3-methylsulfanyl-2H-benzo[1,4]oxazine-8-carboxylate (Intermediate 28, 0.645 g) and aminoacetaldehyde dimethylacetal (0.403 g) in ethanol (15 mL) was heated to reflux for 4 days. After cooling, the mixture was concentrated in vacuo to give methyl 7-amino-3-(2,2-dimethoxyethylamino)-2H-benzo[1,4]oxazine-8-carboxylate (0.910 g) as a brown oil.

LCMS (Method A) r/t 1.82 (M+H) 310

Intermediate 28: Methyl 7-amino-3-methylsulfanyl-2H-benzo[1,4]oxazine-8-carboxylate

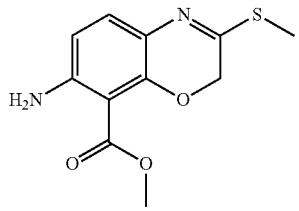 [SMILES: COC(=O)c1c(N)ccc2c1OCC(SC)=N2]

A mixture of methyl 7-amino-3-thioxo-3,4-dihydro-2H-benzo[1,4]oxazine-8-carboxylate (Intermediate 29, 0.795 g), methyl iodide (0.710 g) and potassium carbonate (1.38 g) in acetone (20 mL) was stirred at room temperature for 2 hours. The resultant mixture was filtered and the filtrate was concentrated in vacuo. The residue was purified by chromatography on silica, eluting with a mixture of ethyl acetate and cyclohexane with a gradient of 5-25% to give methyl 7-amino-3-methylsulfanyl-2H-benzo[1,4]oxazine-8-carboxylate (0.648 g) as a sandy coloured solid.

LCMS (Method A) r/t 3.26 (M+H) 253

Intermediate 29: Methyl 7-amino-3-thioxo-3,4-dihydro-2H-benzo[1,4]oxazine-8-carboxylate

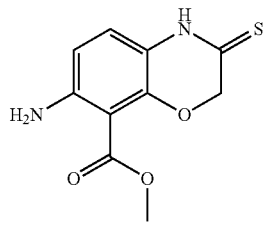 [SMILES: COC(=O)c1c(N)ccc2c1OCC(=S)N2]

A mixture of methyl 7-amino-3-oxo-3,4-dihydro-2H-benzo[1,4]oxazine-8-carboxylate (Intermediate 30, 1.187 g) and Lawesson's reagent (1.08 g) in anhydrous THF (20 mL) was heated to 60° C., under an atmosphere of nitrogen for 40 minutes. After cooling, the mixture was diluted with cyclohexane and purified by chromatography on silica, eluting with a mixture of ethyl acetate and cyclohexane with a gradient of 10-50%. The resultant material was triturated with ether to give a yellow solid (0.795 g). The filtrate from the trituration was concentrated in vacuo and the residue was re-purified by chromatography on silica, eluting with a mixture of ethyl acetate and cyclohexane with a gradient of 10-50%. The resultant material was triturated with ether to give a further amount of a yellow solid (0.051 g). The two batches of yellow solid were combined to give methyl 7-amino-3-thioxo-3,4-dihydro-2H-benzo[1,4]oxazine-8-carboxylate (0.846 g).

$^1$H NMR (DMSO-d$_6$) δ: 12.52 (1H, br, s), 6.96 (1H, d), 6.39 (1H, d), 6.06 (2H, br, s), 4.72 (2H, s), 3.78 (3H, s).

Intermediate 30: Methyl 7-amino-3-oxo-3,4-dihydro-2H-benzo[1,4]oxazine-8-carboxylate

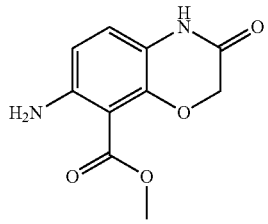

A mixture of methyl 6-amino-3-bromo-2-carbamoylmethoxybenzoate (Intermediate 31, 5.64 g), N,N'-dimethylethylenediamine (1.64 g), copper (I) iodide (3.55 g) and potassium carbonate (5.13 g) in N-methylpyrrolidone (50 mL) was heated to 140° C., under an atmosphere of nitrogen for 1 hour. After cooling, the mixture was diluted with ethanol (400 mL) and filtered through Celite. The filtrate was concentrated in vacuo and the residue was dissolved in ethyl acetate and water and filtered through Celite again. The layers were separated and the aqueous layer was extracted with ethyl acetate (ten times). The combined organic layers were washed with water, dried (Na$_2$SO$_4$) and filtered. The filtrate was concentrated in vacuo and the residue was triturated with ether to give an orange/brown solid (1.10 g). The filtrate from the trituration was concentrated in vacuo and the residue was purified by chromatography on silica, eluting with a mixture of ethyl acetate and cyclohexane with a gradient of 30-100%. The product obtained was triturated with diethyl ether to give a pale yellow solid (0.28 g). The two batches of solid were combined to give methyl 7-amino-3-oxo-3,4-dihydro-2H-benzo[1,4]oxazine-8-carboxylate (1.38 g).

$^{1}$H NMR (DMSO-$d_6$) δ: 10.36 (1H, br, s), 6.76 (1H, d), 6.36 (1H, d), 5.68 (2H, br, s), 4.47 (2H, s), 3.77 (3H, s).

Intermediate 31: Methyl 6-amino-3-bromo-2-carbamoylmethoxybenzoate

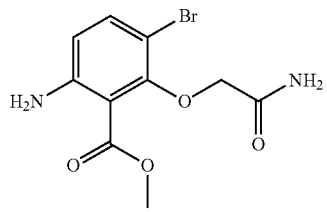 [SMILES: COC(=O)c1c(N)ccc(Br)c1OCC(N)=O]

A mixture of methyl 6-amino-3-bromo-2-hydroxybenzoate (prepared according to Wang et al, *Bioorg Med Chem Lett*, 2007, 17, 2817, 7.55 g), bromoacetamide (4.55 g) and potassium carbonate (10.0 g) in DMF (70 mL) was heated to 60° C. for 17 hours. After cooling, the mixture was concentrated in vacuo and the residue was dissolved in ethyl acetate and water and the layers were separated. The aqueous layer was extracted with ethyl acetate and the combined organic layers were dried ($Na_2SO_4$) and filtered. The filtrate was concentrated in vacuo to give an orange solid which was triturated with ether to give methyl 6-amino-3-bromo-2-carbamoylmethoxybenzoate (5.81 g) as a sandy coloured solid.

$^{1}$H NMR (CDCl$_3$) δ: 7.36 (1H, d), 6.43 (1H, d), 5.36 (2H, br, s), 4.49 (2H, s), 3.90 (3H, s).

Biological Example

Compounds are tested for their capacity to inhibit recombinant human MetAP2 activity using the following assay.

Human recombinant MetAP2 expressed in Sf9 cells followed by affinity purification and EDTA treatment to remove endogenous active site cation was dialysed against MnCl$_2$ to produce the manganese enzyme used in the assay. The assay was carried out for 30 minutes at 25° C. in 50 mM HEPES buffer containing 100 mM NaCl, pH 7.5 the presence of 0.75 mM Methionine-Alanine-Serine (MAS) substrate and 50 μg/ml amino acid oxidase using a dilution of purified MetAP2 giving>3-fold signal: noise. Cleavage of the substrate by MetAP2 and oxidation of free methionine by amino acid oxidase was detected and quantified using fluorescence generated by Amplex red (10-acetyl-3,7-dihydroxyphenoxazine) in combination with horseradish peroxidase which detects $H_2O_2$ released during the oxidation step. The fluorescent signal was detected using a multiwell fluorimeter. Compounds were diluted in DMSO prior to addition to assay buffer, the final DMSO concentration in the assay being 1%.

The IC$_{50}$ is defined as the concentration at which a given compound achieves 50% inhibition of control. IC$_{50}$ values are calculated using the XLfit software package (version 2.0.5).

Compounds of the invention demonstrated activity in the assay of this Example as indicated in the following table, wherein A represents IC$_{50}$<0.05 μM, B represents IC$_{50}$ between 0.05 μM and 0.5 μM, and C represents IC$_{50}$>0.5 μM.

| Compound name | Activity |
|---|---|
| 8-[2-((Z)-3-Diethylaminoprop-1-enyl)-4-fluorobenzenesulfonyl-amino]-pyrazolo[5,1-a]isoquinoline-7-carboxylic acid | A |
| 7-[2-((Z)-3-Diethylaminoprop-1-enyl)-4-fluorobenzenesulfonyl-amino]-4H-benzo[b]pyrrolo[1,2-d][1,4]oxazine-6-carboxylic acid | A |
| 8-[2-((Z)-3-Diethylaminoprop-1-enyl)-4-fluorobenzenesulfonyl-amino]-5,6-dihydropyrazolo[5,1-a]isoquinoline-7-carboxylic acid | B |
| 7-[2-((Z)-3-Diethylaminoprop-1-enyl)-4-fluorobenzenesulfonyl-amino]-4H-5-oxa-3,9b-diazacyclopenta[a]naphthalene-6-carboxylic acid | A |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A tricyclic compound represented by:

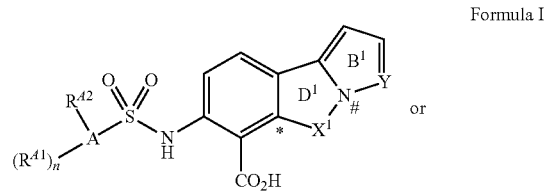

Formula I

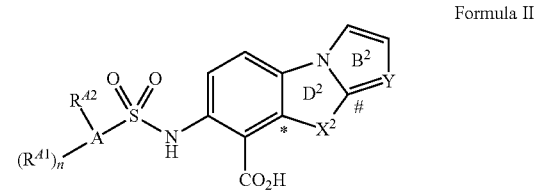

Formula II wherein:
D$^1$ and D$^2$ are each 6-7 membered heterocyclic or heteroaromatic rings in which one of the two atoms in common between rings B and D is nitrogen and the other is carbon;

$X^1$ is selected from the group consisting of: *—C($R^{D1}R^{D2}$)—C($R^{D5}R^{D6}$)—#, *—C($R^{C1}$)=C($R^{C2}$)—#, and *—C($R^{D1}R^{D2}$)—C($R^{D3}R^{D4}$)—C($R^{D5}R^{D6}$)—#; wherein the * and # denote the attachment points of $X^1$ in Formula I;

$X^2$ is selected from the group consisting of: *—$W^1$—C($R^{D5}R^{D6}$)—#, *—$W^1$C($R^{D3}R^{D4}$)—C($R^{D5}R^{D6}$)—#, and *—C($R^{D1}R^{D2}$)—$W^2$—C($R^{D5}R^{D6}$)—#; wherein the * and # indicate the attachment points of $X^2$ in Formula II;

Y is N in formula I, and Y is selected from CH or N in formula II;

$B^1$ or $B^2$ rings are each optionally be substituted by one or more fluorine atoms on any of the available carbon atoms;

$W^1$ is O;

$W^2$ is O;

A is phenyl;

$R^{A1}$ is selected, independently for each occurrence, from the group consisting of: hydrogen, hydroxyl, cyano, halogen, $C_{1-4}$alkyl or $C_{1-3}$alkoxy; wherein $C_{1-4}$alkyl, or $C_{1-3}$alkoxy may be optionally substituted by one or more fluorines;

n is 1 or 2;

$R^{A2}$ is selected from the group consisting of: hydrogen, $R^iR^jN$—, heterocyclyl, heterocyclyloxy, heterocyclyl-($NR^a$)—; wherein said heterocyclyl may optionally be substituted by one or more substituents selected from $R^g$ and wherein if said heterocyclyl contains a —NH moiety that nitrogen may optionally be substituted by one or more groups $R^h$; or $R^{A2}$ is selected from the group consisting of: $C_{1-6}$alkyl, $C_{2-6}$alkenyl, $C_{2-6}$alkynyl, $C_{3-6}$ cycloalkyl, $C_{1-6}$alkoxy, $C_{3-6}$alkenyloxy, $C_{3-6}$alkynyloxy, $C_{3-6}$cycloalkoxy, $C_{1-6}$alkyl S(O)$_w$— (wherein w is 0, 1 or 2), $C_{1-6}$alkyl-N($R^a$)—, $C_{1-6}$alkyl-N($R^a$)-carbonyl-, $C_{1-6}$alkylcarbonyl-N($R^a$)—, $C_{1-6}$alkyl-N($R^a$)-carbonyl-N($R^a$)—, $C_{1-6}$alkyl-N($R^a$)—SO$_2$—, $C_{1-6}$alkyl-SO$_2$—N($R^a$)—, $C_{1-6}$alkoxycarbonyl-N($R^a$)—, $C_{1-6}$alkylcarbonyl-N($R^a$)—$C_{1-6}$alkyl-, $C_{1-6}$alkyl-N($R^a$)-carbonyl-$C_{1-6}$alkyl-, $C_{1-6}$ alkoxy$C_{1-6}$alkyl-; wherein $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— (wherein w is 0, 1 or 2), $C_{1-6}$alkyl-N($R^a$)—, $C_{1-6}$alkyl-N($R^a$)-carbonyl-, $C_{1-6}$alkylcarbonyl-N($R^a$)—, $C_{1-6}$alkyl-N($R^a$)-carbonyl-N($R^a$)—, $C_{1-6}$alkyl-N($R^a$)—SO$_2$—, $C_{1-6}$alkyl-SO$_2$—N($R^a$)—, $C_{1-6}$alkoxycarbonyl-N($R^a$)—, $C_{1-6}$alkylcarbonyl-N($R^a$)$C_{1-6}$alkyl-, $C_{1-6}$alkyl-N($R^a$)-carbonyl-$C_{1-6}$alkyl-, $C_{1-6}$alkoxy-$C_{1-6}$alkyl may optionally be substituted by $R^P$, phenyl, phenoxy, heteroaryl, heteroaryloxy, heteroaryl-(N$R^a$)—, heterocyclyl, heterocyclyloxy or heterocyclyl-N($R^a$)—; wherein said heteroaryl or phenyl may optionally be substituted with one or more substituents selected from $R^f$; wherein said heterocyclyl may optionally be substituted by one or more substituents selected from $R^g$; and wherein if said heterocyclyl contains a —NH moiety that nitrogen may optionally be substituted by one or more groups $R^h$;

$R^{D1}$ and $R^{D2}$ are each independently selected from the group consisting of: hydrogen, fluorine, hydroxyl, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano or hydroxyl;

$R^{D3}$ and $R^{D4}$ are each independently selected from the group consisting of: hydrogen, fluorine, hydroxyl, cyano, $C_{1-2}$alkyl or $C_{1-2}$alkoxy; wherein the $C_{1-3}$ alkyl and $C_{1-3}$ alkoxy may optionally be substituted by one or more fluorine atoms or a group selected from cyano, hydroxyl or N($R^aR^b$);

$R^{D5}$ and $R^{D6}$ are each independently selected from the group consisting of: hydrogen, fluorine, hydroxyl, cyano, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano, hydroxyl or N($R^aR^b$), $R^{C1}$ is selected from the group consisting of: hydrogen, halogen, $C_{1-2}$alkyl or $C_{1-2}$alkoxy; wherein the $C_{1-2}$alkyl or $C_{1-2}$alkoxy may optionally be substituted by one or more fluorine atoms;

$R^{C2}$ is selected from the group consisting of: hydrogen, halogen, hydroxyl, cyano, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano, hydroxyl or N($R^aR^b$);

$R^a$ and $R^b$ are independently selected, for each occurrence, from the group consisting of: hydrogen and $C_{1-3}$alkyl; wherein $C_{1-3}$alkyl may optionally be substituted by one or more substituents selected from: fluorine, cyano, oxo and hydroxyl;

or $R^a$ and $R^b$, together with the nitrogen to which they are attached, form a 4-6 membered heterocyclic ring which may have an additional heteroatom selected from O, S, or N; and wherein the 4-6 membered heterocyclic ring may optionally be substituted on carbon by one or more substituents selected from the group consisting of: fluorine, cyano, oxo or hydroxyl;

$R^f$ is independently selected, for each occurrence, from the group consisting of: $R^P$, hydrogen, $C_{1-6}$alkyl, $C_{3-6}$cycloalkyl, $C_{2-6}$alkenyl, $C_{2-6}$alkynyl, $C_{3-6}$cycloalkyl, $C_{1-6}$alkoxy, $C_{1-6}$alkyl-S(O)$_w$— (wherein w is 0, 1 or 2), $C_{1-6}$alkylcarbonyl-N($R^a$)—; $C_{1-6}$alkoxycarbonyl-N($R^a$)—; and wherein $C_{1-6}$alkyl, $C_{3-6}$cycloalkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N($R^a$)—, $C_{1-6}$alkoxycarbonyl-N($R^a$)— may be optionally substituted by one or more substituents selected from $R^P$;

$R^g$ is independently selected for each occurrence from the group consisting of: $R^P$, hydrogen, oxo, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl S(O)$_w$— (wherein w is 0, 1 or 2), $C_{1-6}$alkyl-carbonyl-N($R^a$)—; $C_{1-6}$alkoxycarbonyl-N($R^a$)—; wherein $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N($R^a$)—, $C_{1-6}$alkoxycarbonyl-N($R^a$)— may be optionally substituted by one or more substituents selected from $R^P$;

$R^h$ is independently selected for each occurrence from the group consisting of: hydrogen, $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkoxycarbonyl-, $R^iR^j$N-carbonyl-, $R^iR^j$N—SO$_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkylcarbonyl- may optionally be substituted by one or more substituents selected from $R^P$;

$R^i$ and $R^j$, are selected independently for each occurrence from the group consisting of: hydrogen, $C_{1-4}$alkyl and $C_{3-6}$cycloalkyl; wherein $C_{1-4}$alkyl and $C_{3-6}$cycloalkyl may be optionally substituted by one or more substituents selected from fluorine, hydroxyl, cyano, $R^aR^b$N—, $R^aR^b$N-carbonyl-, $C_{1-3}$ alkoxy;

or $R^i$ and $R^j$ taken together with the nitrogen to which they are attached form a 4-7 membered heterocyclic ring which may have an additional heteroatom selected from O, S, or N, optionally substituted on carbon by one or more substituents selected from the group consisting of: fluorine, hydroxyl, oxo, cyano, $C_{1-6}$alkyl, $C_{1-6}$alkoxy, $R^aR^bN$—, $R^aR^bN$—$SO_2$—, $R^aR^bN$-carbonyl-; and wherein said $C_{1-6}$alkyl or $C_{1-6}$alkoxy may optionally be substituted by fluorine, hydroxyl or cyano; and optionally substituted on nitrogen by one or more substituents selected from the group consisting of: $C_{1-6}$alkyl, $R^aR^bN$-carbonyl-; and wherein said $C_{1-6}$alkyl may be optionally substituted by fluorine, hydroxyl, cyano;

$R^P$ is independently selected, for each occurrence, from the group consisting of: halogen, hydroxyl, cyano, $C_{1-6}$alkoxy, $R^iR^jN$—, $R^iR^jN$-carbonyl-, $R^iR^jN$—$SO_2$—, $R^iR^jN$-carbonyl-$N(R^a)$—;

and pharmaceutically acceptable salts, stereoisomers, esters and prodrugs thereof.

2. The tricyclic compound of claim 1, wherein $X^1$ is selected from the group consisting of: *—$C(R^{D1}R^{D2})$—$C(R^{D5}R^{D6})$—# and *—$C(R^{C1})$=$C(R^{C2})$—#; wherein the * and # indicate the attachment points of $X^1$ as indicated in Formula I.

3. The tricyclic compound of claim 1, wherein $X^1$ is selected from the group consisting of: *—$CH_2CH_2$—# and *—$CH=CH^\#$; wherein the * and # indicate the attachment points of $X^1$ as indicated in Formula I.

4. The tricyclic compound of claim 1, wherein $X^2$ is *—O—$C(R^{D5}R^{D6})$—#; wherein the * and # indicate the attachment points of $X^2$ as indicated in Formula II.

5. The tricyclic compound of claim 4, wherein $X^2$ is *—O—$CH_2$—#; wherein the * and # indicate the attachment points of $X^1$ as indicated in Formula II.

6. The tricyclic compound of claim 4, wherein $R^{D1}$, $R^{D2}$, and $R^{C1}$ are independently selected for each occurrence from the group consisting of hydrogen and methyl.

7. The tricyclic compound of claim 4, wherein $R^{D1}$, $R^{D2}$, and $R^{C1}$ are hydrogen.

8. The tricyclic compound of claim 1, wherein $R^{D3}$, $R^{D4}$, $R^{D5}$ and $R^{D6}$ are independently selected for each occurrence from the group consisting of hydrogen, fluorine, cyano, or $C_{1-2}$alkyl.

9. The tricyclic compound of claim 8, wherein $R^{D3}$, $R^{D4}$, $R^{D5}$ and $R^{D6}$ are hydrogen.

10. The tricyclic compound of claim 1, wherein $R^{C2}$ is selected from the group consisting of hydrogen, halogen, cyano or $C_{1-2}$alkyl.

11. The tricyclic compound of claim 1, wherein $R^{C2}$ is hydrogen.

12. The tricyclic compound of claim 1, wherein the compound is selected from the group consisting of:

13. A tricyclic compound represented by:

Formula III

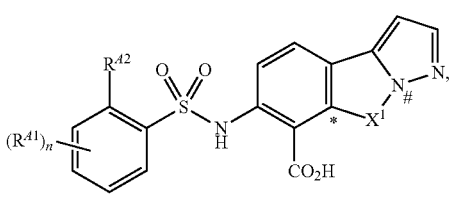

Formula IV

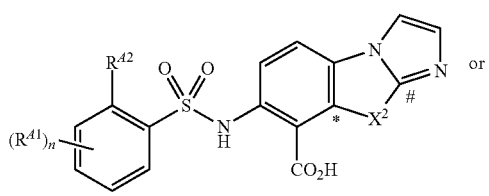

or

Formula V

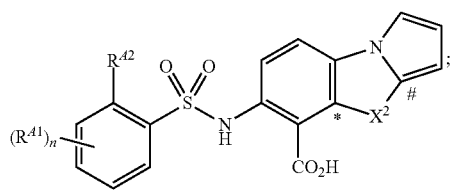

wherein $X^1$ is selected from the group consisting of: *—C($R^{D1}R^{D2}$)—#, *—C($R^{D1}R^{D2}$)—C($R^{D5}R^{D6}$)—#, *—C($R^{C1}$)=C($R^{C2}$)—#, and *—C($R^{D1}R^{D2}$)—C($R^{D3}R^{D4}$)—C($R^{D5}R^{D6}$)—#; wherein the * and # denote the attachment points of $X^1$ in Formula I;

$X^2$ is selected from the group consisting of: *—$W^1$—C($R^{D5}R^{D6}$)—#, *—$W^1$—($R^{D3}R^{D4}$)—C($R^{D5}R^{D6}$)—#, and *—C($R^{D1}R^{D2}$)—$W^2$—C($R^{D5}R^{D6}$)—#; wherein the * and # indicate the attachment points of $X^2$ in Formula II;

Y is N in formula I, and Y is selected from CH or N in formula II;

$B^1$ or $B^2$ rings are each optionally be substituted by one or more fluorine atoms on any of the available carbon atoms;

$W^1$ is O;

$W^2$ is O;

$R^{A1}$ is selected, independently for each occurrence, from the group consisting of: hydrogen, hydroxyl, cyano, halogen, $C_{1-4}$alkyl or $C_{1-3}$alkoxy; wherein $C_{1-4}$alkyl, or $C_{1-3}$alkoxy may be optionally substituted by one or more fluorines;

n is 1 or 2;

$R^{A2}$ is selected from the group consisting of: hydrogen, $R^i R^j N$—, heterocyclyl, heterocyclyloxy, heterocyclyl-(N$R^a$)—; wherein said heterocyclyl may optionally be substituted by one or more substituents selected from $R^g$ and wherein if said heterocyclyl contains a —NH moiety that nitrogen may optionally be substituted by one or more groups $R^h$; or $R^{A2}$ is selected from the group consisting of: $C_{1-6}$alkyl, $C_{2-6}$alkenyl, $C_{2-6}$alkynyl, $C_{3-6}$ cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— (wherein w is 0, 1 or 2), $C_{1-6}$alkyl-N($R^a$)—, $C_{1-6}$alkyl-N($R^a$)-carbonyl-, $C_{1-6}$alkylcarbonyl-N($R^a$)—, $C_{1-6}$alkyl-N($R^a$)-carbonyl-N($R^a$)—, $C_{1-6}$alkyl-N($R^a$)—$SO_2$—, $C_{1-6}$alkyl-$SO_2$—N($R^a$)—, $C_{1-6}$alkoxycarbonyl-N($R^a$)—, $C_{1-6}$alkylcarbonyl-N($R^a$)—$C_{1-6}$alkyl-, $C_{1-6}$alkyl-N($R^a$)-carbonyl-$C_{1-6}$ alkyl-, $C_{1-6}$alkoxy$C_{1-6}$alkyl-; wherein $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$—, $C_{1-6}$alkyl-N($R^a$)—, $C_{1-6}$alkyl-N($R^a$)-carbonyl-, $C_{1-6}$alkylcarbonyl-N($R^a$)—, $C_{1-6}$alkyl-N($R^a$)-carbonyl-N($R^a$)—, $C_{1-6}$alkyl-N($R^a$)—$SO_2$—, $C_{1-6}$alkyl-$SO_2$—N($R^a$)—, $C_{1-6}$alkoxycarbonyl-N($R^a$)—, $C_{1-6}$alkylcarbonyl-N($R^a$)$C_{1-6}$alkyl-, $C_{1-6}$alkyl-N($R^a$)-carbonyl-$C_{1-6}$alkyl-, $C_{1-6}$alkoxy-$C_{1-6}$alkyl may optionally be substituted by $R^p$, phenyl, phenoxy, heteroaryl, heteroaryloxy, heteroaryl-(NR')-, heterocyclyl, heterocyclyloxy or heterocyclyl-N($R^a$)—; wherein said heteroaryl or phenyl may optionally be substituted with one or more substituents selected from $R^f$; wherein said heterocyclyl may optionally be substituted by one or more substituents selected from $R^g$; and wherein if said heterocyclyl contains a —NH moiety that nitrogen may optionally be substituted by one or more groups $R^h$;

$R^{D1}$ and $R^{D2}$ are each independently selected from the group consisting of: hydrogen, fluorine, hydroxyl, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano or hydroxyl;

$R^{D3}$ and $R^{D4}$ are each independently selected from the group consisting of: hydrogen, fluorine, hydroxyl, cyano, $C_{1-3}$alkyl or $C_{1-3}$alkoxy; wherein the $C_{1-3}$ alkyl and $C_{1-3}$ alkoxy may optionally be substituted by one or more fluorine atoms or a group selected from cyano, hydroxyl or N($R^a R^b$);

$R^{D5}$ and $R^{D6}$ are each independently selected from the group consisting of: hydrogen, fluorine, hydroxyl, cyano, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano, hydroxyl or N($R^a R^b$), $R^{C1}$ is selected from the group consisting of: hydrogen, halogen, $C_{1-2}$alkyl or $C_{1-2}$alkoxy; wherein the $C_{1-2}$alkyl or $C_{1-2}$alkoxy may optionally be substituted by one or more fluorine atoms;

$R^{C2}$ is selected from the group consisting of: hydrogen, halogen, hydroxyl, cyano, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano, hydroxyl or N($R^a R^b$);

$R^{N1}$ is selected from the group consisting of: hydrogen or $C_{1-2}$alkyl;

$R^{N2}$ is selected from the group consisting of: hydrogen, $C_{1-3}$alkyl or $C_{1-2}$alkylcarbonyl; wherein the $C_{1-3}$alkyl and $C_{1-2}$alkylcarbonyl may optionally be substituted by one or more fluorine atoms or a group selected from cyano, hydroxyl or N($R^a R^b$);

$R^a$ and $R^b$ are independently selected, for each occurrence, from the group consisting of: hydrogen and $C_{1-3}$alkyl; wherein $C_{1-3}$alkyl may optionally be substituted by one or more substituents selected from: fluorine, cyano, oxo and hydroxyl;

or $R^a$ and $R^b$, together with the nitrogen to which they are attached, may form a 4-6 membered heterocyclic ring which may have an additional heteroatom selected from O, S, or N; and wherein the 4-6 membered heterocyclic ring may optionally be substituted on carbon by one or more substituents selected from the group consisting of: fluorine, cyano, oxo or hydroxyl;

$R^f$ is independently selected, for each occurrence, from the group consisting of: $R^P$, hydrogen, $C_{1-6}$alkyl, $C_{3-6}$cycloalkyl, $C_{2-6}$alkenyl, $C_{2-6}$alkynyl, $C_{3-6}$cycloalkyl, $C_{1-6}$alkoxy, $C_{1-6}$alkyl-S(O)$_w$— (wherein w is 0, 1 or 2), $C_{1-6}$alkylcarbonyl-N(R$^a$)—; $C_{1-6}$alkoxycarbonyl-N(R$^a$)—; and wherein $C_{1-6}$alkyl, $C_{3-6}$cycloalkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N(R$^a$)—, $C_{1-6}$alkoxycarbonyl-N(R$^a$)— may be optionally substituted by one or more substituents selected from $R^P$;

$R^g$ is independently selected for each occurrence from the group consisting of: $R^P$, hydrogen, oxo, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$— (wherein w is 0, 1 or 2), $C_{1-6}$alkylcarbonyl-N(R$^a$)—, $C_{1-6}$alkoxycarbonyl-N(R$^a$)—; wherein $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$alkylcarbonyl-N(R$^a$)—, $C_{1-6}$alkoxycarbonyl-N(R$^a$)— may be optionally substituted by one or more substituents selected from $R^P$;

$R^h$ is independently selected for each occurrence from the group consisting of: hydrogen, $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkoxycarbonyl-, R$^i$R$^j$N-carbonyl-, R$^i$R$^j$N—SO$_2$—; wherein $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkylcarbonyl- may optionally be substituted by one or more substituents selected from $R^P$;

R$^i$ and R$^j$ are selected independently for each occurrence from the group consisting of: hydrogen, $C_{1-4}$alkyl and $C_{3-6}$cycloalkyl; wherein $C_{1-4}$alkyl and $C_{3-6}$cycloalkyl may be optionally substituted by one or more substituents selected from fluorine, hydroxyl, cyano, R$^a$R$^b$N—, R$^a$R$^b$N— carbonyl-, $C_{1-3}$ alkoxy;

or R$^i$ and R$^j$ taken together with the nitrogen to which they are attached form a 4-7 membered heterocyclic ring which may have an additional heteroatom selected from O, S, or N, optionally substituted on carbon by one or more substituents selected from the group consisting of: fluorine, hydroxyl, oxo, cyano, $C_{1-6}$alkyl, $C_{1-6}$alkoxy, R$^a$R$^b$N—, R$^a$R$^b$N—SO$_2$—, R$^a$R$^b$N-carbonyl-; and wherein said $C_{1-6}$alkyl or $C_{1-6}$alkoxy may optionally be substituted by fluorine, hydroxyl or cyano; and optionally substituted on nitrogen by one or more substituents selected from the group consisting of: $C_{1-6}$alkyl, R$^a$R$^b$N-carbonyl-; and wherein said $C_{1-6}$alkyl may be optionally substituted by fluorine, hydroxyl, cyano;

$R^P$ is independently selected, for each occurrence, from the group consisting of: halogen, hydroxyl, cyano, $C_{1-6}$alkoxy, R$^i$R$^j$N—, R$^i$R$^j$N-carbonyl-, R$^i$R$^j$N—SO$_2$—, R$^i$R$^j$N-carbonyl-N(R$^a$)—;

and pharmaceutically acceptable salts, stereoisomers, esters and prodrugs thereof.

14. The tricyclic compound of claim 13, wherein R$^{41}$ is selected from the group consisting of hydrogen, halogen, $C_{1-2}$alkyl, $C_{1-2}$alkoxy; wherein $C_{1-2}$alkyl may optionally be substituted by one or more fluorines.

15. The tricyclic compound of claim 13, wherein R$^{41}$ is selected from hydrogen or fluorine.

16. The tricyclic compound of claim 13, wherein R$^{42}$ is selected from the group consisting of hydrogen, R$^i$R$^j$N, heterocyclyl, $C_{1-6}$alkyl, $C_{3-6}$alkenyl, $C_{3-6}$cycloalkyl, $C_{1-6}$alkoxy; wherein said heterocyclyl may optionally be substituted by one or more groups R$^g$, and wherein if said heterocyclyl contains a —NH moiety, that nitrogen may optionally be substituted by on or more groups R$^h$; and wherein said $C_{1-6}$alkyl, $C_{3-6}$alkenyl, $C_{3-6}$cycloalkyl and $C_{1-6}$alkoxy may optionally be substituted by one or more groups R$^P$.

17. The tricyclic compound of claim 13 wherein R$^{42}$ is selected from the group consisting of 3-(N,N-diethylamino)propyl, 3-(pyrrolidin-1-yl)propyl, (Z)-3-(N,N-diethylamino)prop-1-enyl, (Z)-3-(azetidin-1-yl)prop-1-enyl and (Z)-3-(pyrrolidin-1-yl)prop-1-enyl.

18. A compound selected from the group consisting of: 8-[2-((Z)-3-diethylaminoprop-1-enyl)-4-fluorobenzenesulfonylamino]-pyrazolo[5,1-a]isoquinoline-7-carboxylic acid; 7-[2-((Z)-3-diethylaminoprop-1-enyl)-4-fluorobenzenesulfonylamino]-4H-benzo[b]pyrrolo[1,2-d][1,4]oxazine-6-carboxylic acid; 8-[2-((Z)-3-diethylaminoprop-1-enyl)-4-fluorobenzenesulfonylamino]-5,6-dihydropyrazolo[5,1-a]isoquinoline-7-carboxylic acid; 7-[2-((Z)-3-diethylaminoprop-1-enyl)-4-fluorobenzenesulfonylamino]-4H-5-oxa-3,9b-diazacyclopenta[a]naphthalene-6-carboxylic acid and pharmaceutically acceptable salts, stereoisomers, esters and prodrugs thereof.

19. A pharmaceutically acceptable composition comprising a compound of claim 1 and a pharmaceutically acceptable excipient.

20. A pharmaceutically acceptable composition comprising a compound of claim 18, and a pharmaceutically acceptable excipient.

21. A pharmaceutically acceptable composition comprising a compound of claim 13, and a pharmaceutically acceptable excipient.

\* \* \* \* \*